(12) United States Patent
Weichert et al.

(10) Patent No.: US 7,576,108 B2
(45) Date of Patent: Aug. 18, 2009

(54) SUBSTITUTED ARYLCYCLOPROPYLACETAMIDES AS GLUCOKINASE ACTIVATORS

(75) Inventors: Andreas Gerhard Weichert, Hamburg (DE); David Gene Barrett, Henstedt-Ulzburg (DE); Stefan Heuser, Hamburg (DE); Rainer Riedl, Norderstedt (DE); Mark Joseph Tebbe, Durham, NC (US); Andrea Zaliani, Hamburg (DE)

(73) Assignee: Eli Lilly and Company, Indianapolis, IN (US)

( * ) Notice: Subject to any disclaimer, the term of this patent is extended or adjusted under 35 U.S.C. 154(b) by 377 days.

(21) Appl. No.: 10/541,047

(22) PCT Filed: Dec. 16, 2003

(86) PCT No.: PCT/US03/37088

§ 371 (c)(1), (2), (4) Date: Jun. 29, 2005

(87) PCT Pub. No.: WO2004/063179

PCT Pub. Date: Jul. 29, 2004

(65) Prior Publication Data

US 2006/0111353 A1    May 25, 2006

Related U.S. Application Data

(60) Provisional application No. 60/438,539, filed on Jan. 6, 2003.

(51) Int. Cl.
A61K 31/433 (2006.01)
A61K 31/426 (2006.01)
A61K 31/421 (2006.01)
C07D 285/135 (2006.01)
C07D 277/46 (2006.01)
C07D 263/48 (2006.01)

(52) U.S. Cl. ............... 514/363; 514/371; 514/377; 548/139; 548/195; 548/233

(58) Field of Classification Search ........... 514/363, 514/371, 377; 548/139, 195, 233
See application file for complete search history.

(56) References Cited

FOREIGN PATENT DOCUMENTS

| WO | WO 01/36415 | 5/2001 |
| WO | WO 0136415 A1 * | 5/2001 |
| WO | WO 01/83465 | 11/2001 |
| WO | WO 01/85706 | 11/2001 |
| WO | WO 01/85707 | 11/2001 |

* cited by examiner

Primary Examiner—Rei-Tsang Shiao
Assistant Examiner—Joseph R Kosack
(74) Attorney, Agent, or Firm—James B. Myers

(57) ABSTRACT

According to the present invention there is provided a compounds of formula (I): and pharmaceutically acceptable salts thereof.

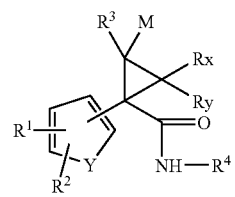

18 Claims, No Drawings

SUBSTITUTED ARYLCYCLOPROPYLACETAMIDES AS GLUCOKINASE ACTIVATORS

This is the national phase application, under 35 USC 371, for PCT/US2003/037088, filed 16 Dec. 2003, which, claims the benefit, under 35 USC 119(e), of U.S. provisional application 60/438,539, filed 6 Jan. 2003.

Glucokinase (GK, Hexokinase IV) is one of four hexokinases that are found in mammals [Colowick, S. P., in *The Enzymes*, Vol. 9 (P. Boyer, ed.) Academic Press, New York, N.Y., pages 1-48, 1973]. The hexokinases catalyze the first step in the metabolism of glucose, i.e., the conversion of glucose to glucose-6-phosphate, Glucokinase has a limited cellular distribution, being found principally in pancreatic beta-cells and hepatocytes. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97-115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10-15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463-496, 1993]. These findings contributed over a decade ago to the hypothesis that GK functions as a glucose sensor in beta-cells and hepatocytes (Meglasson, M. D. and Matschinsky, F. M. *Amer. J. Physiol.* 246, E1-E13, 1984). In recent years, studies in transgenic animals have confirmed that GK plays a critical role in whole-body glucose homeostasis. Animals that do not express GK die within days of birth with severe diabetes while animals overexpressing GK have improved glucose tolerance (Grupe, A., Hultgren, B.; Ryan, A. et al., *Cell* 83, 69-78, 1995; Ferrie, T., Riu, E., Bosch, F. et al., *FASEB J.*, 10, 1213-1218, 1996). An increase in glucose exposure is coupled through GK in beta-cells to increased insulin secretion and in hepatocytes to increased glycogen deposition.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226-230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in-beta-cells and hepatocytes, which will be coupled to increased insulin secretion and increased glucose utilization and glycogen synthesis. Such agents would be useful for treating type II diabetes.

According to the present invention there is provided compounds of formula (I):

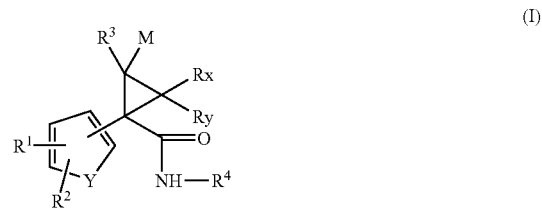

wherein
Y is —CH=CH—, —CH=N—, sulfur or oxygen; and
M is hydrogen, halo, lower alkyl or perfluoro-lower alkyl; and
Rx and Ry are hydrogen, halo or methyl; and
$R^1$ and $R^2$ are independently hydrogen, halo, amino, hydroxyamino, nitro, cyano, sulfonamido, lower alkyl, —$OR^5$, —$COOR^5$, perfluoro- lower alkyl lower alkyl thio, perfluoro-lower alkyl thio, lower alkyl sulfonyl, perfluoro lower alkyl sulfonyl, lower alkyl sulfinyl,
$R^5$ is hydrogen, lower alkyl or perfluoro-lower alkyl; or furthermore
$R^1$, $R^2$ can be —$(CH_2)n$-$NR^6R^7$, with n=1, 2, 3 or 4 and
$R^6$ and $R^7$ are independently hydrogen or lower alkyl; or together with the nitrogen atom to which they are attached form a five or six-membered heteroaromatic ring containing from 1 to 3 heteroatoms selected from sulfur, oxygen or nitrogen; or a saturated 5- or 6-membered cycloheteroalkyl ring, which contains from 1 to 2 heteroatoms selected from the group consisting of oxygen, sulfur and nitrogen; or
$R^1$, $R^2$ can be alkinyl, substituted with hydrogen, lower alkyl, hydroxy lower alkyl, lower alkoxy lower alkyl, an unsubstituted or hydroxy substituted cycloalkyl ring containing 5 or 6 carbon atoms, a five- or six-membered saturated heterocyclic ring which contains from 1 to 3 hetero atoms selected from the group consisting of sulfur, oxygen or nitrogen, or an unsubstituted five- or six-membered heteroaromatic ring, connected by a ring carbon atom, which contains from 1 to 3 heteroatoms in the ring selected from the group consisting of sulfur, nitrogen and oxygen, or —$(CH_2)n$-$NR^8R^9$, with n=1, 2, and
$R^8$ and $R^9$ are independently hydrogen or lower alkyl; or together with the nitrogen atom to which they are attached form a five or six-membered heteroaromatic ring containing from 1 to 3 heteroatoms selected from sulfur, oxygen or nitrogen; or a saturated 5- or 6-membered cycloheteroalkyl ring, which contains from 1 to 2 heteroatoms selected from the group consisting of oxygen, sulfur and nitrogen; or
$R^1$, $R^2$ can be $R^{10}$—[$(CH_2)y$-W]z-, with
W is oxygen, sulfur, —SO—, —$SO_2$—, and
$R^{10}$ is a heteroaromatic ring, connected by a ring carbon atom, which contains from 5 to 6 ring members with from 1 to 2 heteroatoms selected from the group consisting of oxygen, sulfur or nitrogen, or
aryl containing 6 or 10 ring carbon atoms, or
aryl containing from 6 ring carbon atoms fused with a heteroaromatic ring containing 5 or 6 ring members with 1 or 2 heteroatoms in the ring being selected from the group consisting of nitrogen, oxygen or sulfur, or
a saturated 5- or 6-membered cycloheteroalkyl ring, which contains from 1 to 2 heteroatoms selected from the group consisting of oxygen, sulfur and nitrogen, or a cycloalkyl ring having 5 or 6 carbon atoms, or —NR$^{11}$R$^{12}$, with R$^{11}$ and R$^{12}$ are independently hydrogen or lower alkyl;

y is independently 0, 1, 2, 3 or 4; z is independently 0,1; or

R$^1$, R$^2$ can be R$^{13}$—(CH$_2$)t-U—, with

U is —NHCO—, —CONH—, —NHSO$_2$—, —SO$_2$NH— and

R$^{13}$ in the same meaning of R$^{10}$ and perfluoro-lower alkyl, lower alkyl, lower alkoxycarbonyl or —NR$^{14}$R$^{15}$, R$^{14}$ and R$^{15}$ are independently hydrogen or lower alkyl; or together with the nitrogen atom to which they are attached form a five or six-membered heteroaromatic ring containing from 1 -to 3 heteroatoms selected from sulfur, oxygen or nitrogen; or a saturated 5- or 6-membered heterocycloalkyl ring, which contains from 1 to 2 heteroatoms selected from the group consisting of oxygen, sulfur and nitrogen;

t is an integer being 0, 1, 2, 3 or 4;

R$^3$ is lower alkyl or halo lower alkyl having from 2 to 6 carbon atoms or arylalkyl or —(CH$_2$)s-V where V is a 3 to 8-membered ring which is cycloalkyl, cycloalkenyl, or heterocycloalkyl having one heteroatom selected from oxygen and sulfur;

s is independently 0, 1 or 2;

R$^4$ is —C(O)NHR$^{16}$, or is R$^{17}$;

R$^{16}$ is hydrogen, lower alkyl, lower alkenyl, hydroxy lower alkyl,

—(CH$_2$)n-COOR$^{18}$, —CO—(CH$_2$)n-COOR$^{19}$;

R$^{17}$ is an unsubstituted, mono- or di-substituted five- or six-membered heteroaromatic ring connected by a ring carbon atom to the amide group shown, which five- or six-membered heteroaromatic ring contains from 1 to 4 heteroatoms selected from sulfur, oxygen or nitrogen, with one heteroatom being nitrogen which is adjacent to the connecting ring carbon atom; said mono- or di-substituted heteroaromatic ring being mono- or di-substituted at a position on a ring carbon atom other than adjacent to said connecting carbon atom with a substituent selected from the group consisting of lower alkyl, halo, nitro, cyano, —(CH$_2$)n-OR$^{20}$, —(CH$_2$)n-COOR$^{21}$, —(CH$_2$)n-CONHR$^{22}$, —(CH$_2$)n-NHR$^{23}$, n is 0, 1, 2, 3 or 4;

R$^{18}$, R$^{19}$, R$^{20}$, R$^{21}$, R$^{22}$ and R$^{23}$ are independently hydrogen or lower alkyl, and its pharmaceutically acceptable salts thereof.

The compounds of formula I have been found to activate glucokinase in vitro. Preferably the compounds of formula I have an enhanced solubility profile and further, have improved metabolic stability over the compounds of the prior art. They are particularly useful for increasing insulin secretion in the treatment of type II diabetes.

The present invention provides pharmaceutical compositions comprising a compound of formula I, or a pharmaceutically acceptable salt thereof together with a pharmaceutically acceptable diluent or carrier.

Further, the present invention provides a compound of formula I, or a pharmaceutically acceptable salt thereof for use as a pharmaceutical; and a compound of formula I, or a pharmaceutically acceptable salt thereof for use in the treatment or prophylaxis of type II diabetes.

The present invention also provides the use of a compound of formula I, or a pharmaceutically acceptable salt thereof, in the manufacture of a medicament for the treatment or prophylaxis of disorders associated with GK dysfunction in mammals; the use of a compound of formula I, or a pharmaceutically acceptable salt thereof, in the manufacture of a medicament for the treatment or prophylaxis of type II diabetes.

The present invention further relates to processes for the preparation of the compounds of formula I, or pharmaceutically acceptable salts thereof. In addition, the present invention relates to a method for the prophylactic or therapeutic treatment of type II diabetes, which method comprises administering an effective amount of a compound of formula I or a pharmaceutically acceptable salt thereof; to a human being or an animal in need thereof.

The present invention includes the pharmaceutically acceptable salts of the compounds of formula I. As used herein, the term "pharmaceutically acceptable salts" include acid addition salts, including salts formed with inorganic acids, for example hydrochloric, hydrobromic, nitric, sulphuric or phosphoric acids, or with organic acids, such as organic carboxylic or organic sulphonic acids, for example, acetoxybenzoic, citric, glycolic, o- mandelic-l, mandelic-dl, mandelic d, maleic, mesotartaric monohydrate, hydroxymaleic, fumaric, lactobionic, malic, methanesulphonic, napsylic, naphthalenedisulfonic, naphtoic, oxalic, palmitic, phenylacetic, propionic, pyridyl hydroxy pyruvic, salicylic, stearic, succinic, sulfanilic, tartaric, 2-hydroxyethane sulphonic, toluene-p-sulphonic, and xinafoic acids. The term "pharmaceutically acceptable salts" also includes any pharmaceutically acceptable base salt such as amine salts, trialkyl amine salts and the like.

In addition to the pharmaceutically acceptable salts, other salts are included in the invention. They may serve as intermediates in the purification of compounds or in the preparation of other, for example pharmaceutically acceptable, acid addition salts, or are useful for identification, characterisation or purification.

It will be appreciated that the compounds of the invention can contain one or more asymmetric carbon atoms which gives rise to stereoisomers. The compounds are normally prepared as racemic mixtures, but individual isomers can be isolated by conventional techniques if so desired. Racemic mixtures, enantiomers, diastereomers and individual isomers form part of the present invention, the compounds being employed as racemates or in enantiomerically pure form.

When the term "syn" is utilized in this application, it designates that the vicinal (hetero)aryl group and the R$^3$ substituent are located on the same side of the cyclopropane system.

As used throughout this application, the term "halogen" and the term "halo", unless otherwise stated, designate all four halogens, i.e. fluorine, chlorine, bromine and iodine. A preferred halogen is chlorine or fluorine. When R$^1$ and/or R$^2$ is halo, chlorine is especially preferred. When M, Rx or Ry is halo, fluorine is especially preferred.

As used herein, the term "lower alkyl" includes both straight chain and branched chain alkyl groups having from 1 to 7 carbon atoms, such as methyl, ethyl, propyl, isopropyl, preferably methyl and ethyl. With regard to R$^3$, isopropyl and n-propyl are preferred, especially preferred are isopropyl and isobutyl.

As used herein, the term "Halo lower alkyl" designates a lower alkyl group wherein one or more of the hydrogens is replaced by a halogen as defined above, which replacement can be at any site on the lower alkyl, including the end, such as chloroethyl. With regard to R$^3$ fluoro lower alkyl is preferred.

As used herein, the term "Fluoro lower alkyl" designates a lower alkyl group wherein one or more of the hydrogens is replaced by fluorine, which replacement can be at any site on the lower alkyl, including the end, such as 1,1,1-trifluoroethane, 1,1,1-trifluoropropane and 1,1,1,3,3,3-hexafluoroisopropyl. A preferred fluoro lower alkyl group is 1,1,1,3,3,3-hexafluoroisopropyl.

The term "hydroxy lower alkyl" includes any hydroxy lower alkyl group where lower alkyl is defined as above. The hydroxy can be substituted at any place on the lower alkyl group such as hydroxy methyl, 1-hydroxy ethyl, 2-hydroxy propyl, 2-hydroxy isopropyl or 2-hydroxy-2-butyl. "Lower alkoxy lower alkyl" denotes any hydroxy lower alkyl group wherein the hydrogen of the hydroxy moiety is substituted by lower alkyl.

As used herein, "perfluoro-lower alkyl" means any lower alkyl group wherein all of the hydrogens of the lower alkyl group are substituted or replaced by fluoro. Among the preferred perfluoro-lower alkyl groups are trifluoromethyl, pentafluoroethyl, heptafluoropropyl, etc. An especially preferred perfluoro-lower alkyl group is trifluoromethyl.

As used herein, "lower alkyl thio" means a lower alkyl group as defined above where a thio group is bound to the rest of the molecule. Similarly "perfluoro-lower alkyl thio" means a perfluoro-lower alkyl group as defined above where a thio group is bound to the rest of the molecule.

As used herein, "lower alkyl sulfonyl" means a lower alkyl group as defined above where a sulfonyl group is bound to the rest of the molecule, preferably lower alkyl sulfonyl is methyl sulfonyl. Similarly "perfluoro-lower alkyl sulfonyl" means a perfluoro-lower alkyl group as defined above where a sulfonyl group is bound to the rest of the molecule As used herein, "hydroxyamino" designates an amino group where one of the hydrogens is replaced by a hydroxy.

As used herein, "cycloalkyl" means a saturated hydrocarbon ring having from 3 to 8 carbon atoms, preferably from 5 to 6 carbon atoms, such as cyclopentyl and cyclohexyl. Especially preferred cycloalkyl is cyclopentyl.

As used herein, "heterocycloalkyl" means a saturated hydrocarbon ring having from 3 to 8 carbon atoms, preferably from 5 to 7 carbon atoms, and having one to two heteroatoms which may be oxygen, sulfur or nitrogen. With regard to $R^3$ it is preferred to have a single heteroatom, preferably oxygen.

As used herein, "cycloalkenyl" means a cycloalkyl ring having from 3 to 8, and preferably from 5 to 7 carbon atoms, where one of the bonds between the ring carbons is unsaturated.

As used herein, the term "lower alkenyl" denotes an alkylene group having from 2 to 6 carbon atoms with a double bond located between any two adjacent carbons of the group, such as allyl and crotyl.

As used herein, the term "lower alkoxy" includes both straight chain and branched chain alkoxy groups having from 1 to 7 carbon atoms, such as methoxy, ethoxy, propoxy, isopropoxy, preferably methoxy and ethoxy.

As used herein, the term "aryl" signifies aryl mononuclear aromatic hydrocarbon groups such as phenyl, tolyl, etc. which can be unsubstituted or substituted in one or more positions with halogen, nitro, lower alkyl, or lower alkoxy substituents and polynuclear aryl groups, such as naphthyl, anthryl, and phenanthryl, which can be unsubstituted or substituted with one or more of the aforementioned groups. Preferred aryl groups are the substituted and unsubstituted mononuclear aryl groups, particularly phenyl.

As used herein, the term "arylalkyl" denotes an alkyl group, preferably lower alkyl, in which one of the hydrogen atoms is replaced by an aryl group. Examples of arylalkyl groups are benzyl, 2-phenylethyl, 3-phenylpropyl, 4-chlorobenzyl, 4-methoxybenzyl and the like.

As used herein, the term "lower alkanoic acid" denotes lower alkanoic acids containing from 2 to 7 carbon atoms such as propionic acid, acetic acid and the like. The term "lower alkanoyl" denotes monovalent alkanoyl groups having from 2 to 7 carbon atoms such as propionoyl, acetyl and the like. The term "aroic acids" denotes aryl alkanoic acids where aryl is as defined above and alkanoic contains from 1 to 6 carbon atoms. The term "aroyl" denotes aroic acids wherein aryl is as defined hereinbefore, with the hydrogen group of the COOH moiety removed. Among the preferred aroyl groups is benzoyl.

The heteroaromatic ring in $R^4$ can be an unsubstituted, mono- or di-substituted five- or six-membered heteroaromatic ring having from 1 to 3 heteroatoms selected from the group consisting of oxygen, nitrogen or sulfur and connected by a ring carbon to the amine of the amide group shown. The heteroaromatic ring contains a first nitrogen heteroatom adjacent to the connecting ring carbon atom and if present, the other heteroatoms can be sulfur, oxygen or nitrogen. Heteroaromatic rings include, for example, pyrazinyl, pyridazinyl, isoxazolyl, isothiazolyl, pyrazolyl, pyridinyl, pyrimidinyl, thiadiazolyl (preferably 1,3,4-, 1,2,3--, 1,2,4-), triazinyl (preferably 1,3,5-, 1,2,4-), thiazolyl, oxazolyl, and imidazolyl. The preferred heteroaromatic rings which constitute $R^4$ are connected via a ring carbon atom to the amide group to form the amides of formula I.

$R^4$ is preferably an unsubstituted, mono- or di-substituted five- or six-membered, heteroaromatic ring containing from 1 to 3 hetero atoms selected from the group consisting of nitrogen, oxygen or sulfur, with one hetero atom being nitrogen and connected to the remainder of the molecule by a ring carbon atom. In this case, the preferred rings are those containing a nitrogen heteroatom adjacent to the connecting ring carbon. When $R^4$ is an unsubstituted, mono- or di-substituted five- or six-membered heteroaromatic ring, the preferred rings are those which contain a nitrogen heteroatom adjacent to the connecting ring carbon and a second heteroatom adjacent to the connecting ring carbon or adjacent to said first heteroatom. Preferably $R^4$ is a five-membered heteroaromatic ring. The preferred five-membered heteroaromatic rings contain 2 or 3 heteroatoms. Examples of such five-membered heteroaromatic rings are thiazolyl, imidazolyl, oxazolyl and thiadiazolyl, with thiazolyl being especially preferred.

When the heteroaromatic ring is a six-membered heteroaromatic, the ring is connected by a ring carbon atom to the amine group shown, with one nitrogen heteroatom being adjacent to the connecting ring carbon atom. The preferred six-membered heteroaromatic rings include, for example, pyridinyl, pyrimidinyl, pyrazinyl, pyridazinyl, and triazinyl with pyridinyl being especially preferred.

Above heteroaromatic rings $R^4$ may optionally be mono- or di-substituted at a position on a ring carbon atom other than adjacent to said connecting carbon atom with a substituent selected from the group consisting lower alkyl, halo, nitro, cyano, —$(CH_2)n$-$OR^{20}$, —$(CH_2)n$-$C(O)OR^{21}$, —$(CH_2)n$-$CONHR^{22}$, —$(CH_2)n$-$NHR^{23}$, with n, $R^{20}$, $R^{21}$, $R^{22}$ and $R^{23}$ being as defined above.

During the course of the synthetic sequence the various functional groups such as the free carboxylic acid or hydroxy groups will be protected via conventional hydrolyzable ester or ether protecting groups. As used herein the term "hydrolyzable ester or ether protecting groups" designates any ester or ether conventionally used for protecting carboxylic acids or alcohols which can be hydrolyzed to yield the respective hydroxyl or carboxyl group. Exemplary ester groups useful for those purposes are those in which the acyl moieties are derived from a lower alkanoic, aryl lower alkanoic, or lower alkane dicarboxcyclic acid. Among the activated acids which can be utilized to form such groups are acid anhydrides, acid halides, preferably acid chlorides or acid bromides derived from aryl or lower alkanoic acids. Example of anhydrides are anhydrides derived from monocarboxylic acid such as acetic anhydride, benzoic acid anhydride, and lower alkane dicarboxylic acid anhydrides, e.g. succinic anhydride as well as chloro formats e.g. trichloro, ethylchloro formate being preferred. A suitable ether protecting group for alcohols are, for example, the tetrahydropyranyl ethers such as 4-methoxy-5, 6-dihydroxy-2H-pyranyl ethers. Others are aroylmethyl-ethers such as benzyl, benzhydryl or trityl ethers or a-lower alkoxy lower alkyl ethers, for example, methoxymethyl or allylic ethers or alkyl silylethers such as trimethylsilylether.

As used herein, the term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under mildly-acidic conditions at about pH 3.0. Particularly preferred amino protecting groupsare t-butoxycarbonyl (BOC), carbobenzyloxy (CBZ) and 9-flurorenylmethoxycarbonyl(FMOC).

The compound of formula I of this invention constitutes two preferred species, i.e., the compound of formula

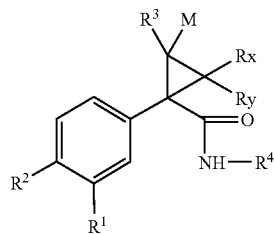

(I-A)

wherein M, $R^1$, $R^2$, $R^3$, $R^4$, Rx and Ry are as above;
and the compound of the formula

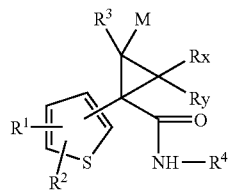

(I-B)

wherein M, $R^1$, $R^2$, $R^3$, $R^4$, Rx and Ry are as above;

In accordance with one preferable embodiment of the compound of formula I, $R^3$ is lower alkyl having from 2 to 6 carbon atoms, preferred lower alkyl residues being isopropyl and n-propyl. In one preferred embodiment $R^3$ is isobutyl, in another $R^3$ is isopropyl. In another preferable embodiment $R^3$ is —(CH$_2$)s-V where s and V are as defined above, the preferred V substituent being a cycloalkyl group which contains from 3 to 8 carbon atoms. In one preferred embodiment V is cyclopentyl, in another V is cyclohexyl. In another preferable embodiment $R^3$ is halo lower alkyl having from 2 to 6 carbon atoms, preferred halo lower alkyl residues being fluoro lower alkyl as defined above.

Preferred compounds are where the aryl/heteroaryl substituent of the formula:

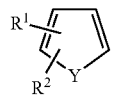

and the group $R^3$ have a syn relationship.

Preferred $R^4$ substituent in accordance with the present invention is where $R^4$ is $R^{17}$ as defined above. Further preferred $R^{17}$ substituents are unsubstituted, mono- or di-substituted thiazolyl, imidazolyl, oxazolyl, thiadiazolyl, pyridinyl, pyrimidinyl, pyrazinyl, pyridazinyl, and triazinyl. In one preferred embodiment $R^{17}$ is thiazolyl, in another $R^{17}$ is pyridinyl. In accordance with further preferable embodiments, the heteroaromatic ring $R^{17}$ is either unsubstituted, mono- or di-substituted independently with lower alkyl, halogen or —(CH$_2$)n-C(O)OR$^{21}$, wherein n and $R^{21}$ are as defined above. In another preferable embodiment M is hydrogen, fluoro or lower alkyl. Further preferred M subtituents are hydrogen, fluoro methyl or ethyl. In one preferred embodiment M is hydrogen, in another M is methyl. In another preferred embodiment Rx and Ry are hydrogen, fluoro or methyl. In one preferred embodiment Rx and Ry are hydrogen, in another Rx and Ry are methyl, in another Rx and Ry are fluoro.

In accordance with another preferable embodiment of the compound of formula I, substituent $R^1$ is selected from the group consisting of hydrogen, halo, nitro, cyano, perfluoro lower alkyl, and lower alkyl sulfonyl. A further preferred $R^1$ substituent is selected from the group consisting of hydrogen, halo, nitro, cyano or perfluoro lower alkyl. In one preferred embodiment $R^1$ is halo, in another $R^1$ is hydrogen. Preferred substituent $R^2$ is selected from the group consisting of hydrogen, halo, nitro, cyano, perfluoro lower alkyl, lower alkyl sulfonyl, $R^{10}$—[(CH$_2$)y-W]z and $R^{13}$—(CH$_2$)t-U— where $R^{10}$, $R^{13}$, W, U, t, y and z are as defined above. Further preferred $R^2$ substituents are halo, lower alkyl sulfonyl, $R^{10}$—[(CH$_2$)y-W]z and $R^{13}$—(CH$_2$)t-U— where $R^{10}$, $R^{13}$, W, U, t, y and z are as defined above. In one preferred embodiment $R^2$ is lower alkyl sulfonyl, in another $R^2$ is $R^{10}$—[(CH$_2$)y-W]z where $R^{10}$, W, U, y and z are as defined above, in another $R^2$ is $R^{13}$—(CH$_2$)t-U— where $R^{13}$, U and t, are as defined above. In a further preferred embodiment $R^2$ is sulphonyl methyl, in another $R^2$ is $R^{10}$—[(CH$_2$)y-W]z where W is SO$_2$ and $R^{10}$, U, y and z are as defined above.

In accordance with one embodiment of the compound of formula I-A, $R^3$ can be —(CH$_2$)s-V where s and V are as defined above, the preferred V substituent being a cycloalkyl group which contains from 3 to 8 carbon atoms, preferably cyclopentyl or cyclohexyl (compound I-A1). Another embodiment of the compounds of formula I-A are those compounds where $R^3$ is lower alkyl having from 2 to 6 carbon atoms, preferably lower alkyl residues being isobutyl or isopropyl (compound I-A2).

Among the embodiments of the compound of formula I-A, $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A3).

Among the embodiments of the compound of formula I-A, $R^1$ can be hydrogen, halo, nitro, cyano or perfluoro lower alkyl, and particularly those compounds where $R^1$ is halo or hydrogen (compound I-A4).

Among the embodiments of the compound of formula I-A, $R^2$ can be halo, lower alkyl sulfonyl, $R^{10}$—[(CH$_2$)y-W]z and $R^{13}$—(CH$_2$)t-U— where $R^{10}$, $R^{13}$, W, U, t, y and z are as defined above, and particularly those compounds where $R^2$ is sulphonyl methyl or $R^{10}$—[(CH$_2$)y-W]z where W is SO$_2$ and $R^{10}$, y and z are as defined above (compound I-A5).

Among the embodiments of the compound of formula I-A1, $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A1(a)).

Among the embodiments of the compound of formula I-A1, $R^1$ can be hydrogen, halo, nitro, cyano or perfluoro lower alkyl, and particularly those compounds where $R^1$ is halo or hydrogen (compound I-A1(b)).

Among the embodiments of the compound of formula I-A1, $R^2$ can be halo, lower alkyl sulfonyl, $R^{10}$—[$(CH_2)$y-W]z and $R^{13}$—$(CH_2)$t-U— where $R^{10}$, $R^{13}$, W, U, t, y and z are as defined above, and particularly those compounds where $R^2$ is sulphonyl methyl or $R^{10}$—[$(CH_2)$y-W]z where W is $SO_2$ and $R^{10}$, y and z are as defined above (compound I-A1(c)).

Among the embodiments of the compound of formula I-A2, $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A2(a)).

Among the embodiments of the compound of formula I-A2, $R^1$ can be hydrogen, halo, nitro, cyano or perfluoro lower alkyl, and particularly those compounds where $R^1$ is halo or hydrogen (compound I-A2(b)).

Among the embodiments of the compound of formula I-A2, $R^2$ can be halo, lower alkyl sulfonyl, $R^{10}$—[$(CH_2)$y-W]z and $R^{13}$—$(CH_2)$t-U— where $R^{10}$, $R^{13}$, W, U, t, y and z are as defined above, and particularly those compounds where $R^2$ is sulphonyl methyl or $R^{10}$—[$(CH_2)$y-W]z where W is $SO_2$ and $R^{10}$, y and z are as defined above (compound I-A2(c)).

Among the embodiments of the compound of formula I-A3, $R^3$ can be —$(CH_2)$s-V where s and V are as defined above, the preferred V substituent being a cycloalkyl group which contains from 3 to 8 carbon atoms, preferably cyclopentyl or cyclohexyl (compound I-A3(a)).

Among the embodiments of the compound of formula I-A3 are those compounds where $R^3$ is lower alkyl having from 2 to 6 carbon atoms, preferably lower alkyl residues being isobutyl or isopropyl (compound I-A3(b)).

Among the embodiments of the compound of formula I-A3, $R^1$ can be hydrogen, halo, nitro, cyano or perfluoro lower alkyl, and particularly those compounds where $R^1$ is, halo or hydrogen (compound I-A3(c)).

Among the embodiments of the compound of formula I-A3, $R^2$ can be halo, lower alkyl sulfonyl, $R^{10}$—[$(CH_2)$y-W]z and $R^{13}$—$(CH_2)$t-U— where $R^{10}$, $R^{13}$, W, U, t, y and z are as defined above, and particularly those compounds where $R^2$ is sulphonyl methyl or $R^{10}$—[$(CH_2)$y-W]z where W is $SO_2$ and $R^{10}$, y and z are as defined above (compound I-A3(d)).

Among the embodiments of the compound of formula I-A4, $R^3$ can be —$CH_2$)s-V where s and V are as defined above, the preferred V substituent being a cycloalkyl group which contains from 3 to 8 carbon atoms, preferably cyclopentyl or cyclohexyl (compound I-A4(a)).

Among the embodiments of the compound of formula I-A4 are those compounds where $R^3$ is lower alkyl having from 2 to 6 carbon atoms, preferably lower alkyl residues being isobutyl or isopropyl (compound I-A4(b)).

Among the embodiments of the compound of formula I-A4, $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A4(c)).

Among the embodiments of the compound of formula I-A4, $R^2$ can be halo, lower alkyl sulfonyl, $R^{10}$—[$(CH_2)$y-W]z and $R^{13}$—$(CH_2)$t-U— where $R^{10}$, $R^{13}$, W, U, t, y and z are as defined above, and particularly those compounds where $R^2$ is sulphonyl methyl or $R^{10}$—[$(CH_2)$y-W]z where W is $SO_2$ and $R^{10}$, y and z are as defined above (compound I-A4(d))

Among the embodiments of the compound of formula I-A5, $R^3$ can be —$(CH_2)$s-V where s and V are as defined above, the preferred V substituent being a cycloalkyl group which contains from 3 to 8 carbon atoms, preferably cyclopentyl or cyclohexyl (compound I-A5(a)).

Among the embodiments of the compound of formula I-A5 are those compounds where $R^3$ is lower alkyl having from 2 to 6 carbon atoms, preferably lower alkyl residues being isobutyl or isopropyl (compound I-A5(b)).

Among the embodiments of the compound of formula I-A5, $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A5(c)).

Among the embodiments of the compound of formula I-A5, $R^1$ can be hydrogen, halo, nitro, cyano or perfluoro lower alkyl, and particularly those compounds where $R^1$ is halo or hydrogen (compound I-A5(d)).

Among the embodiments of the compound of formula I-A1(a), $R^1$ can be hydrogen, halo, nitro, cyano or perfluoro lower alkyl, and particularly those compounds where $R^1$ is halo or hydrogen (compound I-A1(a-1)).

Among the embodiments of the compound of formula I-A1(a), $R^2$ can be halo, lower alkyl sulfonyl, $R^{10}$—[$(CH_2)$y-W]z and $R^{13}$—$(CH_2)$t-U— where $R^{10}$, $R^{13}$, W, U, t, y and z are as defined above, and particularly those compounds where $R^2$ is sulphonyl methyl or $R^{10}$—[$(CH_2)$y-W]z where W is $SO_2$ and $R^{10}$, y and z are as defined above (compound I-A1(a-2)).

Among the embodiments of the compound of formula I-A1(b), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A1(b-1)).

Among the embodiments of the compound of formula I-A1(b), $R^2$ can be halo, lower alkyl sulfonyl, $R^{10}$—[$(CH_2)$y-W]z and $R^{13}$—$(CH_2)$t-U— where $R^1$, $R^{13}$, W, U, t, y and z are as defined above, and particularly those compounds where $R^2$ is sulphonyl methyl or $R^{10}$—[$(CH_2)$y-W]z where W is $SO_2$ and $R^{10}$, y and z are as defined above (compound I-A1(b-2)).

Among the embodiments of the compound of formula I-A1(c), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A1(c-1)).

Among the embodiments of the compound of formula I-A1(c), $R^1$ can be hydrogen, halo, nitro, cyano or perfluoro lower alkyl, and particularly those compounds where $R^1$ is halo or hydrogen (compound I-A1(c-2)).

Among the embodiments of the compound of formula I-A2(a), $R^1$ can be hydrogen, halo, nitro, cyano or perfluoro lower alkyl, and particularly those compounds where $R^1$ is halo or hydrogen (compound I-A2(a-1)).

Among the embodiments of the compound of formula I-A2(a), $R^2$ can be halo, lower alkyl sulfonyl, $R^{10}$—[$(CH_2)$y-W]z and $R^{13}$—$(CH_2)$t-U— where $R^{10}$, $R^{13}$, W, U, t, y and z are as defined above, and particularly those compounds where $R^2$ is sulphonyl methyl or $R^{10}$—[$(CH_2)$y-W]z where W is $SO_2$ and $R^{10}$, y and z are as defined above (compound I-A2(a-2)).

Among the embodiments of the compound of formula I-A2(b), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A2(b-1)).

Among the embodiments of the compound of formula I-A2(b), $R^2$ can be halo, lower alkyl sulfonyl, $R^{10}$—[(CH$_2$)y-W]z and $R^{13}$—(CH$_2$)t-U— where $R^{10}$, $R^{13}$, W, U, t, y and z are as defined above, and particularly those compounds where $R^2$ is sulphonyl methyl or $R^{10}$—[(CH$_2$)y-W]z where W is SO$_2$ and $R^{10}$, y and z are as defined above (compound I-A2(b-2)).

Among the embodiments of the compound of formula I-A2(c), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A2(c-1)).

Among the embodiments of the compound of formula I-A2(c), $R^1$ can be hydrogen, halo, nitro, cyano or perfluoro lower alkyl, and particularly those compounds where $R^1$ is halo or hydrogen (compound I-A2(c-2)).

Among the embodiments of the compound of formula I-A3(a), $R^1$ can be hydrogen, halo, nitro, cyano or perfluoro lower alkyl, and particularly those compounds where $R^1$ is halo or hydrogen (compound I-A3(a-1)).

Among the embodiments of the compound of formula I-A3(a), $R^2$ can be halo, lower alkyl sulfonyl, $R^{10}$—[(CH$_2$)y-W]z and $R^{13}$—(CH$_2$)t-U— where $R^{10}$, $R^{13}$, W, U, t, y and z are as defined above, and particularly those compounds where $R^2$ is sulphonyl methyl or $R^{10}$—[(CH$_2$)y-W]z where W is SO$_2$ and $R^{10}$, y and z are as defined above (compound I-A3(a-2)).

Among the embodiments of the compound of formula I-A3(b), $R^1$ can be hydrogen, halo, nitro, cyano or perfluoro lower alkyl, and particularly those compounds where $R^1$ is halo or hydrogen (compound I-A3(b-1)).

Among the embodiments of the compound of formula I-A3(b), $R^2$ can be halo, lower alkyl sulfonyl, $R^{10}$—[(CH$_2$)y-W]z and $R^{13}$—(CH$_2$)t-U— where $R^{10}$, $R^{13}$, W, U, t, y and z are as defined above, and particularly those compounds where $R^2$ is sulphonyl methyl or $R^{10}$—[(CH$_2$)y-W]z where W is SO$_2$ and $R^{10}$, y and z are as defined above (compound I-A3(b-2)).

Among the embodiments of the compound of formula I-A3(c), $R^3$ can be —CH$_2$)s-V where s and V are as defined above, the preferred V substituent being a cycloalkyl group which contains from 3 to 8 carbon atoms, preferably cyclopentyl or cyclohexyl (compound I-A3(c-1)).

Among the embodiments of the compound of formula I-A3(c) are those compounds where $R^3$ is lower alkyl having from 2 to 6 carbon atoms, preferably lower alkyl residues being isobutyl or isopropyl (compound I-A3(c-2)).

Among the embodiments of the compound of formula I-A3(c), $R^2$ can be halo, lower alkyl sulfonyl, $R^{10}$—[(CH$_2$)y-W]z and $R^{13}$—(CH$_2$)t-U— where $R^{10}$, $R^{13}$, W, U, t, y and z are as defined above, and particularly those compounds where $R^2$ is sulphonyl methyl or $R^{10}$—[(CH$_2$)y-W]z where W is SO$_2$ and $R^{10}$, y and z are as defined above (compound I-A3(c-3)).

Among the embodiments of the compound of formula I-A3(d), $R^3$ can be —(CH$_2$)s-V where s and V are as defined above, the preferred V substituent being a cycloalkyl group which contains from 3 to 8 carbon atoms, preferably cyclopentyl or cyclohexyl (compound I-A3(d-1)).

Among the embodiments of the compound of formula I-A3(d) are those compounds where $R^3$ is lower alkyl having from 2 to 6 carbon atoms, preferably lower alkyl residues being isobutyl or isopropyl (compound I-A3(d-2)).

Among the embodiments of the compound of formula I-A3(d) $R^1$ can be hydrogen, halo, nitro, cyano or perfluoro lower alkyl, and particularly those compounds where $R^1$ is halo or hydrogen (compound I-A3(d-3)).

Among the embodiments of the compound of formula I-A4(a), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A4(a-1)).

Among the embodiments of the compound of formula I-A4(a), $R^2$ can be halo, lower alkyl sulfonyl, $R^{10}$—[(CH$_2$)y-W]z and $R^{13}$—(CH$_2$)t-U— where $R^{10}$, $R^{13}$, W, U, t, y and z are as defined above, and particularly those compounds where $R^2$ is sulphonyl methyl or $R^{10}$—[(CH$_2$)y-W]z where W is SO$_2$ and $R^{10}$, y and z are as defined above (compound I-A4(a-2)).

Among the embodiments of the compound of formula I-A4(b), $R^4$ is $R^7$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A4(b-1)).

Among the embodiments of the compound of formula I-A4(b), $R^2$ can be halo, lower alkyl sulfonyl, $R^{10}$—[(CH$_2$)y-W]z and $R^{13}$—(CH$_2$)t-U— where $R^{10}$, $R^{13}$, W, U, t, y and z are as defined above, and particularly those compounds where $R^2$ is sulphonyl methyl or $R^{10}$—[(CH$_2$)y-W]z where W is SO$_2$ and $R^1$, y and z are as defined above (compound I-A4(b-2)).

Among the embodiments of the compound of formula I-A4(c), $R^3$ can be —CH$_2$)s-V where s and V are as defined above, the preferred V substituent being a cycloalkyl group which contains from 3 to 8 carbon atoms, preferably cyclopentyl or cyclohexyl (compound I-A4(c-1)).

Among the embodiments of the compound of formula I-A4(c) are those compounds where $R^3$ is lower alkyl having from 2 to 6 carbon atoms, preferably lower alkyl residues being isobutyl or isopropyl (compound I-A4(c-2)).

Among the embodiments of the compound of formula I-A4(c), $R^2$ can be halo, lower alkyl sulfonyl, $R^{10}$—[(CH$_2$)y-W]z and $R^{13}$—(CH$_2$)t-U— where $R^{10}$, $R^3$, W, U, t, y and z are as defined above, and particularly those compounds where $R^2$ is sulphonyl methyl or $R^{10}$—[(CH$_2$)y-W]z where W is SO$_2$ and $R^{10}$, y and z are as defined above (compound I-A4(c-3)).

Among the embodiments of the compound of formula I-A4(d), $R^3$ can be —CH$_2$)s-V where s and V are as defined above, the preferred V substituent being a cycloalkyl group which contains from 3 to 8 carbon atoms, preferably cyclopentyl or cyclohexyl (compound I-A4(d-1)).

Among the embodiments of the compound of formula I-A4(d) are those compounds where $R^3$ is lower alkyl having from 2 to 6 carbon atoms, preferably lower alkyl residues being isobutyl or isopropyl (compound I-A4(d-2)).

Among the embodiments of the compound of formula I-A4(d), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A4(d-3)).

Among the embodiments of the compound of formula I-A5(a), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A5(a-1)).

Among the embodiments of the compound of formula I-A5(a) $R^1$ can be hydrogen, halo, nitro, cyano or perfluoro lower alkyl, and particularly those compounds where $R^1$ is halo or hydrogen (compound I-A5(a-2)).

Among the embodiments of the compound of formula I-A5(b), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A5(b-1).

Among the embodiments of the compound of formula I-A5(b) $R^1$ can be hydrogen, halo, nitro, cyano or perfluoro lower alkyl, and particularly those compounds where $R^1$ is halo or hydrogen (compound I-A5(b-2))

Among the embodiments of the compound of formula I-A5(c), $R^3$ can be —$(CH_2)s$-V where s and V are as defined above, the preferred V substituent being a cycloalkyl group which contains from 3 to 8 carbon atoms, preferably cyclopentyl or cyclohexyl (compound I-A5(c-1)).

Among the embodiments of the compound of formula I-A5(c) are those compounds where $R^3$ is lower alkyl having from 2 to 6 carbon atoms, preferably lower alkyl residues being isobutyl or isopropyl (compound I-A5(c-2)).

Among the embodiments of the compound of formula I-A5(c) $R^1$ can be hydrogen, halo, nitro, cyano or perfluoro lower alkyl, and particularly those compounds where $R^1$ is halo or hydrogen (compound I-A5(c-3)).

Among the embodiments of the compound of formula I-A5(d), $R^3$ can be —$CH_2s$-V where s and V are as defined above, the preferred V substituent being a cycloalkyl group which contains from 3 to 8 carbon atoms, preferably cyclopentyl or cyclohexyl (compound I-A5(d-1)).

Among the embodiments of the compound of formula I-A5(d) are those compounds where $R^3$ is lower alkyl having from 2 to 6 carbon atoms, preferably lower alkyl residues being isobutyl or isopropyl (compound I-A5(d-2)).

Among the embodiments of the compound of formula I-A5(d) $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-A5(d-3)).

Among the embodiments of the compound of formula I-A3(a-1), $R^2$ can be halo, lower alkyl sulfonyl, $R^{10}$—[$(CH_2)$y-W]z and $R^{13}$—$(CH_2)$t-U— where $R^{10}$, $R^{13}$, W, U, t, y and z are as defined above, and particularly those compounds where $R^2$ is sulphonyl methyl or $R^{10}$—[$(CH_2)$y-W]z where W is $SO_2$ and $R^{10}$, y and z are as defined above.

Among the embodiments of the compound of formula I-A3(b-1), $R^2$ can be halo, lower alkyl sulfonyl, $R^{10}$—[$(CH_2)$y-W]z and $R^{13}$—$(CH_2)$t-U— where $R^{10}$, $R^{13}$, W, U, t, y and z are as defined above, and particularly those compounds where $R^2$ is sulphonyl methyl or $R^{10}$—[$(CH_2)$y-W]z where W is $SO_2$ and $R^{10}$, y and z are as defined above.

In accordance with one embodiment of the compound of formula I-B, $R^3$ can be —$(CH_2)s$-V where s and V are as defined above, the preferred V substituent being a cycloalkyl group which contains from 3 to 8 carbon atoms, preferably cyclopentyl or cyclohexyl (compound I-B1).

Another embodiment of the compounds of formula I-B are those compounds where $R^3$ is lower alkyl having from 2 to 6 carbon atoms, preferably lower alkyl residues being isobutyl or isopropyl (compound I-B2).

Among the embodiments of the compound of formula I-B, $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B3).

Among the embodiments of the compound of formula I-B, $R^1$ can be hydrogen, halo, nitro, cyano or perfluoro lower alkyl, and particularly those compounds where $R^1$ is halo or hydrogen (compound I-B4).

Among the embodiments of the compound of formula I-B, $R^2$ can be halo, lower alkyl sulfonyl, $R^{10}$—[$(CH_2)$y-W]z and $R^{13}$—$(CH_2)$t-U— where $R^{10}$, $R^{13}$, W, U, t, y and z are as defined above, and particularly those compounds where $R^2$ is sulphonyl methyl or $R^{10}$—[$(CH_2)$y-W]z where W is $SO_2$ and $R^{10}$, y and z are as defined above (compound I-B5).

Among the embodiments of the compound of formula I-B1, $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B1(a)).

Among the embodiments of the compound of formula I-B1, $R^1$ can be hydrogen, halo, nitro, cyano or perfluoro lower alkyl, and particularly those compounds where $R^1$ is halo or hydrogen (compound I-B1(b)).

Among the embodiments of the compound of formula I-B1, $R^2$ can be halo, lower alkyl sulfonyl, $R^{10}$—[$(CH_2)$y-W]z and $R^{13}$—$(CH_2)$t-U— where $R^{10}$, $R^{13}$, W, U, t, y and z are as defined above, and particularly those compounds where $R^2$ is sulphonyl methyl or $R^{10}$—[$(CH_2)$y-W]z where W is $SO_2$ and $R^{10}$, y and z are as defined above (compound I-B1(c)).

Among the embodiments of the compound of formula I-B2, $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B2(a)).

Among the embodiments of the compound of formula I-B2, $R^1$ can be hydrogen, halo, nitro, cyano or perfluoro lower alkyl, and particularly those compounds where $R^1$ is halo or hydrogen (compound I-B2(b)).

Among the embodiments of the compound of formula I-B2, $R^2$ can be halo, lower alkyl sulfonyl, $R^{10}$—[$(CH_2)$y-W]z and $R^{13}$—$(CH_2)$t-U— where $R^{10}$, $R^{13}$, W, U, t, y and z are as defined above, and particularly those compounds where $R^2$ is sulphonyl methyl or $R^{10}$—[$(CH_2)$y-W]z where W is $SO_2$ and $R^{10}$, y and z are as defined above (compound I-B2(c)).

Among the embodiments of the compound of formula I-B3, $R^3$ can be —$(CH_2)s$-V where s and V are as defined above, the preferred V substituent being a cycloalkyl group which contains from 3 to 8 carbon atoms, preferably cyclopentyl or cyclohexyl (compound I-B3(a)).

Among the embodiments of the compound of formula I-B3 are those compounds where $R^3$ is lower alkyl having from 2 to 6 carbon atoms, preferably lower alkyl residues being isobutyl or isopropyl (compound I-B3(b)).

Among the embodiments of the compound of formula I-B3, $R^1$ can be hydrogen, halo, nitro, cyano or perfluoro lower alkyl, and particularly those compounds where $R^1$ is halo or hydrogen (compound I-B3(c)).

Among the embodiments of the compound of formula I-B3, $R^2$ can be halo, lower alkyl sulfonyl, $R^{10}$—[$(CH2)$y-W]z and $R^{13}$—$(CH_2)$t-U— where $R^{10}$, $R^3$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above (compound I-B3(d)).

Among the embodiments of the compound of formula I-B4, $R^3$ can be —$(CH_2)s$-V where s and V are as defined above, the preferred V substituent being a cycloalkyl group which contains from 3 to 8 carbon atoms, preferably cyclopentyl or cyclohexyl (compound I-B4(a)).

Among the embodiments of the compound of formula I-B4 are those compounds where $R^3$ is lower alkyl having from 2 to 6 carbon atoms, preferably lower alkyl residues being isobutyl or isopropyl (compound I-B4(b)).

Among the embodiments of the compound of formula I-B4, $R^4$ is $R^7$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B4(c)).

Among the embodiments of the compound of formula I-B4, $R^2$ can be halo, lower alkyl sulfonyl, $R^{10}$—[$(CH_2)y$-W]z and $R^{13}$—$(CH_2)t$-U— where $R^{10}$, $R^{13}$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above (compound I-B4(d))

Among the embodiments of the compound of formula I-B5, $R^3$ can be —$(CH_2)s$-V where s and V are as defined above, the preferred V substituent being a cycloalkyl group which contains from 3 to 8 carbon atoms, preferably cyclopentyl or cyclohexyl (compound I-B5(a)).

Among the embodiments of the compound of formula I-B5 are those compounds where $R^3$ is lower alkyl having from 2 to 6 carbon atoms, preferably lower alkyl residues being isobutyl or isopropyl (compound I-B5(b)).

Among the embodiments of the compound of formula I-B5, $R^4$ is $R^7$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B5(c)).

Among the embodiments of the compound of formula I-B5, $R^1$ can be hydrogen, halo, nitro, cyano or perfluoro lower alkyl, and particularly those compounds where $R^1$ is halo or hydrogen (compound I-B5(d)).

Among the embodiments of the compound of formula I-B1(a), $R^1$ can be hydrogen, halo, nitro, cyano or perfluoro lower alkyl, and particularly those compounds where $R^1$ is halo or hydrogen (compound I-B1(a-1)).

Among the embodiments of the compound of formula I-B1(a), $R^2$ can be halo, lower alkyl sulfonyl, $R^{10}$—[$(CH_2)y$-W]z and $R^{13}$—$(CH_2)t$-U— where $R^{10}$, $R^{13}$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above (compound I-B1(a-2)).

Among the embodiments of the compound of formula I-B1(b), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B1(b-1)).

Among the embodiments of the compound of formula I-B1(b), $R^2$ can be halo, lower alkyl sulfonyl, $R^{10}$—[$(CH_2)y$-W]z and $R^{13}$—$(CH_2)t$-U— where $R^{10}$, $R^{13}$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above (compound I-B1(b-2)).

Among the embodiments of the compound of formula I-B1(c), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B1(c-1)).

Among the embodiments of the compound of formula I-B1(c), $R^1$ can be hydrogen, halo, nitro, cyano or perfluoro lower alkyl, and particularly those compounds where $R^1$ is halo or hydrogen (compound I-B1(c-2)).

Among the embodiments of the compound of formula I-B2(a), $R^1$ can be hydrogen, halo, nitro, cyano or perfluoro lower alkyl, and particularly those compounds where $R^1$ is halo or hydrogen (compound I-B2(a-1)).

Among the embodiments of the compound of formula I-B2(a), $R^2$ can be halo, lower alkyl sulfonyl, $R^{10}$—[$(CH_2)y$-W]z and $R^{13}$—$(CH_2)t$-U— where $R^{10}$, $R^{13}$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above (compound I-B2(a-2)).

Among the embodiments of the compound of formula I-B2(b), $R^4$ is $R^7$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B2(b-1)).

Among the embodiments of the compound of formula I-B2(b), $R^2$ can be halo, lower alkyl sulfonyl, $R^{10}$—[$(CH_2)y$-W]z and $R^{13}$—$(CH_2)t$-U— where $R^{10}$, $R^{13}$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above (compound I-B2(b-2)).

Among the embodiments of the compound of formula I-B2(c), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B2(c-1)).

Among the embodiments of the compound of formula I-B2(c), $R^1$ can be hydrogen, halo, nitro, cyano or perfluoro lower alkyl, and particularly those compounds where $R^1$ is halo or hydrogen (compound I-B2(c-2)).

Among the embodiments of the compound of formula I-B3(a), $R^1$ can be hydrogen, halo, nitro, cyano or perfluoro lower alkyl, and particularly those compounds where $R^1$ is halo or hydrogen (compound I-B3(a-1)).

Among the embodiments of the compound of formula I-B3(a), $R^2$ can be halo, lower alkyl sulfonyl, $R^{10}$—[$(CH_2)y$-W]z and $R^{13}$—$(CH_2)t$-U— where $R^{10}$, $R^{13}$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above (I-B3(a-2)).

Among the embodiments of the compound of formula I-B3(b), $R^1$ can be hydrogen, halo, nitro, cyano or perfluoro lower alkyl, and particularly those compounds where $R^1$ is halo or hydrogen (compound I-B3(b-1)).

Among the embodiments of the compound of formula I-B3(b), $R^2$ can be halo, lower alkyl sulfonyl, $R^{10}$—[$(CH_2)y$-W]z and $R^{13}$—$(CH_2)t$-U— where $R^{10}$, $R^{13}$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above (compound I-B3(b-2)).

Among the embodiments of the compound of formula I-B3(c), $R^3$ can be —$(CH_2)s$-V where s and V are as defined above, the preferred V substituent being a cycloalkyl group which contains from 3 to 8 carbon atoms, preferably cyclopentyl or cyclohexyl (compound I-B3(c-1)).

Among the embodiments of the compound of formula I-B3(c) are those compounds where $R^3$ is lower alkyl having from 2 to 6 carbon atoms, preferably lower alkyl residues being isobutyl or isopropyl (compound I-B3(c-2)).

Among the embodiments of the compound of formula I-B3(c), $R^2$ can be halo, lower alkyl sulfonyl, $R^{10}$—[$(CH_2)y$-W]z and $R^{13}$—$(CH_2)t$-U— where $R^{10}$, $R^{13}$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above (compound I-B3(c-3)).

Among the embodiments of the compound of formula I-B3(d), $R^3$ can be —$CH_2$)s-V where s and V are as defined above, the preferred V substituent being a cycloalkyl group which contains from 3 to 8 carbon atoms, preferably cyclopentyl or cyclohexyl (compound I-B3(d-1)).

Among the embodiments of the compound of formula I-B3(d) are those compounds where $R^3$ is lower alkyl having from 2 to 6 carbon atoms, preferably lower alkyl residues being isobutyl or isopropyl (compound I-B3(d-2)).

Among the embodiments of the compound of formula I-B3(d) $R^1$ can be hydrogen, halo, nitro, cyano or perfluoro lower alkyl, and particularly those compounds where $R^1$ is halo or hydrogen (compound I-B3(d-3)).

Among the embodiments of the compound of formula I-B4(a), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B4(a-1)).

Among the embodiments of the compound of formula I-B4(a), $R^2$ can be halo, lower alkyl sulfonyl, $R^{10}$—[$(CH_2)y$-W]z and $R^{13}$—$(CH_2)t$-U— where $R^{10}$, $R^{13}$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above (compound I-B4(a-2)).

Among the embodiments of the compound of formula I-B4(b), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B4(b-1)).

Among the embodiments of the compound of formula I-B4(b), $R^2$ can be halo, lower alkyl sulfonyl, $R^{10}$—[$(CH_2)y$-W]z and $R^{13}$—$(CH_2)t$-U— where $R^{10}$, $R^{13}$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above (compound I-B4(b-2)).

Among the embodiments of the compound of formula I-B4(c), $R^3$ can be —$CH_2$)s-V where s and V are as defined above, the preferred V substituent being a cycloalkyl group which contains from 3 to 8 carbon atoms, preferably cyclopentyl or cyclohexyl (compound I-B4(c-1)).

Among the embodiments of the compound of formula I-B4(c) are those compounds where $R^3$ lower alkyl having from 2 to 6 carbon atoms, preferably lower alkyl residues being isobutyl or isopropyl (compound I-B4(c-2)).

Among the embodiments of the compound of formula I-B4(c), $R^2$ can be halo, lower alkyl sulfonyl, $R^{10}$—[$(CH_2)y$-W]z and $R^{13}$—$(CH_2)t$-U— where $R^{10}$, $R^{13}$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above (compound I-B4(c-3)).

Among the embodiments of the compound of formula I-B4(d), $R^3$ can be —$CH_2$)s-V where s and V are as defined above, the preferred V substituent being a cycloalkyl group which contains from 3 to 8 carbon atoms, preferably cyclopentyl or cyclohexyl (compound I-B4(d-1)).

Among the embodiments of the compound of formula I-B4(d) are those compounds where $R^3$ is lower alkyl having from 2 to 6 carbon atoms, preferably lower alkyl residues being isobutyl or isopropyl (compound I-B4(d-2)).

Among the embodiments of the compound of formula I-B4(d), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B4(d-3)).

Among the embodiments of the compound of formula I-B5(a), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B5(a-1)).

Among the embodiments of the compound of formula I-B5(a) $R^1$ can be hydrogen, halo, nitro, cyano or perfluoro lower alkyl, and particularly those compounds where $R^1$ is halo or hydrogen (compound I-B5(a-2)).

Among the embodiments of the compound of formula I-B5(b), $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B5(b-1)).

Among the embodiments of the compound of formula I-B5(b) $R^1$ can be hydrogen, halo, nitro, cyano or perfluoro lower alkyl, and particularly those compounds where $R^1$ is halo or hydrogen (compound I-B5(b-2)).

Among the embodiments of the compound of formula I-B5(c), $R^3$ can be —$CH_2$)s-V where s and V are as defined above, the preferred V substituent being a cycloalkyl group which contains from 3 to 8 carbon atoms, preferably cyclopentyl or cyclohexyl (compound I-B5(c-1)).

Among the embodiments of the compound of formula I-B5(c) are those compounds where $R^3$ is lower alkyl having from 2 to 6 carbon atoms, preferably lower alkyl residues being isobutyl or isopropyl (compound I-B5(c-2)).

Among the embodiments of the compound of formula I-B5(c) $R^1$ can be hydrogen, halo, nitro, cyano or perfluoro lower alkyl, and particularly those compounds where $R^1$ is halo or hydrogen (compound I-B5(c-3)).

Among the embodiments of the compound of formula I-B5(d), $R^3$ can be —$CH_2$)s-V where s and V are as defined above, the preferred V substituent being a cycloalkyl group which contains from 3 to 8 carbon atoms, preferably cyclopentyl or cyclohexyl (compound I-B5(d-1)).

Among the embodiments of the compound of formula I-B5(d) are those compounds where $R^3$ is lower alkyl having from 2 to 6 carbon atoms, preferably lower alkyl residues being isobutyl or isopropyl (compound I-B5(d-2)).

Among the embodiments of the compound of formula I-B5(d) $R^4$ is $R^{17}$, which can be an unsubstituted, mono- or di-substituted thiazole, imidazole, oxazole, thiadiazole, pyridine, pyrimidine, pyrazine, pyridazine, or triazine ring, and particularly those compounds where $R^{17}$ is a thiazole or pyridine ring (compound I-B5(d-3)).

Among the embodiments of the compound of formula I-B3(a-1), $R^2$ can be halo, lower alkyl sulfonyl, $R^{10}$—[$(CH_2)y$-W]z and $R^{13}$—$(CH_2)t$-U— where $R^{10}$, $R^{13}$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above.

Among the embodiments of the compound of formula I-B3(b-1), $R^2$ can be halo, lower alkyl sulfonyl, $R^{10}$—[$(CH_2)y$-W]z and $R^{13}$—$(CH_2)t$-U— where $R^{10}$, $R^{13}$, W, U, t, y and z are as defined above, and particularly those compounds where $R^2$ is sulphonyl methyl or $R^{10}$—[$(CH_2)y$-W]z where W is $SO_2$ and $R^{10}$, y and z are as defined above.

The compounds of the present invention may be prepared as is shown in the following reaction schemes.

The corresponding alkyl iodides $R^3$—I were reacted with an propargylic ester to give the substituted 2-iodo alkenoates II (see Y. Ichinose et al., Tet. Lett. 1989, 24, 3155). Alternatively, compounds where M equals hydrogen, can be prepared by reacting aldehydes $R^3$—CHO with an appropriate Wittig reagent, preferably triethyl phoshono acetate, to give the acrylic esters which then are converted into the 2-halo-alkenoates II (M=H) by a halogenation/dehydrohalogenation procedure known in the art. Subsequent Pd(0)-catalyzed cross coupling with (hetero)aromatic boronic acids or boronic esters yield the (hetero)aryl-substituted alkenoates of formula III. In addition, reacting appropriately substituted (hetero)aryl bromides or iodides with vinylic boronic esters, which can also prepared in situ, also lead to the formation of compounds of formula III. For the preparation of compounds of formula III where M equals halo, the (hetero)aryl substituted α-keto ester may be reacted with the appropriate halo-substituted organophosphonate using conditions known in the art. For the synthesis of substituted cyclopropanes (compounds with the formula VII, Rx and Ry not being hydrogen), alkenoates III are reacted with in situ generated carbenes under conditions known in the art. For the generation of unsubstituted cyclopropanes of formula V, alkenoates III can be reduced to the corresponding allylic alcohols of formula IV using aluminium hydride reagents, preferably diisobutyl aluminium hydride. Subsequent cyclopropanation is achieved by a Simmons-Smith-like procedure to yield compounds of the formula V. To obtain pure enantiomers, the racemic mixture can be resolved using methodology known in the art. Oxidation, preferably using chromium VI reagents, like Jones reagent, yields the corresponding carboxylic acids of formula VI. In order to prepare amides of formula XI, acids VI are activated by known means in the area of peptide coupling, and subsequently reacted with amines $R^{17}$—$NH_2$. For the synthesis of amides of the formula XII, the acids VI are reacted with substituted ureas $H_2N$—CO—NH—$R^{16}$ to give the amides. Esters of formula VII are reacted with deprotonated amines $R^{17}$—$NH_2$, using appropriate Grignard reagents, preferably isobutyl magnesium chloride, to yield the amides of formula IX. For the preparation of amides of formula X, esters VII are hydrolyzed and treated in an analogous fashion as mentioned for the synthesis of amides XI.

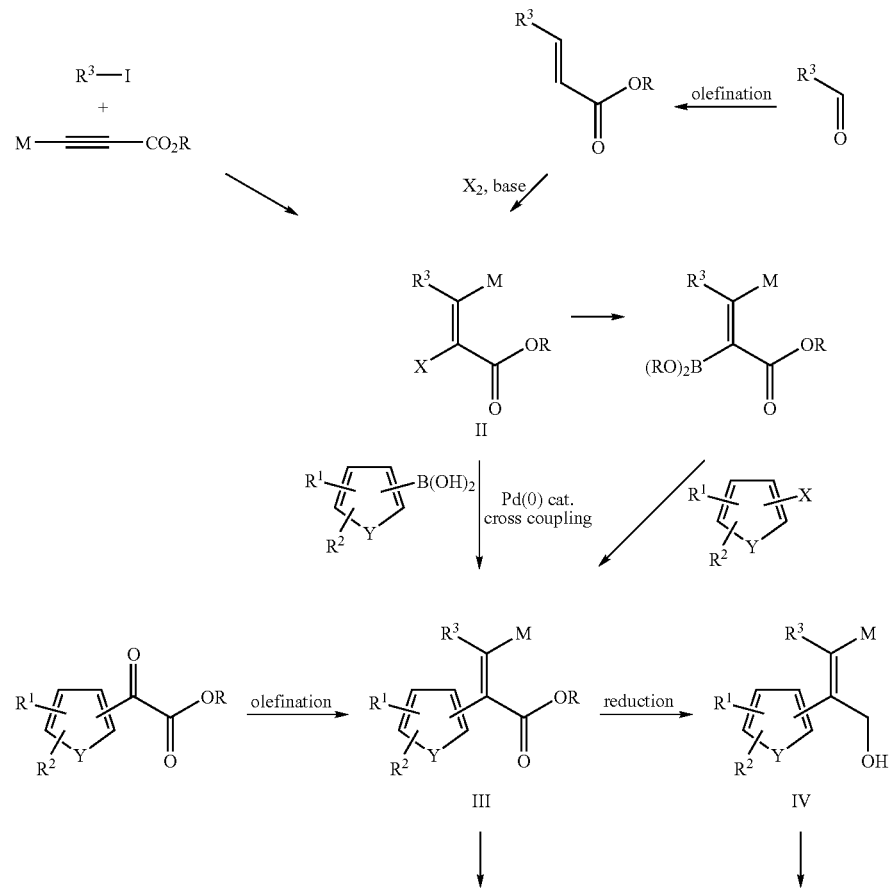

Scheme I

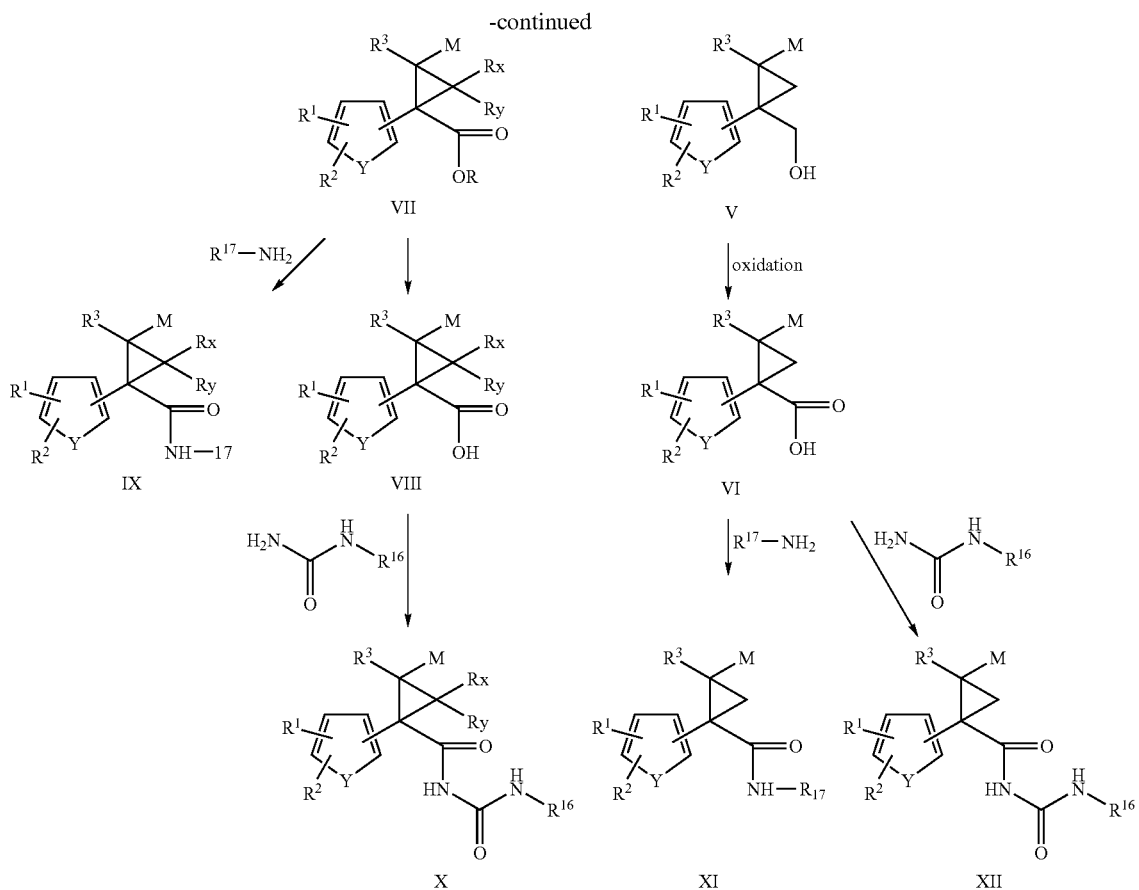

General Procedures:

All water-or air-sensitive reactions were conducted in dry solvents under an inert atmosphere. Nuclear magnetic resonance (NMR) spectra were obtained on Bruker Avance DPX 300, 5 mm QNP and Varian Inova 500, 5 mm indirect detection instruments. Mass spectra (MS) were obtained on a Agilent 1100 MSD spectrometer operating in electrospray mode or on a Agilent 5973N GC-MSD.

List of abbreviations:

| | |
|---|---|
| LHMDS | lithium bis(trimethylsilyl)amide |
| THF | tetrahydrofuran |
| DIBAL | diisobutylaluminumhydride |
| TBTU | O-benzotriazol-1-yl-N,N,N',N'tetra-methyluroniumtetrafluoroborate |
| HATU | O-(7-Aza-1-benzotriazolyl)-N,N,N',N'-tetramethyluroniumhexafluorophosphate |
| DMF | N,N-dimethylformamide |
| NMP | 1-methyl-2-pyrrolidinone |
| brine | saturated aqueous sodium chloride solution |
| r.t. | room temperature/ambient temperature |
| TBME | 2-methoxy-2-methyl-propane |
| DMA | N,N-dimethyl-acetamide |
| HPLC | high pressure liquid chromatography |
| TFA | trifluoroacetic acid |
| $NH_3$ | ammonia |
| PL-EDC | polymer supported 1-ethyl-3-(3-dimethylaminopropyl)-carbodiimide resin |
| PL-EDA | polymer supported ethylenediamine resin |
| DETA resin | diethylenetriamine resin |

-continued

List of abbreviations:

| | |
|---|---|
| HOAt | 1-hydroxy-7-azabenzotriazole |
| m | multiplet |
| mc | multiplet centered |
| s | singlet |
| bs | broad singlet |

General Procedure Ia for the Preparation of Substituted 2-bromo alkenoates via Wittig-Horner-Emmons:

Add triethyl phosphonoacetate (1.1 equiv.) in THF (0.2 ml/1.0 mmol) to potassium tert-butoxide (1.1 equiv.) in THF (1.5 ml/1.0 mmol) at −78° C. and stir. After 30 minutes, add aldehyde (1.0 mmol) in THF (0.2 ml/1.0 mmol) at −78° C. and allow the reaction to gradually warm to ambient temperature. After stirring 18 hours, treat the reaction mixture with water and extract with ethyl acetate. Combine the organic layers and wash with saturated aqueous sodium chloride, dry over magnesium sulfate and concentrate under reduced pressure. Dissolve the residue in dichloromethane (1.6 ml/1.0 mmol) and add bromine (1.1 equiv. to alkene) in carbon tetrachloride (0.3 ml/1.0 mmol) at −10° C. and stir. After 2 hours add triethylamine (1.2 equiv. to alkene) in dichloromethane (0.4 ml/1.0 mmol) at −10° C. and allow the reaction to gradually warm to ambient temperature. After stirring 18 hours treat the reaction mixture with 1N hydrochloric acid and extract with dichloromethane. Combine the organic layers and wash with saturated aqueous sodium bicarbonate, saturated sodium chloride, dry over magnesium sulfate and concentrate under reduced pressure. Purification by bulb-to-bulb distillation.

The following compounds are prepared according to the method of the General Procedure Ia as using the indicated starting material.
(Z)-Ethyl 2-bromo-3-cyclohexyl-prop-2-enoate,
aldehyde used: cyclohexane carboxaldehyde
(Z)-Ethyl 2-bromo-4-methyl-pent-2-enoate,
aldehyde used: isobutyraldehyde General Procedure Ib for the preparation of substituted 2-iodo-alk-2-enoates via triethyl borane-induced radical reaction:

The alkyl iodides mentioned below were reacted with ethyl propiolate in the presence of triethylborane as described (Y. Ichinose et al., Tet. Lett. 1989, 30(24), 3155-31-58).
(Z)-Ethyl 3-cyclohexyl-2-iodo-propenoate, MS(EI), $M^+=308$,
reagent used: cyclohexyl iodide
(Z)-Ethyl 3-cyclopentyl-2-iodo-propenoate, MS(EI), $M^+=294$,
reagent used: cyclopentyl iodide
(Z)-Ethyl 2-iodo-4-methyl-pent-2-enoate, MS(EI), $M^+=268$,
reagent used: 2-iodo-propane General Procedure IIa for the Preparation of Intermediates of Formula III:

Add the aromatic boronic acid (1.2 equiv. to vinyl halide) to a stirred mixture of vinyl halide, palladium catalyst (5 mol%) and potassium carbonate (2.5 equiv) in toluene (3 ml/1.0 mmol vinyl halide) and heat the mixture at 70° C. for 14 h. Subsequently filter the mixture, add water and extract with MTB ether. Combine the organic layers, dry over sodium sulfate and concentrate under reduced pressure.

General Procedure IIb for the Preparation of Intermediates of Formula III:

Add the aromatic boronic acid (1.1 equiv. to vinyl halide) to a mixture of vinyl halide (1.0 mmol), tetrakis(triphenylphosphine)palladium (0) (0.1 equiv. to vinyl halide) and 2M aqueous sodium carbonate (2 equiv. to vinyl halide) in toluene (4 ml/1.0 mmol) and isopropanol (1 ml/1.0 mmol) at ambient temperature. Allow the reaction mixture to gradually warm to 70° C. and stir. After 18 hours, treat the reaction with water and extract with ethyl acetate. Combine the organic layers and wash with saturated aqueous sodium chloride, dry over magnesium sulfate and concentrate under reduced pressure. Purification by flash chromatography eluting with the indicated mixture of hexanes:ethyl acetate gives the product.

General Procedure IIIa for Oxidation of Sulfides

Add m-chloro perbenzoic acid (2.2 equiv.) to thioether (1.0 mmol) in dichloromethane (10 ml/1.0 mmol) at ambient temperature and stir. After 1 hour treat with saturated aqueous sodium bicarbonate and extract with dichloromethane. Combine the organic layers, dry over magnesium sulfate and concentrate under reduced pressure. Purification by flash chromatography, eluting with the indicated mixture of hexanes: ethyl acetate gives the products.

General Procedure IIIb for Oxidation of Sulfides

Add a suspension of oxone® (2.2 equiv.) in water (6.0 mL/1.0 mmol) to a solution of thioether (1.0 mmol) in acetone (10 mL/1.0 mmol). Stir for three h, and then add water. Extract the resulting mixture with dichloromethane. Combine the extracts, wash them with saturated aqueous sodium chloride solution, dry them over magnesium sulfate, and remove solvent under vacuum. Apply the residue to silica gel column, eluting with the indicated mixture of hexanes:ethyl acetate to obtain the product.

General Procedure IV for Reduction of Alkenoates

Add diisobutyl aluminium hydride solution (20% in toluene, 2.2 equiv. to ester) to ester (2.0 mmol) in THF (15 ml) at −78° C. and allow the reaction mixture to gradually warm to ambient temperature. After 2 hours, add methanol and concentrate under reduced pressure. Treat the reaction mixture with saturated aqueous Rochelle salt and ethyl acetate and stir. After 15 minutes, separate the phases and extract with ethyl acetate. Combine the organic layers, dry over magnesium sulfate and concentrate under reduced pressure to give the alcohols. Use without purification for the next step.

General Procedure V for the Cyclopropanation of Allylic Alcohols

Add diethylzinc solution 1.0 M in hexanes (5.0 equiv. to alcohol) to alcohol (2.0 mmol) in THF (30 ml/1.0 mmol) at ambient temperature. Allow the reaction mixture to gradually warm to 60° C. and add slowly diiodomethane (10,0 equiv. to alcohol) and stir. After 18 hours, treat the reaction mixture with IN hydrochloric acid and extract with diethyl ether. Combine the organic layers and wash with saturated aqueous sodium bicarbonate, saturated sodium chloride, dry over magnesium sulfate and concentrate under reduced pressure. Purification by flash chromatography, eluting with the indicated mixture of hexanes:ethyl acetate gives the products.

General Procedure VI for Jones Oxidation of Alcohols

Add concentrated sulfuric acid (1,15 ml) to a solution of chromium (VI) oxide (1.34 g, 13.4 mmol) in 2 ml of water at 0° C. and dilute with more water until the total volume is 5 ml. Add 2.0 ml of this solution to alcohol (1.0 mmol) in acetone (20.0 ml/1.0 mmol) at 0° C. and allow the reaction mixture to gradually warm to ambient temperature. After 2 hours, add isopropanol (0.45 ml/1.0 mmol) and stir. After 30 minutes treat the reaction with water and extract with diethyl ether. Combine the organic layers and wash with saturated sodium chloride, dry over magnesium sulfate and concentrate under reduced pressure to give the title compound. Use without purification for the next step.

General Procedure VIIa for Amidation

Add 2-aminothiazole (1.1 equiv. to acid) to a mixture of cyclopropyl carboxylic acid (1.0 mmol), TBTU (1. 1 equiv. to acid) and triethylamine (2.0 equiv. to acid) in THF (5 ml/1.0 mmol) at ambient temperature and stir. After 18 hours, add 1N hydrochloric acid and extract with diethyl ether. Combine the organic layers and wash with saturated sodium chloride, dry over magnesium sulfate and concentrate under reduced pressure. Purification by flash chromatography, eluting with the indicated mixture of hexanes:ethyl acetate gives the amides.

General Procedure VIIb for Amidation

Add oxalyl chloride (1.5 equiv. to acid) to dimethylformamide (1.6 equiv. to acid) THF (8 ml/1.0 mmol) at −20 ° C., allow the reaction mixture to gradually warm to ambient temperature and stir. After 15 minutes, cool to −30° C. and add acid (1.0 mmol) in THF (8 ml/1.0 mmol), allow the reaction mixture to gradually warm to ambient temperature and stir. After 1 h, cool to −50° C. and add a mixture of 2-amino-thiazole (3.2 equiv. to acid) and triethylamine (3.2 equiv. to acid) in THF (2.5 ml/1.0 mmol), allow the reaction mixture to gradually warm to ambient temperature and stir. After 5h treat the reaction with 1N hydrochloric acid and extract with diethyl ether. Combine the organic layers and wash with saturated aqueous sodium bicarbonate, saturated sodium chloride, dry over magnesium sulfate and concentrate under reduced pressure. Purification by flash chromatography, eluting with the indicated mixture of hexanes:ethyl acetate gives the amides.

EXAMPLE 1

(±)-(E)-2-Cyclohexyl-1-(4-methanesulfonyl-phenyl)-cyclopropanecarboxylic acid (5-chloro-thiazol-2-yl)-amide

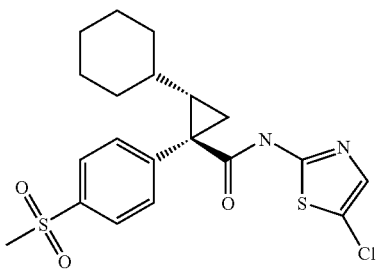

Dissolve (±)-(E)-2-cyclohexyl-1-(4-methylsulfamoyl-phenyl)-cyclopropanecarboxylic acid (90 mg, 0.267 mmol) in 2.2 mL THF, add TBTU (94 mg, 0.29 mmol) and triethylamine (0.13 mL, 1.06 mmol) and stir for 10 minutes at r.t. Add hydrochloric salt of 5-chloro-thiazol-2-ylamine (51.7 mg, 0.29 mmol) and stir over night at r.t. Dilute the mixture with ethyl acetate and wash with 1 N hydrochloric acid. Separate the organic layer and wash with saturated aqueous sodium bicarbonate solution, followed by saturated sodium chloride solution. Filter through a hydrophobic filter paper and remove the solvent under vacuum. Then purify this material further via column chromatography on silica gel, eluting with a gradient from 100:0 to 0:100 hexanes:TBME to afford the title compound as amorphous solid (14.0 mg). $^1$H-NMR (CDCl$_3$) δ=0.17-0.34 (m, 1H), 0.81-1.34 (m, 7H), 1.49-1.70 (m, 3H), 1.71-1.79 (m, 2H), 2.00-2.12 (m, 1H), 3.16 (s, 3H), 7.18 (s, 1H), 7.58-7.67 (m, 2H), 7.99-8.08 (m, 2H), 8.21-8.34 (bs, 1H). MS(m/e): 439/441 (M+H).

EXAMPLE 2

(±)-(E)-2-Cyclohexylmethyl-1-(4-methanesulfonyl-phenyl)-cyclopropanecarboxylic acid thiazol-2-ylamide

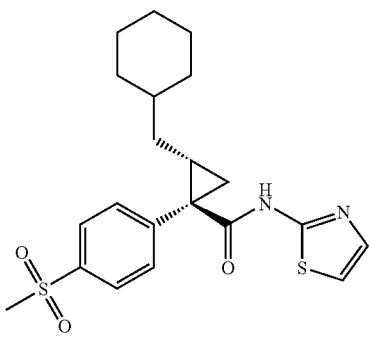

a: (E)-4-Cyclohexyl-2-(4-methylsulfanyl-phenyl)-but-2-enoic acid ethyl ester

Add potassium-tert.-butoxide (4.3 mL, 1.0 M in THF, 4.3 mmol) to a suspension of (2-cyclohexyl-ethyl)-triphenyl-phosphonium iodide (2.15 g, 4.3 mmol) at room temperature and stir the reaction mixture for 1 h. Dissolve (4-methylsulfanyl-phenyl)-oxo-acetic acid ethyl ester (prepared as described by I. T. Barnish et. al. *J. Med. Chem.* 1981, 24, 399-404) in THF and add the resulting solution to the reaction mixture. Stir at room temperature over night. Evaporate the solvent and add 15 mL hexane to the remaining solid. Stir at 40° C. for 30 minutes, filter and concentrate the filtrate under vacuum to afford 1.3 g raw material as a yellow oil. Further purify this material via silica gel chromatography, eluting with a gradient from 98:2 to 90:10 hexane:ethyl acetate to afford a colorless oil (379 mg).

MS (m/e): 319 (M+H).

b: (2-Iodo-ethyl)-cyclohexane

Dissolve (2-bromo-ethyl)-cyclohexane (10.0 g, 52.3 mmol) in 500 mL acetone, add sodium iodide (15.6 g, 104.6 mmol) and reflux over night. Filter the reaction mixture, add water to the filtrate and extract with hexane. Dry the organic phases over sodium sulfate, filter and concentrate to an oil. Further purify this material by distillation to afford the title compound (10.6 g). $^1$H-NMR (CDCl$_3$) δ=0.83-1.00 (m, 2H), 1.07-1.48 (m, 4H), 1.61-1.80 (m, 7H), 3.16-3.27 (m, 2H).

c: (2-Cyclohexyl-ethyl)-triphenyl-phosphonium iodide

Dissolve (2-iodo-ethyl)-cyclohexane (3.0 g, 12.5 mmol) in toluene, add triphenyl-phosphine (3.1 g, 11.9 mmol) and stir at 80° C. over night. Cool the reaction mixture down to room temperature and isolate the product by filtration as a white solid (4.75 g). $^1$H-NMR (CDCl$_3$) δ=0.78-0.96 (m, 2H), 1.01-1.34 (m, 3H), 1.44-1.74 (m, 2H), 3.56-3.70 (m, 2H), 7.66-7.90 (m, 15H).

d: (E)-4-Cyclohexyl-2-(4-methanesulfonyl-phenyl)-but-2-enoic acid ethyl ester

Following the method of example 54d, using (E)-4-cyclohexyl-2-(4-methylsulfanyl-phenyl)-but-2-enoic acid ethyl ester (978 mg, 3.07 mmol) dissolved in methanol 5 h at ambient temperature after the addition of oxone® (2.45 g, 3.99 mmol) gives the title compound as an yellow oil (1.02 g). MS (m/e): 351 (M+H).

e: (E)-4-Cyclohexyl-2-(4-methanesulfonyl-phenyl)-but-2-en-1-ol

Following the method of example 54e, using (E)-4-cyclohexyl-2-(4-methanesulfonyl-phenyl)-but-2-enoic acid ethyl ester (956 mg, 2.73 mmol) and 3 h at ambient temperature after the addition of DIBAL in toluene (4.95 mL, 6.0 mmol) gives the title compound as an amorphous solid (666 mg). MS (m/e): 291 ([M–H$_2$O]+H).

f: (±)-(E)-[2-Cyclohexylmethyl-1-(4-methanesulfonyl-phenyl)-cyclopropyl]-methanol Following the method of example 54f, using (E)-4-cyclohexyl-2-(4-methanesulfonyl-phenyl)-but-2-en-1-ol (666 mg, 2.16 mmol) and 18 h at 60° C. after the addition of diethylzinc in toluene (7.8 mL, 8.63 mmol) and diiodomethane (1.39 mL, 17.28 mmol) affords the title compound as an amorphous solid (518 mg). MS (m/e): 305 ([M–H$_2$O]+H).

g: (±)-(E)-2-Cyclohexylmethyl-1-(4-methanesulfonyl-phenyl)-cyclopropanecarboxylic acid Following the method of example 54 g, using (±)-(E)-[2-cyclohexylmethyl-1-(4-methanesulfonyl-phenyl)-cyclopropyl]-methanol (518 mg, 1.6 mmol) and 3 h at 0° C. after the addition of the chromium oxide (633 mg, 6.33 mmol) gives the title compound as a white solid (188 mg). MS (m/e): 291 ([M-$CO_2$]—H).

h: (±)-(E)-2-Cyclohexylmethyl-1-(4-methanesulfonyl-phenyl)-cyclopropanecarboxylic acid thiazol-2-ylamide Dissolve (±)-(E)-2-cyclohexylmethyl-1-(4-methanesulfonyl-phenyl)-cyclopropanecarboxylic acid (188 mg, 0.56 mmol) in 5 mL THF, add TBTU (197 mg, 0.613 mmol) and triethylamine (0.16 mL, 1.11 mmol) and stir for 10 minutes at room temperature. Dissolve 2-aminothiazole (61.0 mg, 0.61 mmol) in 1.0 mL THF and add the resulting solution to the reaction mixture. Stir over night at room temperature. Evaporate the solvent under vacuum and purify the resulting solid by silica gel column chromatography. Eluting with a gradient from 100 dichlormethane to 95:5 dichloromethane:methanol and subsequent recrystallization from diethyl ether affords the title compound as white crystals (80.0 mg). $^1$H-NMR (d$_6$-DMSO) δ=0.15-0.31 (m, 1H), 0.73-0.91 (m, 2H), 0.97-1.39 (m, 6H), 1.52-1.74 (m, 6H), 1.90-2.04 (m, 1H), 3.2-3.25 (s, 3H), 6.91-6.95 (m, 1H), 7.17-7.20 (m, 1H), 7.35-7.41 (m, 2H), 7.63-7.69 (m, 2H), 11.43-11.56 (m, 1H). MS (m/e): 419 (M+H).

EXAMPLE 3

(±)-(E)-2-Isobutyl-1-(4-methanesulfonyl-phenyl)-cyclopropanecarboxylic acid thiazol-2-ylamide

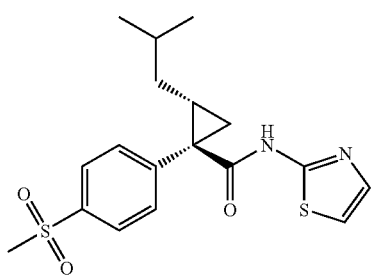

a: (E)-5-Methyl-2-(4-methylsulfanyl-phenyl)-hex-2-enoic acid ethyl ester

Wittig olefination of (3-methyl-butyl)-triphenyl-phosphonium bromide (2.6 g, 6.28 mmol) following the method of 2a affords the title compound as a colorless oil (841 mg). MS (m/e): 279 (M+H).

b: (3-Methyl-butyl)-triphenyl-phosphonium bromide

Reaction of 3-methylbutylbromide (6.4 g, 42.0 mmol) with triphenylphosphine (10.0 g, 40.0 mmol) following the procedure of 2c affords the title compound as a white solid (2.6 g). MS (m/e): 335 (M+H).

c: (E)-2-(4-Methanesulfonyl-phenyl)-5-methyl-hex-2-enoic acid ethyl ester

Following the method of example 54d, oxidation of (E)-5-methyl-2-(4-methylsulfanyl-phenyl)-hex-2-enoic acid ethyl ester (840 mg, 3.01 mmol) with oxone® (2.4 g, 3.9 mmol) in methanol gives the title compound as a yellow oil (848 mg). MS (m/e): 311 (M+H).

d: (E)-2-(4-Methanesulfonyl-phenyl)-5-methyl-hex-2-en-1-ol

Reduction of (E)-2-Isobutyl-1-(4-methanesulfonyl-phenyl)-5-methyl-hex-2-enoic acid ethyl ester (840 mg, 2.71 mmol) with DIBAL in toluene (4.9 mL, 5.95 mmol) following the method of example 54e gives the title compound as an amorphous solid (615 mg). MS (m/e): 251 ([M–$H_2O$]+H).

e: (±)-(E)-[2-Isobutyl-1-(4-methanesulfonyl-phenyl)-cyclopropyl]-methanol

Following the method of example 54f, reaction of (E)-2-(4-methanesulfonyl-phenyl)-5-methyl-hex-2-en-1-ol (615 mg, 2.29 mmol), diethylzinc in toluene (8.3 mL, 9.16 mmol), and diiodomethane (1.5 mL, 18.32 mmol) for 18 h at 60° C. affords the title compound as an amorphous solid (280 mg). MS (m/e): 265 ([M–$H_2O$]+H).

f: (±)-(E)-2-Isobutyl-1-(4-methanesulfonyl-phenyl)-cyclopropanecarboxylic acid Oxidation of (±)-(E)-[2-isobutyl-1-(4-methanesulfonyl-phenyl)-cyclopropyl]-methanol (280 mg, 0.99 mmol) with chromium oxide (399 mg, 3.99 mmol), following the method of example 54g, gives the title compound as a white solid (158 mg).

MS (m/e): 251 ([M-$CO_2$]—H).

g: (±)-(E)-2-Isobutyl-1-(4-methanesulfonyl-phenyl)-cyclopropanecarboxylic acid thiazol-2-ylamide Add TBTU (188 mg, 0.58 mmol) and triethylamine (0.15 mL, 1.07 mmol) to a solution of (±)-(E)-2-isobutyl-1-(4-methanesulfonyl-phenyl)-cyclopropanecarboxylic acid (158 mg, 0.54 mmol) in 4 mL THF and stir the remaining mixture for 5 minutes at room temperature. Then add a solution of 2-aminothiazole (58.7 mg, 0.58 mmol) in 1.0 mL THF, and stir overnight at room temperature. Evaporate the solvent under vacuum and purify the resulting solid by silica gel column chromatography. Elution with a gradient from 100% dichlormethane to 5% methanol in dichlormethane and subsequent recrystallization from hexane/ethylacetate affords the title compound as a white solid (67 mg). $^1$H-NMR (d$_6$-DMSO) δ=0.12-0.26 (m, 1H), 0.84-0.93 (m, 6H), 1.17-1.24 (m, 1H), 1.37-1.47 (m, 1H), 1.54-1.77 (m, 1H), 1.90-1.98 (s, 1H), 2.15-2.27 (m, 1H), 3.14-3.19 (m, 3H), 6.93-6.97 (m, 1H), 7.33-7.37 (m, 1H), 7.56-7.64 (m, 2H), 8.00-8.07 (m, 2H), 8.26-8.47 (m, 1H). MS (m/e): 379 (M+H).

EXAMPLE 4

(±)-(E)-1-(4-Methanesulfonyl-phenyl)-2-(3-methyl-butyl)-cyclopropanecarboxylic acid thiazol-2-ylamide

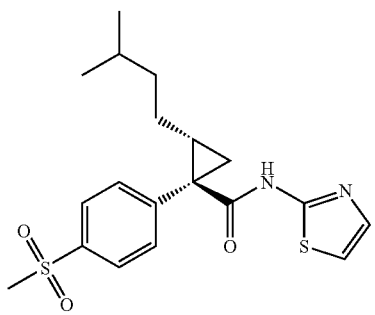

a: (E)-6-Methyl-2-(4-methylsulfanyl-phenyl)-hept-2-enoic acid ethyl ester

Wittig olefination of (4-methyl-pentyl)-triphenylphosphonium bromide (3.37 g, 7.88 mmol) following the method of 2a affords the title compound as a colorless oil (320 mg). MS (m/e): 293 (M+H).

b: (4-Methyl-pentyl)-triphenylphosphonium bromide

Reaction of 1-bromo-3,3-dimethylbutane (5 g, 30 mmol) with triphenylphosphine (7.4 g, 28 mmol) following the procedure of 2c affords the title compound as a white solid (3.4 g). MS (m/e): 347 (M+H).

c: (E)-2-(4-Methanesulfonyl-phenyl)-6-methyl-hept-2-enoic acid ethyl ester

Following the method of example 54d, oxidation of 6-methyl-2-(4-methylsulfanyl-phenyl)-hept-2-enoic acid ethyl ester (320 mg, 1.09 mmol) with oxone® (0.87 mg, 1.4 mmol) in methanol gives the title compound as a yellow oil (327 mg). MS (m/e): 325 (M+H).

d: (E)-2-(4-Methanesulfonyl-phenyl)-6-methyl-hept-2-en-1-ol

Reduction of (E)-2-(4-methanesulfonyl-phenyl)-6-methyl-hept-2-enoic acid ethyl ester (320 mg, 1.09 mmol) with DIBAL in toluene (1.98 mL, 2.4 mmol) following the method of example 54e gives the title compound as an amorphous solid (275 mg). MS (m/e): 283 (M+H).

e: (±)-(E)-[1-(4-Methanesulfonyl-phenyl)-2-(3-methyl-butyl)-cyclopropyl]-methanol Following the method of example 54f, reaction of (E)-2-(4-methanesulfonyl-phenyl)-5-methyl-hex-2-en-1-ol (270 mg, 0.95 mmol), diethylzinc in toluene (3.79 mL, 3.8 mmol), and diiodomethane (0.61 mL, 7.6 mmol) for 18 h at 60° C. affords the title compound as an amorphous solid (114 mg). MS (m/e): 297 (M+H).

f: (±)-(E)-1-(4-Methanesulfonyl-phenyl)-2-(3-methyl-butyl)-cyclopropanecarboxylic acid Oxidation of (±)-(E)-[1-(4-methanesulfonyl-phenyl)-2-(3-methyl-butyl)-cyclopropyl]-methanol (110 mg, 0.38 mmol) with chromium oxide (151 mg, 1.51 mmol), following the method of example 54g, gives the title compound as a white solid (109 mg). MS (m/e): 311 (M+H).

g: (±)-(E)-1-(4-Methanesulfonyl-phenyl)-2-(3-methyl-butyl)-cyclopropanecarboxylic acid thiazol-2-ylamide Following the method of example 2h, reaction of 1-(4-methanesulfonyl-phenyl)-2-(3-methyl-butyl)-cyclopropanecarboxylic acid (100 mg, 0.32 mmol) with TBTU (111 mg, 0.35 mmol), triethylamine (0.089 mL, 0.644 mmol) and 2-aminothiazole (35.0 mg, 0.35 mmol) affords the title compound as white crystals (23.0 mg). $^1$H-NMR (d$_6$-DMSO) δ=0.64-0.78 (m, 6H), 1.10-1.28 (m, 4H), 1.29-1.48 (m, 2H), 1.53-1.61 (m, 1H), 1.83-1.98 (m, 1H), 3.21 (s, 3H), 7.15-7.24 (m, 1H), 7.40-7.48 (m, 1H), 7.59-7.69 (m, 2H), 7.86-7.95 (m, 2H), 11.55 (m, 1H). MS (m/e): 393 (M+H).

EXAMPLE 5

(±)-(E)-2-(2,2-Dimethyl-propyl)-1-(4-methanesulfonyl-phenyl)-cyclopropanecarboxylic acid thiazol-2-ylamide

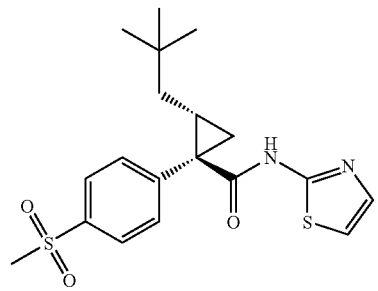

a: (E)-5,5-Dimethyl-2-(4-methylsulfanyl-phenyl)-hex-2-enoic acid ethyl ester Add sodium bistrimethylsilylamide(4.67 mL, 2.0 M in THF, 9.35 mmol) to a solution of (3,3-Dimethyl-butyl) phosphonium bromide (4.00 g, 9.35 mmol)in CH$_2$Cl$_2$/THF at 0° C. Dissolve (4-methylsulfanyl-phenyl)-oxo-acetic acid ethyl ester (prepared as described by I. T. Barnish et. al. *J. Med. Chem.* 1981, 24, 399-404) in THF and add the resulting solution to the reaction mixture at 78° C. Stir at room temperature over-night. Add water and extract 3 X with dichloromethane, dry over sodium sulfate and concentrate under vacuum to afford 2.79 g raw material as a yellow oil. Further purify this material via silica gel chromatography, eluting with a gradient from 100% hexane to 50:50 hexane:dichlormethan to afford a colorless oil (700 mg). MS (m/e): 293 (M+H).

b: (4-Methyl-pentyl)-triphenyl-phosphonium bromide

Dissolve 1-bromo-3,3-dimethylbutane(9.6 g, 58.15 mmol) in toluene, add triphenyl-phosphine (13.8 g, 55.2 mmol) and stir at 80° C. for 4 days in a scewcapglass and 3 days in an autoklav at 4 bar and 190° C. Cool the reaction mixture down to room temperature and isolate the product by crystallization in ether as a white solid (9.8 g). MS (m/e): 347 (M+H).

c: (E)-2-(4-Methanesulfonyl-phenyl)-5,5-dimethyl-hex-2-enoic acid ethyl ester Following the method of example 54d, oxidation of (E)-5,5-dimethyl-2-(4-methylsulfanyl-phenyl)-hex-2-enoic acid ethyl ester (680 mg, 2.34 mmol) with oxone® (1.86 g, 3.0 mmol) in methanol gives the title compound as a yellow oil (720 mg). MS (m/e): 325 (M+H).

d: (E)-2-(4-Methanesulfonyl-phenyl)-5,5-dimethyl-hex-2-en-1-ol

Reduction of (E)-2-(4-methanesulfonyl-phenyl)-5,5-dimethyl-hex-2-enoic acid ethyl ester (710 mg, 2.15 mmol) with DIBAL in toluene (3.85 ml, 4.67 mmol) following the method of example 54e gives the title compound as an amorphous solid (350 mg). MS (m/e): 283 (M+H).

e: (±)-(E)-[2-(2,2-Dimethyl-propyl)-1-(4-methanesulfonyl-phenyl)-cyclopropyl]-methanol Following the method of example 54f, reaction of (E)-2-(4-methanesulfonyl-phenyl)-5,5-dimethyl-hex-2-en-1-ol (340 mg, 1.2 mmol), diethylzinc in toluene (4.78 mL, 4.8 mmol), and diiodomethane (0.77 mL, 9.6 mmol) for 18 h at 60° C. affords the title compound as an amorphous solid (236 mg). MS (m/e): 279 ([M–H$_2$O]+H).

f: (±)-(E)-[2-(2,2-Dimethyl-propyl)-1-(4-methanesulfonyl-phenyl)-cyclopropanecarboxylic acid Oxidation of (±)-(E)-[2-(2,2-dimethyl-propyl)-1-(4-methanesulfonyl-phenyl)-cyclopropyl]-methanol (230 mg, 0.77 mmol) with chromium oxide (300 mg, 3 mmol), following the method of example 54g, gives the title compound as a white solid (155 mg).
$^1$H-NMR (CDCl$_3$) δ=0.72-2.10 (m, 14H), 2.93-3.15 (s, 3H), 7.40-7.53 (m, 2H), 7.84-7.97 (m, 2H).

g: (±)-(E)-2-(2,2-Dimethyl-propyl)-1-(4-methanesulfonyl-phenyl)-cyclopropanecarboxylic acid thiazol-2-ylamide Following the method of example 2h, reaction of 2-(2,2-dimethyl-propyl)-1-(4-methanesulfonyl-phenyl)-cyclopropanecarboxylic acid (150 mg, 0.48 mmol) with TBTU (163 mg, 0.52 mmol), triethylamine (0.132 mL, 0.96 mmol) and 2-aminothiazole (51.0 mg, 0.52 mmol) affords the title compound as white crystals (47.0 mg). $^1$H-NMR (d$_6$-DMSO) δ=0.01-0.12 (m, 1H), 0.89 (s, 9H), 1.31-1.40 (m, 1H), 1.41-1.50 (m, 1H), 1.66-1.75 (m, 1H), 1.90-2.03 (m, 1H), 3.24 (s, 3H), 7.16-7.19 (m, 1H), 7.41-7.45 (m, 1H), 7.59-7.65 (m, 2H), 7.87-7.93 (m, 2H), 11.44 (m, 1H). MS (m/e): 393 (M+H).

EXAMPLE 6

(±)-(E)-2-Cyclopentyl-1-[4-(3-diethylamino-propane-1-sulfonyl)-phenyl]-cyclopropanecarboxylic acid thiazol-2-ylamide

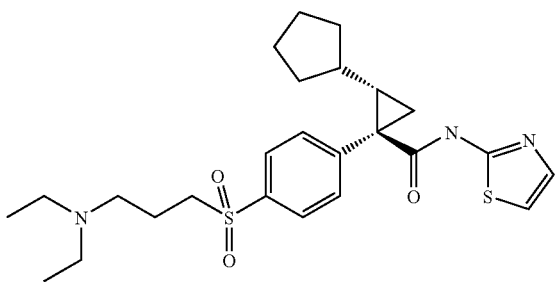

a: (E)-2-[4-(3-Benzyloxy-propylsulfanyl)-phenyl]-3-cyclopentyl-acrylic acid ethyl ester Add potassium acetate (1.7 g, 17.3 mmol), 4,4,5,5,4',4',5',5'-octamethyl-[2,2']bi[[1,3,2]dioxaborolanyl] (1.6 g, 6.35 mmol) and dichloro[1,1'-bis(diphenylphosphino)ferrocene]palladium (II) dichloromethane adduct (424 mg, 0.58 mmol) to a solution of 1-(3-benzyloxy-propylsulfanyl)-4-bromo-benzene (1.95 g, 5.77 mmol) in 15 mL DMF and stir 1 hour at 80° C. Then add (Z)-2-bromo-3-cyclopentyl-acrylic acid ethyl ester (2.85 g, 11.54 mmol), dichloro[1,1'-bis(diphenylphosphino)ferrocene]palladium (II) dichloromethane adduct (424 mg, 0.58 mmol) and sodium carbonate solution (2 M, 14.0 mL, 28.0 mmol) and stir at 80° C. over night. Add 100 mL ethyl acetate and filter. Wash with water and brine, filter through a hydrophobic filter paper and concentrate. Further purification via silica gel column chromatography, eluting with dichloromethane affords the title compound as yellow oil (4.37 g). MS (m/e): 425 (M+H).

b: (E)-2-[4-(3-Benzyloxy-propane-1-sulfonyl)-phenyl]-3-cyclopentyl-acrylic acid ethyl ester Following the method of example 54d, reaction of (E)-2-[4-(3-benzyloxy-propylsulfanyl)-phenyl]-3-cyclopentyl-acrylic acid ethyl ester (4.51 g, 10.6 mmol) dissolved in 500 mL methanol with a solution of oxone® (8.46 g, 13.8 mmol in 167 mL water) and 18 h at ambient temperature gives the title compound as an yellow oil (2.9 g). MS (m/e): 479 (M+Na).

c: (E)-2-[4-(3-Benzyloxy-propane-1-sulfonyl)-phenyl]-3-cyclopentyl-prop-2-en-1-ol Following the method of example 54e, reaction of (E)-2-[4-(3-benzyloxy-propane-1-sulfonyl)-phenyl]-3-cyclopentyl-acrylic acid ethyl ester (2.05 g, 4.49 mmol) with DIBAL in toluene (9.43 mL, 11.2 mmol) and 1 h at ambient temperature gives the title compound as an oil (1.45 g). MS (m/e): 415 (M+H).

d: (±)-(E)-{1-[4-(3-Benzyloxy-propane-1-sulfonyl)-phenyl]-2-cyclopentyl-cyclopropyl}-methanol Following the method of example 54f, reaction of (E)-2-[4-(3-benzyloxy-propane-1-sulfonyl)-phenyl]-3-cyclopentyl-prop-2-en-1-ol (1.45 g, 3.5 mmol) with diethylzinc in toluene (9.6 mL, 1.1 M in toluene, 10.5 mmol) and diiodomethane (2.81 g, 10.5 mmol) and 72 h at 60° C. affords the title compound as a yellow oil (1.42 g). MS (m/e): 451 (M+Na).

e: (±)-(E)-1-[4-(3-Benzyloxy-propane-1-sulfonyl)-phenyl]-2-cyclopentyl-cyclopropanecarboxylic acid Following the method of example 54g, reaction of (±)-(E)-{1-[4-(3-benzyloxy-propane-1-sulfonyl)-phenyl]-2-cyclopentyl-cyclopropyl}-methanol (1.42 g, 3.3 mmol) with a solution of chromium oxide (4.6 mL of a solution of 1.33 g chromium oxide dissolved in 1.2 mL concentrated sulfuric acid and diluted with water to a total volume of 5 mL) gives the title compound as an oil (960 mg). MS (m/e): 443 (M+H).

f: (±)4E)-2-Cyclopentyl-1-[4-(3-hydroxy-propane-1-sulfonyl)-phenyl]-cyclopropanecarboxylic acid Dissolve (±)-(E)-1-[4-(3-benzyloxy-propane-1-sulfonyl)-phenyl]-2-cyclopentyl-cyclopropanecarboxylic acid (950 mg, 2.15 mmol) in 250 mL methanol, add palladium (10% on carbon, 200 mg) and stir under hydrogen atmosphere at r.t. for 1 hour. Filter and concentrate to afford the raw product. Further purification via silica gel column chromatography, eluting with dichloromethane:methanol 99:1 gives the title compound as an oil (550 mg). MS (m/e): 353 (M+H).

g: (±)-(E)-2-Cyclopentyl-1-{4-[3-(toluene-4-sulfonyloxy]-propane-1-sulfonyl-phenyl}-cyclopropanecarboxylic acid Dissolve (±)-(E)-2-cyclopentyl-1-[4-(3-hydroxy-propane-1-sulfonyl)-phenyl]-cyclopropanecarboxylic acid (450 mg, 1.28 mmol) in 100 mL dichloromethane. Cool the solution down to 0° C. and add pyridine (2.1 mL, 25.6 mmol), stir 15 minutes and add slowly 4-methyl-benzenesulfonyl chloride (2.44 g, 12.8 mmol). Stir the resulting solution at r.t. for 72 h. For work up, add dichloromethane and wash with 0.5 N hydrochloric acid, water and brine. Filter the organic phase through hydrophobic filter paper and concentrate. Purify the resulting material via silica gel column chromatography, eluting with 99:1 dichloromethane:ethanol to afford 670 mg of the title compound as a colorless oil. MS (m/e): 505 (M–H).

h: (±)-(E)-Toluene4-sulfonic acid 3-{4-[2-cyclopentyl-1-(thiazol-2-ylcarbamoyl)-cyclopropyl]-benzenesulfonyl}-propyl ester Following the method of example 39 g, reaction of (±)-(E)-2-cyclopentyl-1-{4-[3-(toluene-4-sulfonyloxy)-propane-1-sulfonyl]-phenyl}-cyclopropanecarboxylic acid (120 mg, 0.24 mmol) with TBTU (8.3 mg, 0.26 mmol), 2-aminothiazole (26 mg, 0.26 mmol) and triethylamine (0.06 mL, 0.48 mmol) in 10 mL THF and adding TBTU (83 mg, 0.26 mmol), 2-aminothiazole (26 mg, 0.26 mmol) and triethylamine (0.06 mL, 0.48 mmol) after 48 h again and 4 h at r.t. gives the title compound as an oil (40 mg). MS (m/e): 589 (M+H).

i: (±)-(E)-2-Cyclopentyl-1-[4-(3-diethylamino-propane-1-sulfonyl)-phenyl]-cyclopropanecarboxylic acid thiazol-2-ylamide Dissolve (±)-(E)-toluene-4-sulfonic acid 3-{4-[2-cyclopentyl-1-(thiazol-2-ylcarbamoyl)-cyclopropyl]-benzenesulfonyl}-propyl ester (40 mg, 0.07 mmol) in 10 mL THF and add diethylamine (50 mg, 0.68 mmol). Stir at r.t. for 72 h and at 55° C. for 24 h. Concentrate under vacuum, add 10 mL acetonitrile, diethylamine (0.04 mL, 0.34 mmol), potassium carbonate (94 mg, 0.68 mmol) and reflux for 5 h. Concentrate under vacuum, dilute with dichloromethane and wash with water and brine. Filter through hydrophobic paper and concentrate. Purify the remaining material via silica gel column chromatography, eluting with 99:1 dichloromethane:methanol (NH$_3$) to afford 10 mg of a colorless oil. Further purify this material via preparative HPLC (Microsorb™ 60 C18, eluting with a gradient from 100:0 to 0:100 water(+0.1% TFA):acetonitrile) to afford the title compound as trifluoroacetic acid salt (4.5 mg). $^1$H-NMR (CDCl$_3$) δ0.71-0.94 (m, 2H), 1.22-1.50 (m, 14H), 1.76-1.89 (m, 1H), 2.25-2.42 (m, 3H), 3.05-3.44 (m, 8H), 6.98-7.10 (m, 1H), 7.34-7.46 (m, 1H), 7.58-7.66 (m, 2H), 7.90-7.99 (m, 2H). MS (m/e): 490 (M+H).

EXAMPLE 7

(±)-(E)-2-Cyclohexyl-1-[4-(3-diethylamino-propane-1-sulfonyl)-phenyl]-cyclopropanecarboxylic acid thiazol-2-ylamide

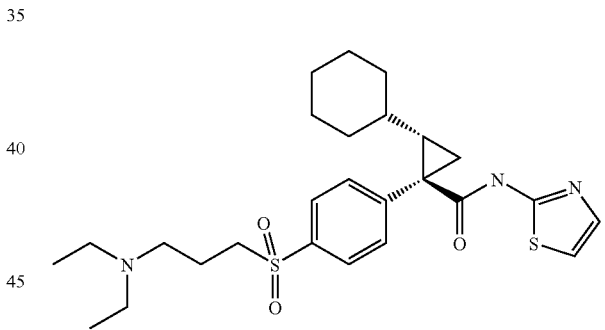

Dissolve (±)-(E)-methanesulfonic acid 3-{4-[2-cyclohexyl-1-(thiazol-2-ylcarbamoyl)-cyclopropyl]-benzenesulfonyl}-propyl ester (50 mg, 0.10 mmol) in 5.0 mL NMP and add diethylamine (139 mg, 1.90 mmol). Stir at r.t. for 48 h. Dilute with ethyl acetate and wash with brine. Filter through hydrophobic filter paper and concentrate. Purify the remaining oil (270 mg) via silica gel column chromatography, eluting with 99:1 dichloromethane:ethanol (NH$_3$) to afford 12 mg of a colorless oil. Purify this material via preparative HPLC (Microsorb™ 60 C18, eluting with a gradient from 100:0 to 0:100 water(+0.1% TFA):acetonitrile) to afford the title compound as trifluoroacetic acid salt (14 mg). $^1$H-NMR (d$_6$-DMSO) δ=0.12-0.31 (m, 1H), 0.63-0.83 (m, 1H), 0.86-1.23 (m, 10H), 1.39-1.70 (m, 7H), 1.88-2.03 (m, 3H), 3.05-3.16 (m, 6H), 3.38-3.50 (m, 2H), 7.14-7.25 (m, 1H), 7.38-7.47 (m, 1H), 7.62-7.73 (m, 2H), 7.85-7.93 (m, 2H), 9.14-9.33 (br. s, 1H), 11.42-11.64 (br. s. 1H). MS (m/e): 504 (M+H).

EXAMPLE 8

(±)-(E)-1-(3-Chloro4-sulfamoyl-phenyl)-2-cyclo-hexyl-cyclopropanecarboxylic acid thiazol-2-yla-mide

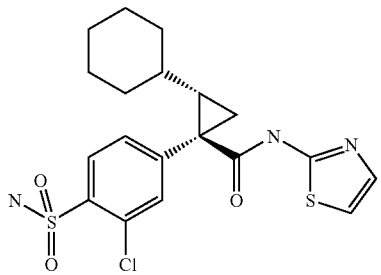

a: (E)-2-Chloro-4-(2-cyclohexyl-1-hydroxymethyl-vinyl)-benzenesulfonamide

According to example 26b, reaction of 4-bromo-2-chloro-benzenesulfonamide (1.0 g, 3.7 mmol), dichloro[1,1'-bis (diphenylphosphino)ferrocene]palladium (II) dichloromethane adduct (271 mg, 0.37 mmol), (E)-3-cyclohexyl-2-(4,4,5,5-tetramethyl-[1,3,2]dioxaborolan-2-yl)-prop-2-en-1-ol (1.5 g, 5.5 mmol) and aqueous sodium carbonat solution (2 M, 3.60 mL, 7.40 mmol) in 15 mL DMF at 80° C. and purification via column chromatography on silica gel, eluting with a gradient from 70:30 to 50:50 hexane:ethyl acetate affords the title compound as an oil (1.34 g). MS (m/e): 312 [(M−H$_2$O)+H].

b: (±)-(E)-2-Chloro4-(2-cyclohexyl-1-hydroxym-ethyl-cyclopropyl)-benzenesulfonamide Add a solution of diethylzinc in toluene (1.1 M, 11.0 mL, 12.0 mmol) to a solution of (E)-2-chloro-4-(2-cyclohexyl-1-hydroxymethyl-vinyl)-benzenesulfonamide (800 mg, 2.43 mmol) in 1,2-dichloroethane (40 mL). Warm the reaction mixture to 60° C. and add diiodomethane (1.65 mL, 24.0 mmol). Stir the reaction mixture at 60° C. for 48 h. Dilute the mixture with dichloromethane (100 mL) and wash with 1 N hydrochloric acid, saturated aqueous sodium bicarbonate solution and brine. Dry the organic layer, filter and concentrate. Add hexane (100 ml), stir and filter. Discard the filtrate and add ethanol to the solid. Filter and concentrate the filtrate to afford crude title compound as an oil (850 mg).

MS (m/e): 326[(M−H$_2$O)+H].

c: (±)-(E)-1-(3-Chloro-4-sulfamoyl-phenyl)-2-cyclo-hexyl-cyclopropanecarboxylic acid According to the method of example 54g, reaction of (±)-(E)-2-chloro-4-(2-cyclohexyl-1-hydroxymethyl-cyclopro-pyl)-benzenesulfonamide (850 mg, 2.43 mmol) and 1 h at 0° C. after the addition of the chromium oxide (2 mL of a solution of 1.33 g chromium oxide dissolved in 1.2 mL concentrated sulfuric acid and diluted with water to a total volume of 5 mL) gives the crude title compound as a solid (460 mg). Purify this material by adding hexane, filter and discard the filtrate to afford the title compound (410 mg). MS (m/e): 312 [(M−CO$_2$)—H].

d: (±)-(E)-1-(3-Chloro4-sulfamoyl-phenyl)-2-cyclo-hexyl-cyclopropanecarboxylic acid thiazol-2-yla-mide According to example 2h, reaction of (±)-(E)-1-(3-chloro-4-sulfamoyl-phenyl)-2-cyclohexyl-cyclopropanecarboxylic acid (310 mg, 0.87 mmol), TBTU (41.6 mg, 1.31 mmol), triethylamine (0.27 mL,.2.18 mmol) and 2-aminothiazole (131 mg, 1.31 mmol) in 10.0 mL THF and purification via column chromatography on silica gel, eluting with a gradient from 100:0 to 98:2 dichloromethane:ethanol (NH$_3$) affords crude title compound. Further purify this material via preparative HPLC (Microsorb™ 60 C18, eluting with a gradient from 100:0 to 0:100 water(+0.1% TFA):acetonitrile) to afford the title compound as TFA salt (10 mg). Purify this material via an additional column chromatography on silica gel, eluting with 98:2 dichloromethane:ethanol to afford the title compound as TFA salt (7.6 mg). $^1$H-NMR (d$_6$-acetone) δ=0.30-0.47 (m, 1H), 0.76-1.89 (m, 13H), 6.75-6.85 (bs, 1H), 7.04-7.14 (m, 1H), 7.29-7.41 (m, 1H), 7.61-7.69 (m, 1H), 7.71-7.78 (m, 1H), 8.05-8.13 (m, 1H). MS (m/e): 440 (M+H).

EXAMPLE 9

(±)-(E)-2-Cyclohexyl-1-[4-(propane-2-sulfonyl)-phenyl]-cyclopropanecarboxylic acid thiazol-2-yla-mide

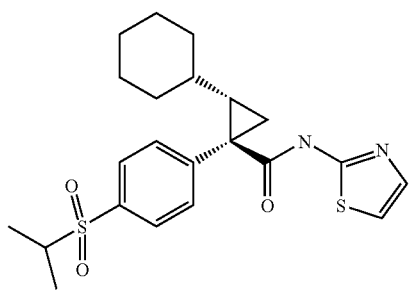

a: 1-Bromo-4-isopropylsulfanyl-benzene

Dissolve 4-bromo-benzenethiol (2.6 g, 13.2 mmol) in 150 mL acetone, add potassium carbonate (2.0 g, 14.5 mmol) and 2-bromo-propane (1.8 g, 14.5 mmol) and stir 2 days at r.t. Evaporate the solvent under vacuum, add water and extract with dichloromethane. Filter through a hydrophobic filter paper and concentrate. Purify the resulting material via column chromatography on silica gel, eluting with hexane:ethyl acetate 98:2 to afford the title compound as a yellow oil (2.06 g). MS (m/e): 231 [($^{79}$Br)M], 233 [($^{81}$Br)M].

b: (E)-3-Cyclohexyl-2-(4-isopropylsulfanyl-phenyl)-acrylic acid ethyl ester

Add potassium acetate (2.5 g, 26 mmol), 4,4,5,5,4',4',5',5'-octamethyl-[2,2']bi[[1,3,2]dioxaborolanyl] (2.42 g, 9.52 mmol) and dichloro[1,1'-bis(diphenylphosphino)ferrocene] palladium (II) dichloromethane adduct (629 mg, 0.86 mmol) to a solution of 1-bromo-4-isopropylsulfanyl-benzene (2.0 g, 8.65 mmol) in 30 mL DMF and stir 2 hour at 80° C. Then add (Z)-2-bromo-3-cyclohexyl-acrylic acid ethyl ester is (4.5 g, 17.3 mmol), dichloro[1,1'-bis(diphenylphosphino)ferrocene] palladium (II) dichloromethane adduct (629 mg, 0.86 mmol)

and sodium carbonate solution (2 M, 21.0 mL, 42.0 mmol) and stir at 80° C. over night. Add 100 mL ethyl acetate and filter. Wash with water and brine, filter through a hydrophobic filter paper and concentrate. Further purification via silica gel column chromatography, eluting with a gradient from 100:0 to 98:2 hexane:ethyl acetate affords the title compound as yellow oil (1.25 g). MS (m/e): 333 (M+H).

c: (E)-3-Cyclohexyl-2-[4-(propane-2-sulfonyl)-phenyl]-acrylic acid ethyl ester

Following the method of example 54d, oxidation of (E)-3-cyclohexyl-2-(4-isopropylsulfanyl-phenyl)-acrylic acid ethyl ester (1.25 g, 3.76 mmol) with oxone® (2.77 g, 4.51 mmol) in methanol gives the title compound as a yellow oil (848 mg). MS (m/e): 365 (M+H).

d: (E)-3-Cyclohexyl-2-[4-(propane-2-sulfonyl)-phenyl]-prop-2-en-1-ol

Following the method of example 54e, reaction of (E)-3-cyclohexyl-2-[4-(propane-2-sulfonyl)-phenyl]-acrylic acid ethyl ester (930 mg, 2.55 mmol) and DIBAL in toluene (1 M, 6.38 ml, 6.38 mmol) gives the title compound as an oil (4.96 g). MS (m/e): 323 (M+H).

e: (±)-(E)-{2-Cyclohexyl-1-[4-(propane-2-sulfonyl)-phenyl]-cyclopropyl}-methanol Following the method of example 54f, reaction of (E)-3-Cyclohexyl-2-[4-(propane-2-sulfonyl)-phenyl]-prop-2-en-1-ol (740 mg, 2.3 mmol) with diethylzinc in toluene (10 mL, 1.1 M, 11.5 mmol) and diidomethane (6.16 g, 23 mmol) and 18 h at 60° C. affords the title compound as a colorless oil (450 mg). MS (m/e): 337 (M+H).

f: (±)-(E)-2-Cyclohexyl-1-[4-(propane-2-sulfonyl)-phenyl]-cyclopropanecarboxylic acid Following the method of example 54g, reaction of (±)-(E)-{2-cyclohexyl-1-[4-(propane-2-sulfonyl)-phenyl]-cyclopropyl}-methanol (450 mg, 1.34 mmol) with a solution of chromium oxide (1.5 mL of a solution of 1.33 g chromium oxide dissolved in 1.2 mL concentrated sulfuric acid and diluted with water to a total volume of 5 mL) gives the title compound as an oil (210 mg). MS (m/e): 351 (M+H).

g: (±)-(E)-2-Cyclohexyl-1-[4-(propane-2-sulfonyl)-phenyl]-cyclopropanecarboxylic acid thiazol-2-ylamide Following the method of example 39 g, reaction of (±)-(E)-2-cyclohexyl-1-[4-(propane-2-sulfonyl)-phenyl]-cyclopropanecarboxylic acid (30 mg, 0.086 mmol) with TBTU (3.3 mg, 0.01 mmol), 2-aminothiazole (10 mg, 0.10 mmol) and triethylamine (0.021 mL, 0.17 mmol) in 5 mL THF gives crude title compound. Further purify this material via preparative HPLC (Microsorb™ 60 C18, eluting with a gradient from 100:0 to 0:100 water(+0.1% TFA):acetonitrile) to afford the title compound as trifluoroacetic acid salt (3.43 mg). $^1$H-NMR (d$_6$-acetone) δ=0.25-0.40 (m, 1H), 0.73-1.83 (m, 18H), 2.00-2.14 (m, 1H), 3.25-3.39 (m, 1H), 7.11-7.20 (m, 1H), 7.36-7.46 (m, 1H), 7.77-7.84 (m, 2H), 7.88-7.97 (m, 2H). MS (m/e): 433 (M+H).

EXAMPLE 10

(±)-(E)-2-Cyclohexyl-1-[4-(propane-2-sulfonyl)-phenyl]-cyclopropanecarboxylic acid [1,3,4]thiadiazol-2-ylamide

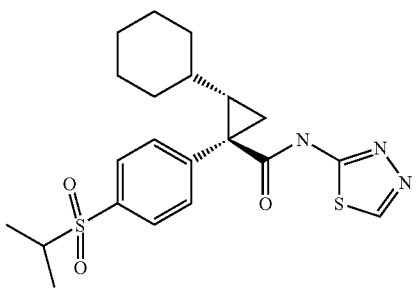

Following the method of example 39g, reaction of (±)-(E)-2-cyclohexyl-1-[4-(propane-2-sulfonyl)-phenyl]-cyclopropanecarboxylic acid (75 mg, 0.21 mmol) with TBTU (81 mg, 0.26 mmol), [1,3,4]thiadiazol-2-ylamine (26 mg, 0.26 mmol) and triethylamine (0.052 mL, 0.43 mmol) in 10 mL THF at 50° C. gives the title compound (42.2 mg). $^1$H-NMR (CDCl$_3$) δ=0.15-0.32 (m, 1H), 0.80-1.82 (m, 18H), 2.02-2.14 (m, 1H), 3.21-3.36 (m, 1H), 7.59-7.69 (m, 2H), 7.94-8.03 (m, 2H), 8.70-8.78 (bs, 1H), 8.80 (s, 1H). MS (m/e): 434 (M+H).

EXAMPLE 11

(±)-(E)-2-Cyclopentyl-1-(4-methanesulfonyl-phenyl)-cyclopropanecarboxylic acid (5-methyl-[1,3,4]thiadiazol-2-yl)-amide

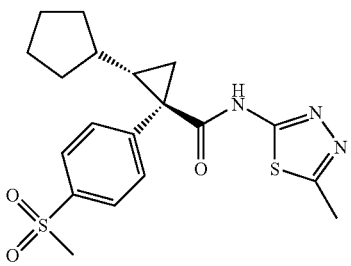

a: Cyclopentanecarbaldehyde

Dissolve cyclopentyl-methanol (100 g, 1 mol) in dichloromethane (0.5 L) and add to a suspension of pyridinium chlorochromate (270 g, 1.25 mol) and celite® (250 g) in dichloromethane (1.5 L) and stir at ambient for 1 6 h. Add diethyl ether (2 L) and filter the mix through a plug of silica gel. Evaporate to dryness to give the title product as an oil, containing residual solvent (103 g). GC-MS (m/e): 98 (M+).

b: (E)-3-Cyclopentyl-acrylic acid ethyl ester

Following the method of example 54a, reaction of triethylphosphinoacetate (196 g, 870 mmol) with hexane-washed sodium hydride (60% in mineral oil, 35 g, 870 mmol) in THF (1200 ml) and cyclopentanecarbaldehyde (86 g, 870 mmol) in THF (300 ml) gives the title product as an oil (59.1 g). MS (m/e): 169.1 (M+H).

c: (Z)-2-Bromo-3-cyclopentyl-acrylic acid ethyl ester

Following the method of example 54b, reaction of (E)-3-cyclopentyl-acrylic acid ethyl ester (87 g, 520 mmol) with bromine (29.3 ml, 572 mmol) and triethylamine (90 ml, 650 mmol) affords the title product as an oil (83.5 g) GC-MS (m/e): 247 (M+).

d: (E)-3-Cyclopentyl-2-(4-methylsulfanyl-phenyl)-acrylic acid ethyl ester

Following the method of example 54c, reaction of (Z)-2-bromo-3-cyclopentyl-acrylic acid ethyl ester (56.8 g, 229 mmol) with 4-(methylthio)benzene boronic acid (46.3 g, 276 mmol) and tetrakis(triphenylphosphino)palladium(0) (10.4 g, 3 mol %) in a mixture of toluene (1600 ml), ethanol (421 ml) and 2 M aqueous sodium carbonate solution (420 ml) affords the title compound as an oil (56.9 g). MS (m/e): 291.2 (M+H).

e: (E)-3-Cyclopentyl-2-(4-methanesulfonyl-phenyl)-acrylic acid ethyl ester

Add a suspension of oxone® (113 g, 183 mmol) in water (600 ml) to a solution of (E)-3-cyclopentyl-2-(4-methylsulfanyl-phenyl)-acrylic acid ethyl ester (24.2 g, 83 mmol) in acetone (600 ml). Stir overnight, and then add water (500 ml). Extract the resulting mixture with dichloromethane (2×500 ml). Combine the extracts, wash with brine (2×500 ml), dry over magnesium sulfate, and remove solvent under vacuum to afford the title compound as an off-white solid (25.8 g). MS (m/e): 323.4 (M+H).

f: (E)-3-Cyclopentyl-2-(4-methanesulfonyl-phenyl)-prop-2-en-1-ol

Following the method of example 54e, reaction of DIBAL in toluene (268 ml, 1.5 M, 402 mmol) with (E)-3-cyclopentyl-2-(4-methanesulfonyl-phenyl)-acrylic acid ethyl ester (51.8 g, 160 mmol) affords the title compound as a solid (45 g). MS (m/e): 303.4 (M+Na).

g: (±)-(E)-[2-Cyclopentyl-1-(4-methanesulfonyl-phenyl)-cyclopropyl]-methanol Following the method of example 54f, reaction of diethylzinc in hexanes (453 ml, 1.0 M, 453 mmol) with (E)-3-cyclopentyl-2-(4-methanesulfonyl-phenyl)-prop-2-en-1-ol (33.3 g, 113 mmol) in toluene (1500 ml) and diiodomethane (242 g, 906 mmol) affords the title compound (61 g). MS (m/e): 317.4 (M+Na).

h: (±)-(E)-2-Cyclopentyl-1-(4-methanesulfonyl-phenyl)-cyclopropanecarboxylic acid Add concentrated sulfuric acid (32 ml) to a ice-cold solution of chromium oxide (37.4 g, 374 mmol) in water (40 ml), and then dilute the resulting solution with water to a total volume of 140 ml. Add this solution drop-wise to a solution of (±)-(E)-[2-cyclopentyl-1-(4-methanesulfonyl-phenyl)-cyclopropyl]-methanol (20 g, 68 mmol) in acetone (400 ml) at 0° C. After the reaction mixture has been stirred for 2 hr, carefully add iso-propanol (15 ml) and stir for 15 minutes. Add water (1000 ml) and ether (500 ml). Separate the resulting two phases, and extract the aqueous layer with ether (2×500 ml). Combine the organic layer and extracts and dry over magnesium sulfate. Filter and concentrate the filtrate. Dissolve in chloroform (500 ml) and extract into 2M sodium hydroxide. The aqueous layer was acidified with 2 M hydrochloric acid and extracted into chloroform. Combined organic extracts were dried over magnesium sulfate and filtered. The filtrate was concentrated to afford the title compound as a yellow solid (15.4 g). MS (m/e): 307 (M–H).

i: (±)-(E)-2-Cyclopentyl-1-(4-methanesulfonyl-phenyl)-cyclopropanecarbonyl chloride Suspend (±)-(E)-2-cyclopentyl-1-(4-methanesulfonyl-phenyl)-cyclopropanecarboxylic acid (1.234 g, 4 mmol) in SOCl$_2$ (10 mL). Stir overnight at room temperature, then evaporate in vacuo. Redissolve the residue in ether and evaporate, repeat twice to obtain the title compound as an off-white solid (1.32 g, quant.): $^1$H-NMR (CDCl$_3$) δ=0.78-0.94 (m, 1H), 1.29-1.79 (m, 9H), 2.06-2.13 (m, 1H), 2.14-2.25 (m, 1H), 3.10 (s, 3H), 7.49-7.58 (m, 2H), 7.90-7.98 (m, 2H).

j: (±)-(E)-2-Cyclopentyl-1-(4-methanesulfonyl-phenyl)-cyclopropanecarboxylic acid (5-methyl-[1,3,4]thiadiazol-2-yl)-amide Add (±)-(E)-2-cyclopentyl-1-(4-methanesulfonyl-phenyl)-cyclopropanecarbonyl chloride (54.3 mg, 0.166 mmol, dissolved in 0.5 mL THF) dropwise to a stirred solution of 5-methyl-[1,3,4]thiadiazol-2-ylamine (11.5 mg, 0.10 mmol) and diisopropylethylamine (0.175 mL, 1 mmol) in 0.5 mL THF/DMF (4:1). Stir overnight at room temperature. Add DETA-resin (0.1 g, loading 7.44 mmol N/g; Polymer Laboratories) and stir overnight at room temperature. Filter, wash resin with dichloromethane and evaporate combined filtrates. Purify crude material by reversed phase HPLC (X Terra MS C18, eluting with a gradient from 100:0 to 0:100 water(+0.1% TFA):acetonitrile) to obtain the title compound (14.2 mg). $^1$H-NMR (CDCl$_3$) δ=0.75-0.93 (m, 1H), 1.21-1.73 (m, 9H), 1.79-1.88 (m, 1H), 2.10-2.24 (m, 1H), 2.67 (s, 3H), 3.16 (s, 3H), 7.59-7.71 (m, 2H), 7.98-8.10 (m, 2H). MS (m/e): 406.1 (M+H).

EXAMPLE 12

(±)-(E)-2-Cyclopentyl-1-(4-methanesulfonyl-phenyl)-cyclopropanecarboxylic acid isoxazol-3-ylamide

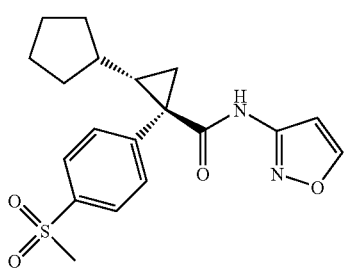

Using the method of Example 11j using (±)-(E)-2-cyclopentyl-1-(4-methanesulfonyl-phenyl)-cyclopropanecarbonyl chloride (54.3 mg, 0.166 mmol, dissolved in 0.5 mL THF) and isoxazol-3-ylamine (7.4 mL, 0.10 mmol) and diisopropylethylamine (0.175 mL, 1 mmol) in 0.5 mL THF gives the title compound (1 7.8 mg). $^1$H-NMR (CDCl$_3$) δ=0.72-0.89 (m, 1H), 1.21-1.29 (m, 1H), 1.30-1.53 (m, 4H), 1.54-1;73 (m, 4H), 1.73-1.81 (m, 1H), 2.04-2.16 (m, 1H), 3.16 (s, 3H), 7.05 (s, 1H), 7.60-7.70 (m, 3H), 7.98-8.06 (m, 2H), 8.26 (s, 1H). MS (m/e): 375.1 (M+H).

EXAMPLE 13

(±)-(E)-2-Cyclopentyl-1-(4-methanesulfonyl-phenyl)-cyclopropanecarboxylic acid (5-methyl-isoxazol-3-yl)-amide

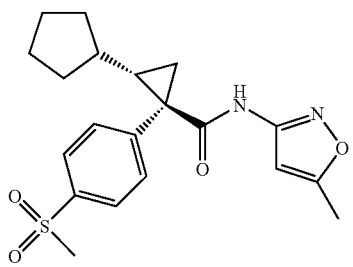

Using the method of Example 11j using (±)-(E)-2-cyclopentyl-1-(4-methanesulfonyl-phenyl)-cyclopropanecarbonyl chloride (54.3 mg, 0.166 mmol, dissolved in 0.5 mL THF) and 5-methyl-isoxazol-3-ylamine (9.7 mg, 0.10 mmol) and diisopropylethylamine (0.175 mL, 1 mmol) in 0.5 mL THF gives the title compound (16 mg). $^1$H-NMR (CDCl$_3$) δ=0.71-0.91 (m, 1H), 1.20-1.28 (m, 1H), 1.31-1.53 (m, 4H), 1.55-1.78 (m, 5H), 2.03-2.15 (m, 1H), 2.38 (s, 3H), 3.15 (s, 3H), 6.69 (s, 1H), 7.56-7.66 (m, 3H), 7.98-8.05 (m, 2H).

MS (m/e): 389.1 (M+H).

EXAMPLE 14

(±)-(E)-(2-{[2-Cyclopentyl-1-(4-methanesulfonyl-phenyl)-cyclopropanecarbonyl]-amino}-thiazol-4-yl)-acetic acid ethyl ester

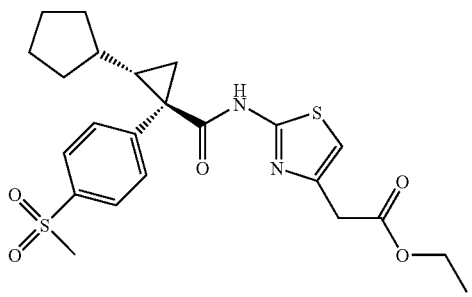

Using the method of Example 11j using (±)-(E)-2-cyclopentyl-1-(4-methanesulfonyl-phenyl)-cyclopropanecarbonyl chloride (54.3 mg, 0.166 mmol, dissolved in 0.5 mL THF) and (2-amino-thiazol-4-yl)-acetic acid ethyl ester (21.5 mg, 0.12 mmol) and diisopropylethylamine (0.175 mL, 1 mmol) in 0.5 mL THF gives the title compound as the trifluoroacetate salt (7.3 mg). $^1$H-NMR (CDCl$_3$) δ=0.71-0.93 (m, 1H), 1.22-1.53 (m, 8H), 1.54-1.73 (m, 4H), 1.77-1.83 (m, 1H), 2.11-2.23 (m, 1H), 3.14 (s, 3H), 3.66 (s. 2H), 4.16 (q, 2H), 6.83 (s, 1H), 7.57-7.65 (m, 2H), 7.97-8.05 (m, 2H). MS (m/e): 477.1 (M+H).

EXAMPLE 15

(±)-(E)-(2-{[2-Cyclopentyl-1-(4-methanesulfonyl-phenyl)-cyclopropanecarbonyl]-amino}-thiazole-4-carboxylic acid ethyl ester

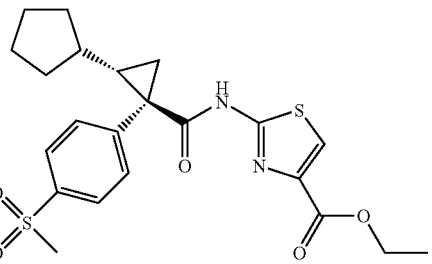

Using the method of Example 11j using (±)-(E)-2-cyclopentyl-1-(4-methanesulfonyl-phenyl)-cyclopropanecarbonyl chloride (54.3 mg, 0.166 mmol, dissolved in 0.5 mL THF) and 2-amino-thiazole-4-carboxylic acid ethyl ester (15.7 mg, 0.09 mmol) and diisopropylethylamine (0.175 mL, 1 mmol) in 0.5 mL THF gives the title compound (6.5 mg). $^1$H-NMR (CDCl$_3$) δ=0.73-0.90 (m, 1H), 1.28-1.51 (m, 8H), 1.53-1.73 (m, 4H), 1.80-1.87 (m, 1H), 2.12-2.23 (m, 1H), 3.22 (s, 3H), 4.37 (q, 2H), 7.60-7.65 (m, 2H), 7.80 (s, 1H), 8.01-8.06 (m, 2H), 8.55 (s, 1H). MS (m/e): 463.0 (M+H).

EXAMPLE 16

(±)-(Z)-2-Cyclopentylmethyl-1-(5-methanesulfonyl-thiophen-2-yl)-cyclopropanecarboxylic acid thiazol-2-ylamide

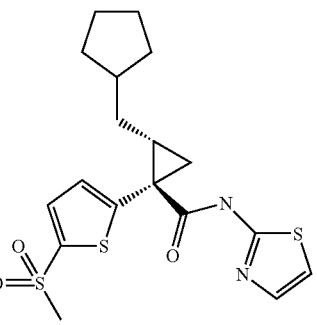

a: (2-Cyclopentyl-ethyl)-triphenyl-phosphonium bromide

Dissolve (2-bromo-ethyl)-cyclopentane (15.25 g, 86.1 mmol) which was prepared according to *Chem. Pharm. Bull.* 1992, 40, 9, 2391-2398 in toluene, add triphenyl-phosphine (22.58 g, 86.1 mmol) and stir at 110° C. for 48 h. Cool the reaction mixture to r.t., concentrate and crystallize the product from diethylether to give 31.47 g product. MS (m/e): 359.0 (M+H).

b: (5-Methylsulfanyl-thiophen-2-yl)-oxo-acetic acid ethyl ester

Add ethyloxalylchloride (15.4 g, 112.9 mmol) to a suspension of aluminiumchloride (17.34 g, 130.1 mmol) in 1,2-dichloroethane at 0° C. and stir 20 min after addition. Add a solution of 2-methylthio-thiophene (14 g, 107.5 mmol) in 1,2-dichloroethane and remain the reaction temperature at 0° C. After addition allow the reaction mixture to warm to r.t. and stir over night. Monitor completion of the reaction by LCMS. Pour reaction mixture into ice/water, extract the aqueous layer with dichloromethane, dry the combined organic layers over sodium sulfate and remove solvents in vacuum to get 22.9 g of the crude product. Further purify this material by silica gel chromatography, eluting with a gradient from 100:0 to 70:30 hexane: ethyl acetate to get 13,9 g of a mixture of (5-methylsulfanyl-thiophen-2-yl)-oxo-acetic acid ethyl ester and (3-methylsulfanyl-thiophen-2-yl)-oxo-acetic acid ethyl ester. MS (m/e): 231.0 (M+H).

c: (Z)-4-Cyclopentyl-2-(5-methylsulfanyl-thiophen-2-yl)-but-2-enoic acid ethyl ester Add potassium-tert.-butoxide (4.34 mL, 1.0 M in THF, 4.34 mmol) to a mixture of (2-cyclopentyl-ethyl)-triphenylphosphonium bromide (1.91 g, 3.34 mmol) in THF at r.t. dropwise and stir for 3 h. Add a solution of (Z)-(5-methylsulfanyl-thiophen-2-yl)-oxo-acetic acid ethyl ester (1.0 g, 4.34 mmol) in THF (4 mL) and stir for 16 h. Concentrate the reaction mixture, add water and extract with dichloromethane. Wash combined organic layers with saturated sodium chloride and dry over sodium sulfate. Remove solvent and purify crude product by silica gel chromatography, eluting with gradient from 100:0 to 85:15 hexane:ethylacetate to obtain 804 mg purified product. MS (m/e): 311.0 (M+H).

d: (Z)4-Cyclopentyl-2-(5-methanesulfonyl-thiophen-2-yl)-but-2-enoic acid ethyl ester Add a suspension of oxone® (2.07 g, 3.37 mmol) in water (10 mL) to a solution of (Z)-4-cyclopentyl-2-(5-methylsulfanyl-thiophen-2-yl)-but-2-enoic acid ethyl ester (804 mg, 2.59 mmol) in methanol (14 mL). Stir for 1 h, monitor completion of the reaction by LCMS. Filter the reaction mixture, concentrate the filtrate and extract the residue with dichloromethane. Combine the extracts, wash them with saturated aqueous sodium chloride solution, dry them over sodium sulfate, and remove solvent under vacuum to give 939 mg of the product. MS (m/e): 343.0 (M+H).

e: (Z)-4-Cyclopentyl-2-(5-methanesulfonyl-thiophen-2-yl)-but-2-en-1-ol

Add a solution of DIBAL (5.41 mL, 1.2 M in toluene, 6.48 mmol) dropwise over one h to a solution of (Z)-4-cyclopentyl-2-(5-methanesulfonyl-thiophen-2-yl)-but-2-enoic acid ethyl ester (939 mg, max. 2.59 mmol) in THF (5 mL) at to −78° C. Then allow the reaction mixture to warm slowly to r.t., and stir for 18 h. Add methanol (1.5 mL) at −78° C. and allow the reaction mixture to warm to r.t. Partition the residue between ethyl acetate (15 mL) and sodium potassium tartrate (15 mL). Then extract the aqueous layer with ethyl acetate. Combine the organic layers, wash them with saturated aqueous sodium chloride solution, dry over sodium sulfate and remove solvent under vacuum to give 812 mg crude product. MS (m/e): 323.0 (M+Na).

f: (±)-(Z)-[2-Cyclopentylmethyl-1-(5-methanesulfonyl-thiophen-2-yl)-cyclopropyl]-methanol Add a solution of diethylzinc (11.8 mL, 1.1M, 12.95 mmol) to a solution of (Z)-4-cyclopentyl-2-(5-methanesulfonyl-thiophen-2-yl)-but-2-en-1-ol (812 mg, max 2.59mmol), in toluene (40 mL). Warm the reaction mixture to 60° C., and add diiodomethane (2.09 mL, 25.9 mmol) dropwise over 2 h. Then stir the reaction mixture at 60° C. for 16 h. Treat the mixture with 1.0M hydrochloric acid. Wash the organic layer with saturated NaHCO$_3$ and saturated Na$_2$SO$_3$, dry over sodium sulfate and remove solvents under vacuum to obtain 1.27 g of crude product. Purify by silica gel chromatography, eluting with a gradient from 8:2 to 4:6 hexane:ethylacetate. 234 mg of titled compound obtained: MS (m/e): 337.0 (M+Na).

g: (±)-(Z)-12-Cyclopentylmethyl-1-(5-methanesulfonyl-thiophen-2-yl)-cyclopropanecarboxylic acid Add concentrated sulfuric acid (268 µL) to chromium oxide (297 mg, 2.97 mmol) and then dilute with water to a total volume of 1.12 mL. Add this solution dropwise to a solution (±)-(Z)-[2-cyclopentylmethyl-1-(5-methanesulfonyl-thiophen-2-yl)-cyclopropyl]-methanol (234 mg, 0.744 mmol) in acetone at 0° C. After the reaction mixture has been stirred for two h, carefully add saturated NaHCO$_3$. Filter the mixture and wash with ethylacetate and water. Acidify the aqueous phase with 1.0 M hydrochloric acid and extract with ethyl acetate. Combine the organic layers and wash them with saturated sodium chloride, dry over sodium sulfate and remove solvent under vacuum to give 282 mg crude product. MS (m/e): 329.0 (M+H).

h: (±)-(Z)-2-Cyclopentylmethyl-1-(5-methanesulfonyl-thiophen-2-yl)-cyclopropanecarboxylic acid thiazol-2-ylamide Add 2-amino-thiazole (208 mg, 2.08 mmol), TBTU (668 mg, 2.08 mmol), and triethylamine (627 µL, 4.46 mmol) to a solution of (±)-(Z)-[2-cyclopentylmethyl-1-(5-methanesulfonyl-thiophen-2-yl)-cyclopropanecarboxylic acid (282 mg, max.0.744 mmol), in THF. Stir the solution for seven h, and then concentrate under vacuum. Redissolve the residue in ethyl acetate (100 mL), and wash the resulting solution with saturated citric acid and saturated NaHCO$_3$. Dry the organic layer over sodium sulfate and remove solvent under vacuum. Purify the crude product by silica gel chromatography to obtain 64.6 mg of the titled compound: $^1$H-NMR (CDCl$_3$): δ=0.60-0.73 (m, 1H), 1.0-1.15 (m, 2H), 1.22-1.35 (m, 2H), 1.45-1.70 (m, 5H), 1.72-1.85 (m, 3H), 2.19-2.29 (m, 1H), 3.26 (s, 3H), 6.97 (mc, 1H), 7.14 (mc, 1H), 7.39 (mc, 1H), 7.70 (mc, 1H), 8.86 (bs, 1H). MS (m/e): 411.0 (M+H).

EXAMPLE 17

(±)-(Z)-2-Cyclohexyl-1l5-methanesulfonyl-thiophen-2-yl)-cyclopropanecarboxylic acid thiazol-2-ylamide

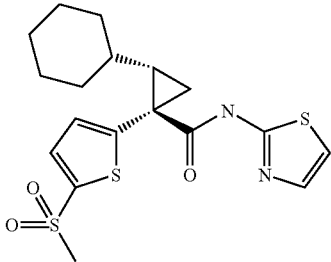

a: (Z)-3-Cyclohexyl-2-(5-methanesulfonyl-thiophen-2-yl)-prop-2-en-1-ol

Add 2-bromo-5-methanesulfonyl-thiophene (2.26 g, 9.39 mmol), caesium fluoride ( 2.85 g, 18.78 mmol) and tetrakis-(triphenylphosphin)-palladium(0) (543 mg, 0.47 mmol) to a solution of 3-cyclohexyl-2-(4,4,5,5-tetramethyl-[1,3,2]dioxaborolan-2-yl)-prop-2-en-1-ol (2.5 g, 9.39 mmol) in dioxane (50 mL). Stir at 80° C. for 24 h, monitor completion of the reaction by LCMS. Treat the reaction mixture with water and extract with dichloromethane. Dry organic layers over sodium sulfate and remove solvents under vacuum to obtain 4.85 g crude product. Purify by siliga gel chromatography, eluting with gradient from 10:0 to 7:3 hexane:ethyl acetate. 690 mg isolated product was (Z)-3-cyclohexyl-2-(5-methanesulfonyl-thiophen-2-yl)-propenal. MS (m/e): 299.0 (M+H). Add a solution of (Z)-3-cyclohexyl-2-(5-methanesulfonyl-thiophen-2-yl)-propenal (690 mg, 2.31 mmol) in methanol (2 mL) to a suspension of NaBH$_4$ in methanol (3 mL) at 0° C. and stir for 1 h, monitor completion of the reaction by LCMS. Dilute reaction mixture with water, extract with ethyl acetate, wash combined organic layers with water and saturated sodium chloride, dry over sodium sulfate and remove solvent under vacuum to obtain 704 mg crude product. MS (m/e): 301.0 (M+H).

b: (±)-(Z)-[2-Cyclohexyl-1-(5-methanesulfonyl-thiophen-2-yl)-cyclopropyl]-methanol According to method 16f was used (Z)-3-cyclohexyl-2-(5-methanesulfonyl-thiophen-2-yl)-prop-2-en-1-ol (704 mg, 2.34 mmol), diethylzinc (10.6 mL, 1.1M, 11.7 mmol) and diiodomethane (1.89 mL, 23.4 mmol) to give 146mg purified compound. MS (m/e): 337.0 (M+Na).

c: (±)-(Z)-2-Cyclohexyl-1-(5-methanesulfonyl-thiophen-2-yl)-cyclopropanecarboxylic acid According to method 16g was used (±)-(Z)-[2-cyclohexyl-1-(5-methanesulfonyl-thiophen-2-yl)-cyclopropyl]-methanol (146 mg, 0.464 mmol) and Jones reagent (698 µL, 4.64 mmol) to give 167 mg crude product. MS (m/e): 329.0 (M+H).

d: (±)-(Z)-2-Cyclohexyl-1-(5-methanesulfonyl-thiophen-2-yl)-cyclopropanecarboxylic acid thiazol-2-ylamide According to method 16h was used (±)-(Z)-2-cyclohexyl-1-(5-methanesulfonyl-thiophen-2-yl)-cyclopropanecarboxylic acid (167 mg, max.0.464 mmol), ²-amino-thiazole (143 mg, 1.43 mmol), TBTU (459 mg, 1.43 mmol) and triethylamine (310 pµL, 3.06 mmol) to give 60 mg purified compound: $^1$H-NMR (CDCl$_3$): 0.45-0.60 (m, 1H), 0.8-0.9 (m, 1H), 1.1-1.35 (m, 3H), 1.55-1.75 (m, 6H), 1.76-1.88 (m, 1H), 1.88-1.96 (m, 1H), 2.02-2.16 (m, 1H), 3.26 (s, 3H), 6.97 (mc, 1H), 7.20 (mc, 1H), 7.39 (mc, 1H), 7.71 (mc, 1H). MS (m/e): 411.0 (M+H).

EXAMPLE 18

(±)-(Z)-2-Cyclopentyl-1-(5-methanesulfonyl-thiophen-2-yl)-cyclopropanecarboxylic acid thiazol-2-ylamide

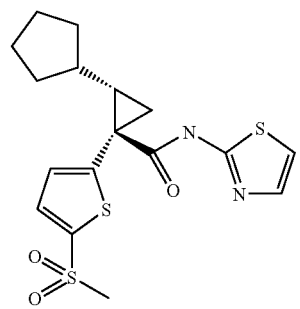

a: (Z)-3-Cyclopentyl-2-(5-methanesulfonyl-thiophen-2-yl)-prop-2-en-1-ol

According to method 17a was used 2-bromo-5-methanesulfonyl-thiophene (593 mg, 2.46 mmol), caesium fluoride (747 mg, 4.92 mmol), tetrakis-(triphenylphosphin)-palladium(0) (142 mg, 0.123 mmol) and 3-cyclopentyl-2-(4,4,5,5-tetramethyl-[1,3,2]dioxaborolan-2-yl)-prop-2-en-1-ol (620 g, 2.46 mmol) to give 395 mg of purified compound. MS (m/e): 309.0 (M+Na).

b: (±)-(Z)-[2-Cyclopentyl-1-(5-methanesulfonyl-thiophen-2-yl)-cyclopropyl]-methanol According to method 16f was used (Z)-3-cyclopentyl-2-(5-methanesulfonyl-thiophen-2-yl)-prop-2-en-1-ol (395 mg, 1.38 mmol), diethylzinc (6.90 mL, 1.0 M, 6.90 mmol) and diiodomethane (1.11 mL, 13.80 mmol) to give 242mg purified compound. MS (m/e): 323.0 (M+Na).

c: (±)-(Z)-2-Cyclopentyl-1-(5-methanesulfonyl-thiophen-2-yl)-cyclopropanecarboxylic acid According to method 16g was used (±)-(Z)-[2-cyclopentyl-1-(5-methanesulfonyl-thiophen-2-yl)-cyclopropyl]-methanol (242 mg, 0.805 mmol) and Jones reagent (1.20 mL, 3.22 mmol) to give 554 mg crude product. MS (m/e): 315.0 (M+H).

d: (±)-(Z)-2-Cyclopentyl-1-(5-methanesulfonyl-thiophen-2-yl)-cyclopropanecarboxylic acid thiazol-2-ylamide According to method 16h was used (±)-(Z)-2-cyclopentyl-1-(5-methanesulfonyl-thiophen-2-yl)-cyclopropanecarboxylic acid (350 mg, max. 0.805 mmol), 2-amino-thiazole (156 mg, 1.56 mmol), TBTU (501 mg, 1.56 mmol) and triethylamine (470 μL, 3.34 mmol) to give 152 mg of the racemic mixture: $^1$H-NMR (CDCl$_3$): 1.01-1.16 (m, 1H), 1.33-1.48 (m, 4H), 1.54-1.60 (m, 2H), 1.62-1.73 (m, 3H), 1.93-2.01 (m, 1H), 2.14-2.26 (m, 1H), 3.26 (s, 3H), 6.98 (mc, 1H), 7.20 (mc, 1H), 7.40 (mc, 1H), 7.70 (mc, 1H), 8.81 (bs, 1H). MS (m/e): 397.0 (M+H).

EXAMPLE 19

(Z)-2-Cyclopentyl-1-(5-methanesulfonyl-thiophen-2-yl)-cyclopropanecarboxylic acid thiazol-2-ylamide (±)-(Z)-2-cyclopentyl-1-(5-methanesulfonyl-thiophen-2-yl)-cyclopropanecarboxylic acid thiazol-2-ylamide can be separated into its enantiomers via chromatography on a chiralpak AD column, eluting with ethanol. Under the conditions given, the first enantiomer to elute is enantiomer 1.

EXAMPLE 20

(±)-(Z)-2-Cyclopentyl-1-(4-methanesulfonyl-thiophen-2-yl)-cyclopropanecarboxylic acid thiazol-2-ylamide

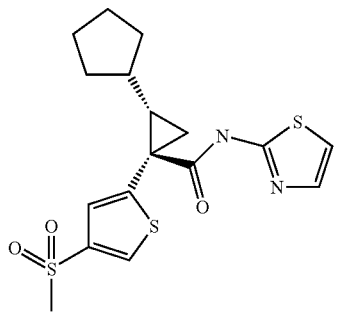

a: 2-Bromo-4-methanesulfonyl-thiophene

According to method of 16d was used 2-bromo-4-methylsulfanyl-thiophene (1.11 g, 5.33 mmol), which was prepared according to *J. Chem. Soc. Perkin Trans.* 1, 1995, 5, 537-540 and oxone®D (4.1 g, 6.66 mmol) to give 1.17 g of the product. MS (m/e): 241.0/243.0 (M+H).

b: (Z)-3-Cyclopentyl-2-(4-methanesulfonyl-thiophen-2-yl)-prop-2-en-1-ol

Add 2-bromo-4-methanesulfonyl-thiophene (241 mg, 1.0 mmol), caesium fluoride (304 mg, 2.0 mmol) and tetrakis-(triphenylphosphin)-palladium(0) (58 mg, 0.05 mmol) to a solution of 3-cyclopentyl-2-(4,4,5,5-tetramethyl-[1,3,2]dioxaborolan-2-yl)-prop-2-en-1-ol (252 mg, 1.0 mmol) in THF. Stir at 50° C. for 24 h, monitore completion of the reaction by LCMS. Treat the reaction mixture with water and extract with ethyl acetate. Dry organic layers over sodium sulfate and remove solvents under vacuum to obtain 405 mg crude product. Purify by silica gel chromatography, eluting with gradient from 9:1 to 1:1 hexane:ethyl acetate to obtain 118 mg purified product. MS (m/e): 309.0 (M+Na).

c: (±)-(Z)-[2-Cyclopentyl-1-(4-methanesulfonyl-thiophen-2-yl)-cyclopropyl]-methanol According to method 16f was used (Z)-3-cyclopentyl-2-(4-methanesulfonyl-thiophen-2-yl)-prop-2-en-1-ol (118 mg, 0.41 mmol), diethylzinc (2.1 mL, 1.0 M, 2.1 mmol) and diiodomethane (338 lμL, 4.1 mmol) to give 48 mg purified compound. MS (m/e): 323.0 (M+Na).

d: (d)-(Z)-2-Cyclopentyl-1-(4-methanesulfonyl-thiophen-2-yl)-cyclopropanecarboxylic acid According to method 16g was used (±)-(Z)-[2-cyclopentyl-1-(4-methanesulfonyl-thiophen-2-yl)-cyclopropyl]-methanol (48 mg, 0.16 mmol) and Jones reagent (240 μL, 0.64 mmol) to give 25 mg crude product. MS (m/e): 315.0 (M+H).

e: (±)-(Z)-2-Cyclopentyl-1-(4-methanesulfonyl-thiophen-2-yl)-cyclopropanecarboxylic acid thiazol-2-ylamide According to method 16h was used (±)-(Z)-2-cyclopentyl-1-(4-methanesulfonyl-thiophen-2-yl)-cyclopropanecarboxylic acid (25 mg, max. 0.08 mmol), 2-amino-thiazole (22 mg, 0.224 mmol), TBTU (72 g, 0.224 mmol) and triethylamine (67 μL, 0.48 mmol) to give 3.8 mg purified compound: $^1$H-NMR (CDCl$_3$): δ=1.02-1.17 (m, 1H), 1.32-1.55 (m, 6H), 1.6-1.72 (m, 2H), 1.74-1.85 (m, 1H), 1.91-1.97 (m, 1H), 2.12-2.25 (m, 1H), 3.17 (s, 3H), 6.97 (mc, 1H), 7.39 (mc, 1H), 7.44 (mc, 1H), 8.12 (mc, 1H), 8.90 (bs, 1H). MS (m/e): 397.0 (M+H).

EXAMPLE 21

(±)-(Z)-5-[2-Cyclohexyl-1-(thiazol-2-ylcarbamoyl)-cyclopropyl]-thiophene-2-carboxylic acid (2-dimethylamino-ethyl)-amide

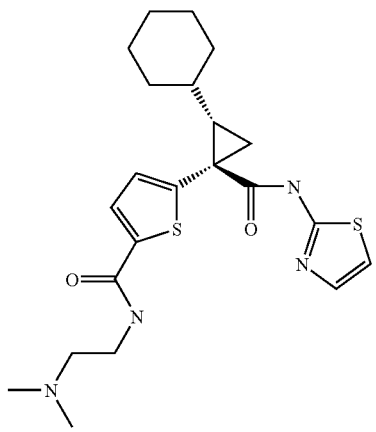

Mix (±)-(Z)-5-[2-cyclohexyl-1-(thiazol-2-ylcarbamoyl)-cyclopropyl]-thiophene-2-carboxylic acid (33 mg, 0.09 mmol), HATU (13.1 mg, 0.10 mmol) and PL-EDC resin (181 mg, 1.53 mmol/g, 0.28 mmol) with dichloromethane (1 mL)

and agitate on an orbital shaker for 30 min. Add 1-amino-2diethylamino-ethane (7.7 mg, 0.09 mmol) and agitate for 1.5 h. Add PL-EDA resin (56.2 mg, 6.64 mmol/g, 4.26 mmol) and agitate for 16 h. Filtrate the reaction mixture and remove solvent and purify the remaining material by silica gel chromatography to obtain 4.31 mg product. $^1$H-NMR (CDCl$_3$): δ=0.75-1.75 (m, 14H), 1.78-1.88 (m, 2H), 1.97-2.06 (m, 2H), 2.88 (s, 3H), 2.96 (s, 3H), 6.92 (mc, 1H), 7.08 (mc, 1H), 7.35 (mc, 1H), 7.60 (mc, 1H). MS (m/e): 447.0 (M+H).

EXAMPLE 22

(±)-(Z)-5-[2-Cyclohexyl-1-(thiazol-2-ylcarbamoyl)-cyclopropyl]-thiophene-2-carboxylic acid ethyl ester

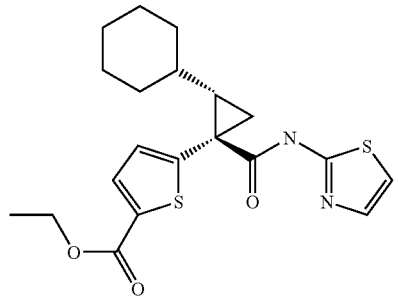

According to method 16h was used (±)-(Z)-5-(1-carboxy-2-cyclohexyl-cyclopropyl)-thiophene-2-carboxylic acid ethyl ester (2.41 g, max. 5.38 mmol), 2-amino-thiazole (754 mg, 7.53 mmol), TBTU (2.42 mg, 7.53 mmol) and triethylamine (2.27 mL, 16.14 mmol) to give 1.23 g purified compound. $^1$H-NMR (CDCl$_3$): δ=0.46-064 (m, 1H), 0.97-1.22 (m, 5H), 1.28-1.36 (m, 2H), 1.37-1.44 (m, 3H), 1.59-1.74 (m, 4H), 1.83-1.93 (m, 2H), 4.34-4.44 (m, 2H), 6.94 (mc, 1H), 7.14 (mc, 1H), 7.38 (mc, 1H), 7.77 (mc, 1H), 8.82 (bs, 1H). MS (m/e): 405.0 (M+H).

EXAMPLE 23

(±)-(Z)-2-Cyclopentyl-1-(5-sulfamoyl-thiophen-2-yl)-cyclopropanecarboxylic acid thiazol-2-ylamide

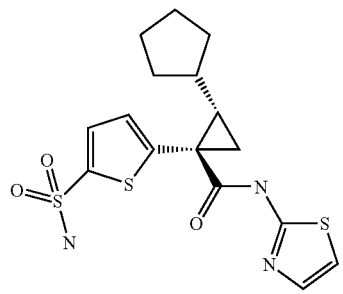

a: 5-Bromo-thiophene-2-sulfonic acid dimethylaminomethyleneamide

Add dimethoxymethyl-dimethyl-amine (1.05 mL, 7.66 mmol) to a solution of 5-bromo-thiophene-2-sulfonic acid amide (1.8 g, 7.43 mmol) in DMF (3 mL) at r.t. for 16 h. Pour reaction mixture into saturated sodium chloride, extract with ethylacetate. Wash combined organic layers with water, dry over sodium sulfate and remove solvent to obtain 2.52 g product. MS (m/e): 297.0/299.0 (M+H).

b: (Z)-5-(2-Cyclopentyl-1-hydroxymethyl-vinyl)-thiophene-2-sulfonic acid dimethylaminomethyleneamide According to method 20b was used (Z)-3-cyclopentyl-2-(4,4,5,5-tetramethyl-[1,3,2]dioxaborolan-2-yl)-prop-2-en-1-ol (678 mg, 2.69 mmol), 5-bromo-thiophene-2-sulfonic acid dimethylaminomethyleneamide (799 mg, 2.69 mmol), caesium fluoride (817 mg, 5.38 mmol) and tetrakis-(triphenylphosphin)-palladium(0) (155 mg, 0.135 mmol) to give 538 mg purified product. MS (m/e): 343.0 (M+H).

c: (±)-(Z)-5-(2-Cyclopentyl-1-hydroxymethyl-cyclopropyl)-thiophene-2-sulfonic acid dimethylaminomethyleneamide According to method 16f was used (Z)-5-(2-cyclopentyl-1-hydroxymethyl-vinyl)-thiophene-2-sulfonic acid dimethylaminomethyleneamide, (392 mg, 1.14 mmol), diethylzinc (5.72 mL, 1.0 M, 5.72 mmol) and diiodomethane (0.92 mL, 11.4 mmol) to give 48 mg purified compound. MS (m/e): 379.0 (M+Na).

d: (±)-(Z)-2-Cyclopentyl-1-[5-(dimethylaminomethylene-sulfamoyl)-thiophen-2-yl]-cyclopropanecarboxylic acid According to method 16g was used (±)-(Z)-5-(2-cyclopentyl-1-hydroxymethyl-cyclopropyl)-thiophene-2-sulfonic acid dimethylaminomethyleneamide (48 g, 0.134 mmol) and Jones reagent (200 µL, 0.536 mmol) to give 65 mg crude product. MS (m/e): 371.0 (M+H).

e: (±)-(Z)-2-Cyclopentyl-1-[5-(dimethylaminomethylene-sulfamoyl)-thiophen-2-yl]-cyclopropanecarboxylic acid thiazol-2-ylamide According to method 16h was used (±)-(Z)-2-cyclopentyl-1-[5-(dimethylaminomethylene-sulfamoyl)-thiophen-2-yl]-cyclopropanecarboxylic acid (65 mg, max. 0.344 mmol), 2-amino-thiazole (19 mg, 0.188 mmol), TBTU (60 mg, 0.188 mmol) and triethylamine (57 µL, 0.402 mmol) to give 43 mg of purified product. MS (m/e): 453.0 (M+H).

f: (a)-(Z)-2-Cyclopentyl-1-(5-sulfamoyl-thiophen-2-yl)-cyclopropanecarboxylic acid thiazol-2-ylamide Dilute (±)-(Z)-2-cyclopentyl-1-[5-(dimethylaminomethylene-sulfamoyl)-thiophen-2-yl]-cyclopropanecarboxylic acid thiazol-2-ylamide (43 mg, 0.095 mmol) with hydrochloric acid (2.5 mL, 5.0 M) and ethanol (2.5 mL) and stir 3 h at 80° C. Concentrate the reaction mixture and dissolve residue in ethyl acetate and add NaHCO$_3$. Extract aqueous layer with ethylacetate and wash combined organic layers with water and dry over sodium sulfate. Remove solvent to obtain 41 mg crude product. Purify crude product by silica gel chromatography, eluting with gradient from 8:2 to 4:6 hexane:ethylacetate to obtain 4.8mg purified product: $^1$H-NMR (CDCl$_3$): δ=1.05-1.85 (m, 10H), 1.88-1.96 (m, 1H), 2.12-2.24 (m, 1H), 5.76 (bs, 2H), 6.96 (mc, 1H), 7.09 (mc, 1H), 7.35 (mc, 1H), 7.59 (mc, 1H). MS (m/e): 398.0 (M+H).

EXAMPLE 24

(±)-(E)-2-Cyclopentyl-1-(5-methanesulfonyl-thiophen-3-yl)-cyclopropanecarboxylic acid thiazol-2-ylamide

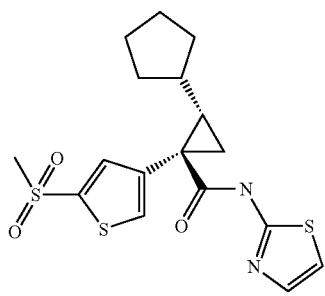

a: 4-Bromo-2-methanesulfonyl-thiophene

According to method 16d was used 4-bromo-2-methylsulfanyl-thiophene (1.36 g, 6.50 mmol), which was prepared according to *Journal of Medicinal Chemistriy*, 1995, 38,20, 3951-3955. and oxone® (4.40 g, 7.15 mmol) to give 1.51 g of the product. MS (m/e): 241.0/243.0 (M+H).

b: (E)-3-Cyclopentyl-2-(5-methanesulfonyl-thiophen-3-yl)-prop-2-en-1-ol

According to method 20b was used (Z)-3-cyclopentyl-2-(4,4,5,5-tetramethyl-[1,3,2]dioxaborolan-2-yl)-prop-2-en-1-ol (252 mg, 1.0 mmol), 4-Bromo-2-methanesulfonyl-thiophene (241 mg, 1.0 mmol), caesium fluoride ( 304 mg, 2.0 mmol) and tetrakis-(triphenylphosphin)-palladium(0) (58 mg, 0.05 mmol) to give 100 mg purified product. MS (m/e): 309.0 (M+Na).

c: (±)-(E)-[2-Cyclopentyl-1-(5-methanesulfonyl-thiophen-3-yl)-cyclopropyl]-methanol According to method 16f was used (E)-3-cyclopentyl-2-(5-methanesulfonyl-thiophen-3-yl)-prop-2-en-1-ol, (100 mg, 0.35 mmol), diethylzinc (1.75 mL, 1.0 M, 1.75 mmol) and diiodomethane (282 µL, 3.5 mmol) to give 37 mg purified compound. MS (m/e): 323.0 (M+Na).

d: (±)-2-(E)-Cyclopentyl-1-(5-methanesulfonyl-thiophen-3-yl)-cyclopropanecarboxylic acid According to method 16g was used (±)-(E)-[2-cyclopentyl-1-(5-methanesulfonyl-thiophen-3-yl)-cyclopropyl]-methanol (37 mg, 0.123 mmol) and Jones reagent (180 µL, 0.492 mmol) to give 26 g crude product. MS (m/e): 315.0 (M+H).

e: (=)-(E)-2-Cyclopentyl-1-(5-methanesulfonyl-thiophen-3-yl)-cyclopropanecarboxylic acid thiazol-2-ylamide According to method 16h was used (±)-(E)-2-cyclopentyl-1-(5-methanesulfonyl-thiophen-3-yl)-cyclopropanecarboxylic acid (26 mg, 0.082 mmol), 2-amino-thiazole (23mg, 0.231 mmol), TBTU (74 mg, 0.231 mmol) and triethylamine (70 µL, 0.496 mmol) to give 7.7 mg of purified product: $^1$H-NMR (CDCl$_3$): δ=0.80-1.0 (m, 2H), 1.18-1.76 (m, 8H), 1.77-1.87 (m, 1H), 1.99-2.16 (m, 1H), 3.25 (s, 3H), 6.96 (mc, 1H), 7.37 (mc, 1H), 7.70 (mc, 2H). MS (m/e): 397.0 (M+H).

EXAMPLE 25

(Z)-1-(5-Bromo-thiophen-2-yl)-2-cyclohexyl-cyclopropanecarboxylic acid thiazol-2-ylamide, enantiomer 1,

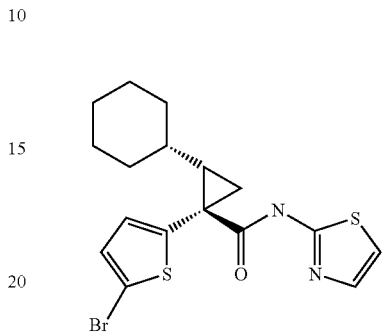

a: (5-Bromo-thiophen-2-yl)-oxo-acetic acid ethyl ester

According to method 16b was used 2-bromo-thiophene (68.0 g, 0.417 mol), ethyloxalylchloride (59.8 g, 0.438 mol), aluminiumchloride (67.3 g, 0.505 mol) to give 111.2 g crude product. MS (m/e): 263.0/265.0 (M+H).

b: (Z)-2-(5-Bromo-thiophen-2-yl)-3-cyclohexyl-acrylic acid ethyl ester

According to method 16c was used (5-bromo-thiophen-2-yl)-oxo-acetic acid ethyl ester (111.2 g, max. 0.417 mol), cyclohexylmethyl-triphenyl-phosphonium bromide (183.2 g, 0.417mol) and potassium-tert.-butoxide (438 mL, 1.0 M in THF, 0.438 mol) to give 129.7g crude product: $^1$H-NMR (CDCl$_3$): δ=1.18-1.25 (m, 5H), 1.27-1.33 (m, 3H), 1.60-1.75 (m, 5H), 2.33-2.50 (m, 1H), 4.18-4.27 (m, 2H), 6.69 (mc, 1H), 6.89 (mc, 1H), 6.98 (mc, 1H).

c: Cyclohexylmethyl-triphenyl-phosphonium bromide

Mix triphenylphosphine (200 g, 0.76 mol) and bromomethyl-cyclohexane (400 g, 2.26 mol) under an argon atmosphere and stir 16 h at 165° C. Pour the reaction mixture into 750 mL toluene and stir until the suspension reached ambient temperature. Filter and wash the product with diethylether and dry under vaccum to get 332.3 g pure product. MS (m/e): 359.0 (M+H).

d: (Z)-2-(4-Bromo-cyclopenta-1,3-dienyl)-3-cyclohexyl-acrylic acid

Dissolve (Z)-2-(5-bromo-thiophen-2-yl)-3-cyclohexyl-acrylic acid ethyl ester (116 g, 0.338 mol) in MeOH (600 mL) and dioxane (600 mL), add sodium hydroxide (730 mL, 1.0 M, 0.730 mol) and stir 16 h at ambient temperature. Concentrate the reaction mixture, acidify the aqueous residue with concentrated hydrochloric acid (75 mL) and extract with ethylacetate. Wash with saturated sodium chloride, dry over sodium sulfate and remove solvent under vacuum to get 124 g crude product. MS (m/e): 315.0/317.0 (M+H).

e: (Z)-2-(4-Bromo-cyclopenta-1,3-dienyl)-3-cyclohexyl-acrylic acid methyl ester Dissolve (Z)-2-(4-bromo-cyclopenta-1,3-dienyl)-3-cyclohexyl-acrylic acid (124 g, max. 0.338 mol) in dry THF (500 mL) and DMF (2 mL) and cool with an ice bath. Add oxalylchloride (51.5 g, 0.406 mol) slowly and stir 1 h 30 min after addition at 0-10° C. Add MeOH (500 mL) and stir 1 h at ambient temperature. Concentrate the reaction mixture and dilute residue with ethylacetate (600 mL) and add water (400 mL). Extract aqueous phase with ethylacetate and wash combined organic layers with saturated sodium chloride, dry over sodium sulfate and remove-solvents under vacuum to get 116.9 g crude product. MS (m/e): 329.0/331.0 (M+H).

f: (Z)-2-(4-Bromo-cyclopenta-1,3-dienyl)-3-cyclohexyl-prop-2-en-1-ol

According to method 16e was used (Z)-2-(4-bromo-cyclopenta-1,3-dienyl)-3-cyclohexyl-acrylic acid methyl ester (116.9 g, max. 0.338 mol), DIBALH (750 ml, 20% in toluene, 0.887 mol) to get 105 g crude product. Purify by silica gel chromatography, eluting with gradient 10:0 to 6:4 hexane: TBME to get 34.7 g pure compound. MS (m/e): 301.0/303.0 (M+H).

g: (±)-(Z)-[1-(5-Bromo-thiophen-2-yl)-2-cyclohexyl-cyclopropyl]-methanol

According to method 16f was used (±)-(Z)-2-(4-bromo-cyclopenta-1,3-dienyl)-3-cyclohexyl-prop-2-en-1-ol (21.7 g, 72.0 mmol), diethylzinc (330 mL, 1.1 M in toluene, 360 mmol) and diiodomethane (58 mL, 720 mmol) to give 48.0 g crude product, which was crystallized from hexane to give 11.7 g pure compound. MS (m/e): 297.0/299.0 (M–H$_2$O+H).

h: (Z)-[1-(5-Bromo-thiophen-2-yl)-2-cyclohexyl-cyclopropyl]-methanol (±)-(Z)-[1-(5-bromo-thiophen-2-yl)-2-cyclohexyl-cyclopropyl]-methanol (10.7 g, 35.5 mmol) was separated by chriral purification (Novasep 80 mm ID column, Daicel Chiralpak AD 20 μm, eluent:acetonitrile+0.3% ethyl-dimethylamine) to give enantiomer1 (5.5 g, 18.2 mmol).

i: (Z)-1-(5-Bromo-thiophen-2-yl)-2-cyclohexyl-cyclopropanecarboxylic acid

According to method 16g was used (Z)-[1-(5-bromo-thiophen-2-yl)-2-cyclohexyl-cyclopropyl]-methanol, enantiomer 1 (158 mg, 0.50 mmol) and Jones reagent (423 μL, 1.50 mmol) to give 153 mg crude product. MS (m/e): 329.0/331.0 (M+H).

j: (Z)-1-(5-Bromo-thiophen-2-yl)-2-cyclohexyl-cyclopropanecarboxylic acid thiazol-2-ylamide According to method 16h was used (Z)-1-(5-bromo-thiophen-2-yl)-2-cyclohexyl-cyclopropanecarboxylic acid thiazol-2-ylamide (153 mg, max.0.46 mmol), 2-amino-thiazole (65 mg, 0.65 mmol), TBTU (209 g, 0.65 mmol) and triethylamine (194 μL, 1.38 mmol) to give 120 mg purified compound: $^1$H-NMR (CDCl$_3$): δ=0.53-0.63 (m, 1H), 1.10-1.25 (m, 5H), 1.56-1.73 (m, 5H), 1.80-1.94 (m, 2H), 1.95-2.03 (m, 1H), 6.89 (mc, 1H), 6.94 (mc, 1H), 7.05 (mc, 1H), 7.39 (mc, 1H), 8.90 (bs, 1H). MS (m/e): 411.0/413.0 (M+H).

EXAMPLE 26

(E)-2-Cyclopentyl-1-[4-(2-pyridin-2-yl-ethylsulfamoyl)-phenyl]-cyclopropanecarboxylic acid thiazol-2-ylamide

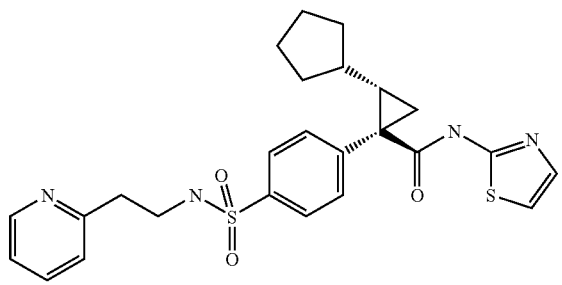

a: 4-Bromo-N-(2-pyridin-2-yl-ethyl)-benzenesulfonamide

Add a solution of 4-bromo-benzenesulfonyl chloride (1.278 g, 5.0 mmol) in 10 mL dichloromethane at r.t. to a solution of 2-pyridin-2-yl-ethylamine (611 mg, 5.0 mmol) and triethylamine (708 μL, 5.0 mmol) in 5 mL dichloromethane over a period of 20 min via syringe pump and stir for 12 h. Add 20 mL saturated aqueous sodium bicarbonate solution and extract the aqueous phase with dichloromethane. Wash the combined organic extracts with brine, dry over sodium sulfate, filtrate and concentrate under reduced pressure to obtain 4-bromo-N-(2-pyridin-2-yl-ethyl)-benzenesulfonamide (1.67 g) as a pale yellow oil which slowly crystallizes upon storage at ambient temperature. Further purification is not necessary. MS (m/e): 342 (M+H).

b: (E)4-(2-Cyclopentyl-1-hydroxymethyl-vinyl)-N-(2-pyridin-2-yl-ethyl)-benzenesulfonamide Heat a suspension of 4-bromo-N-(2-pyridin-2-yl-ethyl)-benzenesulfonamide (1.67 g, 4.89 mmol), (E)-3-cyclopentyl-2-(4,4,5,5-tetramethyl-[1,3,2]dioxaborolan-2-yl)-prop-2-en-1-ol (1.60 g, 6.36 mmol), caesium fluoride (2.23 g, 14.7 mmol) and tetrakis(triphenylphosphino)palladium(0) (565 mg, 489 μmol) in 50 mL dioxane to reflux for 2 d and cool to r.t. thereafter. After addition of 50 mL THF filtrate the resulting suspension, wash with dichloromethane and concentrate under reduced pressure. Further purify the resulting brown oil by column chromatography, eluting with a gradient from 100:0 to 0:100 hexanes:ethyl acetate to afford (E)-4-(2-cyclopentyl-1-hydroxymethyl-vinyl)-N-(2-pyridin-2-yl-ethyl)-benzenesulfonamide (929 mg) as a pale yellow oil. MS (m/e): 387 (M+H).

c: (±)-(E)4-(2-Cyclopentyl-1-hydroxymethyl-cyclopropyl)-N-(2-pyridin-2-yl-ethyl)-benzenesulfonamide Add a 1.1 M solution of diethylzinc in toluene (10.9 mL, 12.0 mmol) at r.t. to a solution of (E)-4-(2-cyclopentyl-1-hydroxymethyl-vinyl)-N-(2-pyridin-2-yl-ethyl)-benzenesulfonamide (929 mg, 2.41 mmol) in 70 mL dichloroethane over a period of 10 min. After complete addition heat to 60° C., add diiodomethane (6.33 g, 24.0 mmol) over a period of 2 h via syringe pump, and stir for 16 h at that temparature. Cool back to r.t., add another portion diethylzinc (3.6 mL, 4.0 mmol), heat to 60° C., add diiodomethane (2.11 g, 8.0 mmol) and stir for 1 h. After cooling to r.t. add 50 mL saturated aqueous ammonium chloride solution and extract the aqueous phase with dichloromethane. Dry the combined organic extracts over sodium sulfate, filtrate, concentrate and purify the resulting oil by column chromatography, eluting With a gradient from 100:0 to 0:100 hexanes:ethyl acetate to obtain (±)-(E)-4-(2-cyclopentyl-1-hydroxymethyl-cyclopropyl)-N-(2-pyridin-2-yl-ethyl)-benzenesulfonamide (720 mg) as a white solid. MS (m/e): 401 (M+H).

d: Separation of (±)-(E)4-(2-Cyclopentyl-1-hydroxymethyl-cyclopropyl)-N-(2-pyridin-2-yl-ethyl)-benzenesulfonamide into its enantiomers (±)-(E)-4-(2-Cyclopentyl-1-hydroxymethyl-cyclopropyl)-N-(2-pyridin-2-yl-ethyl)-benzenesulfonamide can be separated into its enantiomers via chromatography on a Chiralpak AD_column, eluting with hexane TFA 0.05%/isopropanol 80:20. Under the conditions given, the first enantiomer to elute is (E)-4-(2-cyclopentyl-1-hydroxymethyl-cyclopropyl)-N-(2-pyridin-2-yl-ethyl)-benzenesulfonamide, enantiomer 1.

e: (E)-2-Cyclopentyl-1-[4-(2-pyridin-2-yl-ethylsulfamoyl)-phenyl]-cyclopropanecarboxylic acid Prepare the Jones reagent (~2.7 M) by dissolving chromium oxide (1.33 g, 13.3 mmol) in conc. sulfuric acid (1.2 mL) and dilution with water to a total volume of 5 mL. Add Jones reagent (560 μL, 1.52 mmol) to a solution of (E)-4-(2-cyclopentyl-1-hydroxymethyl-cyclopropyl)-N-(2-pyridin-2-yl-ethyl)-benzenesulfonamide, enantiomer 1 (152 mg, 380 μmol) in 10 mL acetone and stir the mixture at r.t. for 3 h. Add 10 mL saturated aqueous sodium bicarbonate solution, stir for 30 min, bring to pH=6 with 2 M hydrochloric acid, filtrate and wash the filter with ethyl acetate. Extract the aqueous phase with ethyl acetate, wash the combined organic extracts with brine, dry over sodium sulfate, filtrate and concentrate under reduced pressure to obtain (E)-2-cyclopentyl-1-[4-(2-pyridin-2-yl-ethylsulfamoyl)-phenyl]-cyclopropanecarboxylic acid (90 mg) as a yellow solid, which is not further purified. MS (m/e): 415 (M+H).

f: (E)-2-Cyclopentyl-1-[4-(2-pyridin-2-yl-ethylsulfamoyl)-phenyl]-cyclopropanecarboxylic acid thiazol-2-ylamide Add TBTU (174 mg, 543 μmol) and triethylamine (183 μL, 1.30 mmol) to a solution of (E)-2-cyclopentyl-1-[4-(2-pyridin-2-yl-ethylsulfamoyl)-phenyl]-cyclopropanecarboxylic acid as obtained in example 26e (90 mg, 217 μmol) in 15 mL THF, stir for 30 min at ambient temperature, add 2-aminothiazole (54 mg, 543 μmol) and stir at r.t. for 3 d. Concentrate to remove THF, add 20 mL water and extract with ethyl acetate. Wash the combined organic extracts with brine, dry over sodium sulfate, filtrate and concentrate under reduced pressure. Purify the resulting brown oil by column chromatography, eluting with a gradient from 100:0 to 0:100 hexanes: ethyl acetate to obtain (E)-2-cyclopentyl-1-[4-(2-pyridin-2-yl-ethylsulfamoyl)-phenyl]-cyclopropanecarboxylic acid thiazol-2-ylamide (45 mg) as a white solid. Prepare an analytical sample by preparative HPLC, eluting with a gradient from 100:0 water(+0.1% TFA):acetonitrile to afford the title compound as white crystals. $^1$H-NMR (CDCl$_3$) of the TFA-salt δ=0.85 (mc, 1H), 1.31-1.48 (m, 5H), 1.55-1.70 (m, 4 H), 1.80 (mc, 1H), 2.13 (mc, 1H), 3.36 (mc, 2H), 3.49 (mc, 2H), 7.01 (mc, 1H), 7.40 (mc, 1H), 7.53 (mc, 2H), 7.69-7.80 (m, 2H), 7.85 (mc, 2H), 8.28 (mc, 1H), 8.70 (mc, 1H). MS (m/e): 497 (M+H).

EXAMPLE 27

(E)-2-Cyclopentyl-1-[4-(2-pyridin-2-yl-ethylsulfamoyl)-phenyl]-cyclopropanecarboxylic acid thiazol-2-ylamide

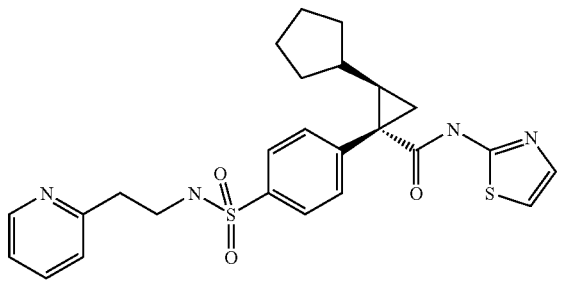

a: (E)-2-Cyclopentyl-1-[4-(2-pyridin-2-yl-ethylsulfamoyl)-phenyl]-cyclopropanecarboxylic acid Add Jones reagent (530 μL, 1.43 mmol) to a solution of (E)-4-(2-cyclopentyl-1-hydroxymethyl-cyclopropyl)-N-(2-pyridin-2-yl-ethyl)-benzenesulfonamide, enantiomer 2 as obtained in example 26d (143 mg, 358 μmol) in 10 mL acetone and stir the mixture at r.t. for 3 h. Add 10 mL saturated aqueous sodium bicarbonate solution, stir for 30 min, bring to pH=6 with 2 M hydrochloric acid, filtrate and wash the filter with ethyl acetate. Extract the aqueous phase with ethyl acetate, wash the combined organic extracts with brine, dry over sodium sulfate, filtrate and concentrate under reduced pressure to obtain (E)-2-cyclopentyl-1-[4-(2-pyridin-2-yl-ethylsulfamoyl)-phenyl]-cyclopropanecarboxylic acid (81 mg) as a yellow solid, which is not further purified. MS (m/e): 415 (M+H).

b: (E)-2-Cyclopentyl-1-[4-(2-pyridin-2-yl-ethylsulfamoyl)-phenyl]-cyclopropanecarboxylic acid thiazol-2-ylamide Add TBTU (162 mg, 506 μmol) and triethylamine (171 μL, 1.22 mmol) to a solution of (E)-2-cyclopentyl-1-[4-(2-pyridin-2-yl-ethylsulfamoyl)-phenyl]-cyclopropanecarboxylic acid as obtained in example 27a (81 mg, 217 μmol) in 15 mL THF, stir for 30 min at ambient temperature, add 2-aminothiazole (51 mg, 506 μmol) and stir at r.t. for 3 d. Concentrate to remove THF, add 20 mL water and extract with ethyl acetate. Wash the combined organic extracts with brine, dry over sodium sulfate, filtrate and concentrate under reduced pressure. Purifiy the resulting brown oil by column chromatography, eluting with a gradient from 100:0 to 0:100 hexanes: ethyl acetate to obtain (E)-2-cyclopentyl-1-[4-(2-pyridin-2-yl-ethylsulfamoyl)-phenyl]-cyclopropanecarboxylic acid thiazol-2-ylamide (30 mg) as a white solid. $^1$H-NMR (CDCl$_3$) δ=0.83 (mc, 1H), 1.31-1.48 (m, 5H), 1.55-1.70 (m, 4 H), 1.78 (mc, 1H), 2.12 (mc, 1H), 3.00 (mc, 2H), 3.49 (mc, 2H), 6.59 (mc, 1H), 6.92 (mc, 1H), 7.12 (mc, 2H), 7.30 (mc, 1H), 7.56 (mc, 3 H), 7.88 (mc, 2H), 8.48 (mc, 1H). MS (m/e): 497 (M+H).

EXAMPLE 28

(±)-(E)-2-Cyclopentyl-1-{4-[(pyridin-3-ylmethyl)-sulfamoyl]-phenyl}-cyclopropanecarboxylic acid thiazol-2-ylamide

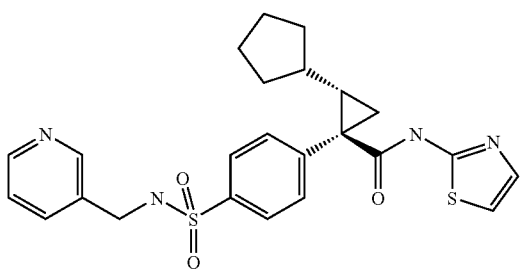

a: 4-Bromo-N-pyridin-3-ylmethyl-benzenesulfonamide

According to the procedure described for example 26a the use of 4-bromo-benzenesulfonyl chloride (1.278 g, 5.0 mmol) in 10 mL dichloromethane and C-Pyridin-3-yl-methylamine (541 mg, 5.0 mmol) and triethylamine (708 µL, 5.0 mmol) in 5 mL dichloromethane gives 4-bromo-N-pyridin-3-ylmethyl-benzenesulfonamide (1.54 g) as a pale yellow oil which slowly crystallizes upon storage at ambient temperature. Further purification is not necessary. MS (m/e): 328 (M+H).

b: (E)4-(2-Cyclopentyl-1-hydroxymethyl-vinyl)-N-pyridin-3-ylmethyl-benzenesulfonamide According to the procedure described for example 26b the use of 4-bromo-N-pyridin-3-ylmethyl-benzenesulfonamide (654 mg, 2.0 mmol), (E)-3-cyclopentyl-2-(4,4,5,5-tetramethyl-[1,3,2]dioxaborolan-2-yl)-prop-2-en-1-ol (504 mg, 2.00 mmol), caesium fluoride (608 mg, 4.00 mmol) and tetrakis(triphenylphosphino)palladium(0) (231 mg, 200 µmol) in 50 mL dioxane with heating to reflux for 2 d gives 1.21 g brown oil. Purify the crude product by column chromatography, eluting with 98:2 dichloromethane:methanol to obtain (E)-4-(2-cyclopentyl-1-hydroxymethyl-vinyl)-N-pyridin-3-ylmethyl-benzenesulfonamide (800 mg) as a colorless oil. MS (m/e): 373 (M+H).

c: (d)-(E)4-(2-Cyclopentyl-1-hydroxy:methyl-cyclopropyl)-N-pyridin-3-ylmethyl-benzenesulfonamide According to the procedure described for example 26c the use of crude (E)-4-(2-cyclopentyl-1-hydroxymethyl-vinyl)-N-pyridin-3-ylmethyl-benzenesulfonamide (330 mg, 887 µmol), diiodomethane (2.38 g, 8.87 mmol) and diethylzinc (4.0 mL, 4.40 mmol) in 50 mL toluene and 50 mL dichloromethane with heating to 60° C. for 2 d and threefold repetition of reagent addition using the same amounts gives 8.35 g brown oil. Purify the crude product by column chromatography, eluting with a gradient from 100:0 to 98:2 dichloromethane:7 M NH₃ in methanol to obtain (±)-(E)-4-(2-cyclopentyl-1-hydroxymethyl-cyclopropyl)-N-pyridin-3-ylmethyl-benzenesulfonamide (307 mg) as a yellow oil. MS (m/e): 387 (M+H).

d: (±)-(E)-2-Cyclopentyl-1-{4-[(pyridin-3-ylmethyl)-sulfamoyl]-phenyl}-cyclopropanecarboxylic acid According to the procedure described for example 26e the use of (±)-(E)-4-(2-cyclopentyl-1-hydroxymethyl-cyclopropyl)-N-pyridin-3-ylmethyl-benzenesulfonamide (80 mg, 207 µmol) and 2.7 M Jones reagent (303 µL, 828 µmol) and washing the organic extracts with an aqueous solution of citric acid gives crude (±)-(E)-2-cyclopentyl-1-{4-[(pyridin-3-ylmethyl)-sulfamoyl]-phenyl}-cyclopropanecarboxylic acid (242 mg) as a white solid, which contains some citric acid. Further purification is not necessary. MS (m/e): 401 (M+H).

e: (±)-(E)-2-Cyclopentyl-1-{4-[(pyridin-3-ylmethyl)-sulfamoyl]-phenyl}-cyclopropanecarboxylic acid thiazol-2-ylamide According to the procedure described for example 26f the use of crude (±)-(E)-2-cyclopentyl-1-{4-[(pyridin-3-ylmethyl)-sulfamoyl]-phenyl}-cyclopropanecarboxylic acid (242 mg, max. 207 µmol), TBTU (642 mg, 2.0 mmol), triethylamine (405 µL, 4.0 mmol) and 2-aminothiazole (200 mg, 2.0 mmol) gives crude (±)-(E)-2-cyclopentyl-1-{4-[(pyridin-3-ylmethyl)-sulfamoyl]-phenyl}-cyclopropanecarboxylic acid thiazol-2-ylamide (15 mg) as a colorless oil. Purify this material via preparative HPLC, eluting with a gradient from 100:0 to 0:100 water (+0.1% TFA):acetonitrile to afford the title compound as TFA salt (11 mg). ¹H-NMR (CDCl₃) δ=0.82-0.96 (m, 1H), 1.24-1.88 (m, 10H), 2.13-2.25 (m, 1H), 4.35 (mc, 2H), 6.60 (mc, 1H), 7.00-7.95 (m, 7H), 8.38 (mc, 1H), 8.67 (mc, 1H), 8.90 (mc, 1H). MS (m/e): 483 (M+H).

EXAMPLE 29

(±)-(E)-2-Cyclopentyl-1-(4-methanesulfonyl-phenyl)-cyclopropanecarboxylic acid thiazol-2-ylamide

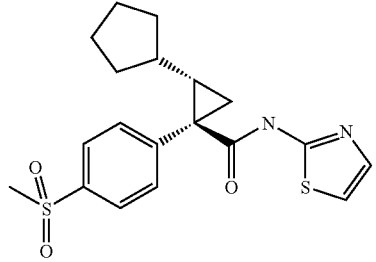

a: (E)-3-Cyclopentyl-2-(4-methanesulfonyl-phenyl)-prop-2-en-1-ol

According to the procedure described for example 16e the use of (E)-3-cyclopentyl-2-(4-methanesulfonyl-phenyl)-acrylic acid ethyl ester (500 mg, 1.55 mmol) and a 1.4 M solution of DIBAL in toluene (5.5 mL, 7.75 mmol) gives after column chromatography, eluting with a gradient from 100:0 to 0:100 hexanes:ethyl acetate the title compound (446 mg) as a colorless oil. ¹H-NMR (CDCl₃) δ=1.15-1.70 (m, 8H), 2.20-2.37 (m, 1H), 3.00 (s, 3H), 4.26 (s, 2H), 5.65 (d, 1H, 10 Hz), 7.37 (mc, 2H), 7.86 (mc, 2H).

b: (±)-(E)-[2-Cyclopentyl-1-(4-methanesulfonyl-phenyl)-cyclopropyl]-methanol According to the procedure described for 54f the use of (E)-3-cyclopentyl-2-(4-methanesulfonyl-phenyl)-prop-2-en-1-ol (370 mg, 1.25 mmol), a 1 M solution of diethylzinc in hexanes (6.2 mL, 6.2 mmol) and diiodomethane (1.0 mL, 12.4 mmol) in toluene gives after column chromatography, eluting with a gradient from 2:1 to 1:1 hexanes:ethyl acetate (±)-(E)-[2-cyclopentyl-1-(4-methanesulfonyl-phenyl)-cyclopropyl]-methanol (260 mg) as a colorless oil. $^1$H-NMR (CDCl$_3$) δ=0.72-1.70 (m, 12H), 3.06 (s, 3H), 3.43 (mc, 1H), 3.89 (mc, 1H), 7.57 (mc, 2H), 7.59-(mc, 2H).

c: (±)-(E)-2-Cyclopentyl-1-(4-methanesulfonyl-phenyl)-cyclopropanecarboxylic acid Add a 2.7-M solution of Jones reagent (1.8 mL, 4.86 mmol) to a solution of (±)-(E)-[2-cyclopentyl-1-(4-methanesulfonyl-phenyl)-cyclopropyl]-methanol (260 mg, 0.88 mmol) in 18 mL acetone at 0° C. and stir at r.t. for 2 h. Add iso-propanol (0.4 mL), stir at r.t. for 30 min, add water and extract with TBME. Dry the combined organic extracts over MgSO$_4$, filtrate and concentrate under reduced pressure to obtain (±)-(E)-2-cyclopentyl-1-(4-methanesulfonyl-phenyl)-cyclopropanecarboxylic acid (240 mg), which were sufficiently pure for further conversions. MS (m/e): 307 (M−H).

d: (±)-(E)-2-Cyclopentyl-1-(4-methanesulfonyl-phenyl)-cyclopropanecarboxylic acid thiazol-2-ylamide According to the procedure described for 26f the use of (±)-(E)-2-cyclopentyl-1-(4-methanesulfonyl-phenyl)-cyclopropanecarboxylic acid (140 mg, 454 μmol), TBTU (146 mg, 454 μmol), triethylamine (92.0 mg, 908 μmol) and 2-aminothiazole (50.0 mg, 500 μmol) gives (±)-(E)-2-cyclopentyl-1-(4-methanesulfonyl-phenyl)-cyclopropanecarboxylic acid thiazol-2-ylamide (112 mg) as a colorless wax. $^1$H-NMR (CDCl$_3$) δ=1.33-1.73 (m, 10 H), 1.84 (mc, 1H), 2.17 (mc, 1H), 3.18 (s, 3 H), 6.96 (mc, 1H), 7.36 (mc, 1), 7.65 (mc, 2H), 8.03 (mc, 2H). MS (m/e): 391 (M+H).

EXAMPLE 30

Separation of (±)-(E)-2-Cyclopentyl-1-(4-methanesulfonyl-phenyl)-cyclopropanecarboxylic acid thiazol-2-ylamide into its enantiomers (±)-(E)-2-Cyclopentyl-1-(4-methanesulfonyl-phenyl)-cyclopropanecarboxylic acid thiazol-2-ylamide can be separated into its enantiomers via chromatography on a Chiralpak AD_column, eluting with hexane TFA 0.05%/ethanol 30:70. Under the conditions given the first enantiomer to elute is enantiomer 1.

EXAMPLE 31

(±)-(E)-2,2-Dichloro-3-cyclopentyl-1-(4-methanesulfonyl-phenyl)-cyclopropanecarboxylic acid thiazol-2-ylamide

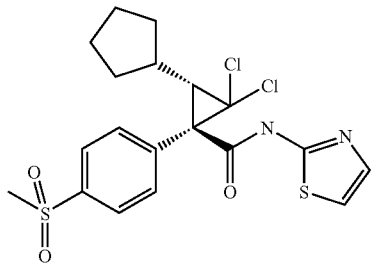

a: (=)-(E)-2,2-Dichloro-3-cyclopentyl-1-(4-methanesulfonyl-phenyl)-cyclopropanecarboxylic acid ethyl ester Add successively tetrabutyl ammonium bromide (10 mg, 31 μmol) and 48% sodium hydroxide solution (2.5 mL, 31 mmol) to a solution of (E)-3-cyclopentyl-2-(4-methanesulfonyl-phenyl)-acrylic acid ethyl ester (200 mg, 621 μmol) in 3 mL chloroform and stir at r.t. for 2 d. Acidify to pH=1 with conc. hydrochloric acid, extract with dichloromethane, wash the combined organic extracts with brine and dry them over sodium sulfate. Filtration and concentration give crude (±)-(E)-2,2-dichloro-3-cyclopentyl-1-(4-methanesulfonyl-phenyl)-cyclopropanecarboxylic acid ethyl ester (182 mg) as a brown oil, which is sufficiently pure for further conversions. MS (m/e): 405 [($^{35}$Cl$^{35}$Cl)M+H)], 407 [($^{35}$Cl$^{37}$Cl)M+H)].

b: (±)-(E)-2,2-Dichloro-3-cyclopentyl-1-(4-methanesulfonyl-phenyl)-cyclopropanecarboxylic acid Add 2 M aqueous sodium hydroxide solution (6 mL) to a solution of (±)-(E)-2,2-dichloro-3-cyclopentyl-1-(4-methanesulfonyl-phenyl)-cyclopropanecarboxylic acid ethyl ester (182 mg, max. 444 μmol) in 20 mL ethanol and stir at r.t. for 5 h. Acidify with 1 M aqueous hydrogen choride solution to pH=4, extract with ethyl acetate, wash organic extracts with brine, dry over sodium sulfate, filtrate and concentrate under reduced pressure to obtain crude (±)-(E)-2,2-dichloro-3-cyclopentyl-1-(4-methanesulfonyl-phenyl)-cyclopropanecarboxylic acid (100 mg) as a brown oil, which can be directly used for further conversions.

c: (±)-(E)-2,2-Dichloro-3-cyclopentyl-1-(4-methanesulfonyl-phenyl)-cyclopropanecarboxylic acid thiazol-2-ylamide According to the procedure described for 26f the use of crude (±)-(E)-2,2-dichloro-3-cyclopentyl-1-(4-methanesulfonyl-phenyl)-cyclopropanecarboxylic acid (100 mg, max. 306 μmol), TBTU (98.1 mg, 306 μmol), triethylamine (86 μL, 612 μmol) and 2-aminothiazole (33.8 mg, 306 μmol) gives (±)-(E)-2,2-dichloro-3-cyclopentyl-1-(4-methanesulfonyl-phenyl)-cyclopropanecarboxylic acid thiazol-2-ylamide (34 mg) as yellow crystals. $^1$H-NMR (CDCl$_3$) δ=1.29-2.04 (m, 10 H), 3.05 (s, 3 H), 6.94 (mc, 1H), 7.34 (mc, 1H), 7.70 (mc, 2H), 7.98 (mc, 2H). MS (m/e): 459 [($^{35}$Cl$^{35}$Cl)M+H)], 461 [($^{35}$Cl$^{37}$Cl)M+H)].

EXAMPLE 32

(±)-(E)-3-Cyclopentyl-2,2-difluoro-1-(4-methanesulfonyl-phenyl)-cyclopropanecarboxylic acid thiazol-2-ylamide

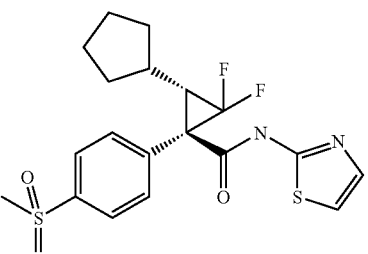

a: (±)-(E)-3-Cyclopentyl-2,2-difluoro-1-(4-methanesulfonyl-phenyl)-cyclopropanecarboxylic acid ethyl ester Add a solution of chlorodifluoroacetic acid sodium salt (5.0 g, 32.8 mmol) in 23 mL diglyme at 180° C. to a solution of (E)-3-cyclopentyl-2-(4-methanesulfonyl-phenyl)-acrylic acid ethyl ester (200 mg, 621 μmol) in 5 mL diglyme over a period of 3 h and stir at reflux for 16 h. Filter the resulting suspension, wash the filter with ethyl acetate and concentrate to remove most organic solvents. Purify the resulting solution of the reaction products in diglyme by filtration through a short pad of reversed phase silica, eluting with a gradient from 80:20 to 30:70 water:acetonitrile to obtain a mixture (250 mg) of (±)-(E)-3-cyclopentyl-2,2-difluoro-1-(4-methanesulfonyl-phenyl)-cyclopropanecarboxylic acid ethyl ester and unreacted (E)-3-cyclopentyl-2-(4-methanesulfonyl-phenyl)-acrylic acid ethyl ester. It is not necessary to further purify the title compound. MS (m/e): 373 (M+H).

b: (±)-(E)-3-Cyclopentyl-2,2-difluoro-1-(4-methane-sulfonyl-phenyl)-cyclopropanecarboxylic acid thiazol-2-ylamide Add a 2 M solution of iso-propyl magnesium chloride in THF (310 µL, 620 µmol), at −35° C. to a solution of 2-aminothiazole (62.0 mg, 620 µmol) in 2.5 mL THF, warm slowly to r.t. during 45 min and cool back to −35° C. Add a solution of (E)-3-cyclopentyl-2-(4-methanesulfonyl-phenyl)-acrylic acid ethyl ester and (±)-(E)-3-cyclopentyl-2,2-difluoro-1-(4-methanesulfonyl-phenyl)-cyclopropanecarboxylic acid ethyl ester (240 mg, max. 620 µmol) as obtained in example 32a in 5 mL THF, stir at 50° C. for 16 h, add 5 mL saturated ammonium chloride solution and extract with ethyl acetate. Wash the combined organic extracts with brine and dry them over sodium sulfate. Filtrate, concentrate and purify the resulting brown oil by column chromatography, eluting with a gradient from 100:0 to 30:70 hexanes:ethyl acetate to obtain (±)-(E)-3-dyclopentyl-2,2-difluoro-1-(4-methanesulfonyl-phenyl)-cyclopropanecarboxylic acid thiazol-2-ylamide (25 mg) as a yellow oil which slowly crystallizes upon standing at ambient temperature. $^1$H-NMR (CDCl$_3$) δ=1.21-1.88 (m, 10 H), 3.14 (s, 3 H), 7.00 (mc, 1H), 7.38 (mc, 1H), 7.67 (mc, 2H), 8.04 (mc, 2H). MS (m/e): 427 (M+H).

EXAMPLE 33

Separation of (±)-(E)-3-Cyclopentyl-2,2-difluoro-1-(4-methanesulfonyl-phenyl)-cyclopropanecarboxylic acid thiazol-2-ylamide into its enantiomers (±)-(E)-3-Cyclopentyl-2,2-difluoro-1-(4-methanesulfonyl-phenyl)-cyclopropanecarboxylic acid thiazol-2-ylamide can be separated into its enantiomers via chromatography on a Chiralpak AD_column, eluting with hexane TFA 0.05%/iso-propanol 80:20. Under the conditions given the first enantiomer to elute is enantiomer 1.

EXAMPLE 34

(±)-(E)-2-Cyclohexyl-1-(4-fluoro-phenyl)-cyclopropanecarboxylic acid thiazol-2-ylamide

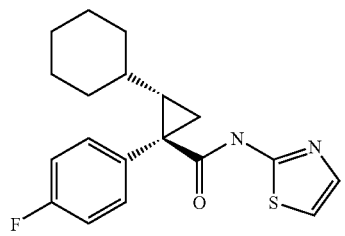

a: (E)-3-Cyclohexyl-2-(4-fluoro-phenyl)-prop-2-en-1-ol

According to the procedure described for example 26b the use of 1-bromo-4-fluoro-benzene (875 mg, 5.0 mmol), (E)-3-cyclohexyl-2-(4,4,5,5-tetramethyl-[1,3,2]dioxaborolan-2-yl)-prop-2-en-1-ol (1.60 g, 6.00 mmol), caesium fluoride (2.28 g, 15.0 mmol) and tetrakis(triphenylphosphino)palladium(0) (577 mg, 500 µmol) in 40 mL dioxane and 4 mL water with heating to reflux for 3 h gives 1.26 g brown oil. Purify the crude product by column chromatography, eluting with a gradient from 100:0 to 60:40 hexanes:ethyl acetate to obtain (E)-3-cyclohexyl-2-(4-fluoro-phenyl)-prop-2-en-1-ol (641 mg) as a brown oil. MS (m/e): 217 [(M−H$_2$O)+H].

b: (:L)-(E)-[2-Cyclohexyl-1-(4-fluoro-phenyl)-cyclopropyl]-methanol

According to the procedure described for example 26c the use of (E)-3-cyclohexyl-2-(4-fluoro-phenyl)-prop-2-en-1-ol (641 mg, 2.74 mmol), diiodomethane (5.87 g, 21.9 mmol) and diethylzinc (10.0 mL, 11.0 mmol) in 40 mL toluene with heating to 60° C. for 16 h gives (±)-(E)-[2-cyclohexyl-1-(4-fluoro-phenyl)-cyclopropyl]-methanol (503 mg) as a white solid after column chromatography, eluting with a gradient from 100:0 to 75:25 hexanes:ethyl acetate. MS (m/e): 231 [(M−H$_2$O)+H].

c: (±)-(E)-2-Cyclohexyl-1-(4-fluoro-phenyl)-cyclopropanecarboxylic acid

According to the procedure described for example 26e the use of (±)-(E)-[2-cyclohexyl-1-(4-fluoro-phenyl)-cyclopropyl]-methanol (503 mg, 2.03 mmol) and 2.7 M Jones reagent (3.0 mL, 8.12 mmol) in 15 mL acetone gives crude (±)-(E)-2-cyclohexyl-1-(4-fluoro-phenyl)-cyclopropanecarboxylic acid (345 mg) as a white solid. Further purification is not necessary. MS (m/e): 261 (M−H).

d: (±)-(E)-2-Cyclohexyl-1-(4-fluoro-phenyl)-cyclopropanecarboxylic acid thiazol-2-ylamide According to the procedure described for 26f the use of crude (±)-(E)-2-cyclohexyl-1-(4-fluoro-phenyl)-cyclopropanecarboxylic acid (345 mg, max. 1.32 mmol), TBTU (1.06 g, 3.29 mmol), triethylamine (1.11 mL, 7.90 mmol) and 2-aminothiazole (329 mg, 3.29 mmol) gives (±)-(E)-2-cyclohexyl-1-(4-fluoro-phenyl)-cyclopropanecarboxylic acid thiazol-2-ylamide (316 mg) as a white solid after column chromatography, eluting with a gradient from 100:0 to 75:25 hexanes:ethyl acetate. $^1$H-NMR (CDCl$_3$) δ=0.27-0.42 (m, 1H), 0.87-1.27 (m, 6H), 1.49-1.72 (m, 5H), 1.82 (mc, 1H), 2.00 (mc, 1H), 6.92 (m, 1H), 7.10-7.18 (m, 2H), 7.32-7.43 (m, 3 H), 8.47 (b, 1H). MS (m/e): 345 (M+H).

EXAMPLE 35

(±)-(E)-2-Cyclohexyl-1-(3-methanesulfonyl-phenyl)-cyclopropanecarboxylic acid thiazol-2-ylamide

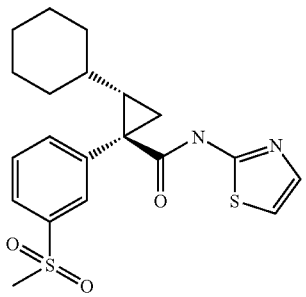

a: (E)-3-Cyclohexyl-2-(3-methanesulfonyl-phenyl)-prop-2-en-1-ol

1-Bromo-3-methanesulfonyl-benzene can be prepared according to *Tetrahedron Lett.* 1994, 35, 9063-9066.

According to the procedure described for example 26b the use of 1-bromo-3-methanesulfonyl-benzene (1.07 g, 4.55 mmol), (E)-3-cyclohexyl-2-(4,4,5,5-tetramethyl-[1,3,2]dioxaborolan-2-yl)-prop-2-en-1-ol (1.57 g, 5.92 mmol), caesium fluoride (2.07 g, 13.7 mmol) and tetrakis(triphenylphosphino)palladium(0) (525 mg, 455 µmol) in 40 mL dioxane with heating to reflux for 16 h gives a brown oil. Purify the crude product by column chromatography, eluting with a gradient from 100:0 to 0:100 hexanes:ethyl acetate to obtain (E)-3-cyclohexyl-2-(3-methanesulfonyl-phenyl)-prop-2-en-1-ol (693 mg) as a brown oil. MS (m/e): 277 [(M−H$_2$O)+H].

b: (±)-(E)-[2-Cyclohexyl-1-(3-methanesulfonyl-phenyl)-cyclopropyl]-methanol

According to the procedure described for example 26c the use of (E)-3-cyclohexyl-2-(3-methanesulfonyl-phenyl)-prop-2-en-1-ol (693 mg, 2.36 mmol), diiodomethane (6.32 g, 23.6 mmol) and diethylzinc (10.7 mL, 11.8 mmol) in 40 mL toluene with heating to 60° C. for 16 h gives (±)-(E)-[2-cyclohexyl-1-(3-methanesulfonyl-phenyl)-cyclopropyl]-methanol (578 mg) as a white solid after column chromatography, eluting with a gradient from 100:0 to 0:100 hexanes:ethyl acetate. MS (m/e): 291 [(M−H$_2$O)+H].

c: (±)-(E)-2-Cyclohexyl-1-(3-methanesulfonyl-phenyl)-cyclopropanecarboxylic acid According to the procedure described for example 26e the use of (±)-(E)-[2-cyclohexyl-1-(3-methanesulfonyl-phenyl)-cyclopropyl]-methanol (578 mg, 1.88 mmol) and 2.7 M Jones reagent (2.78 mL, 7.51 mmol) in 20 mL acetone gives crude (±)-(E)-2-cyclohexyl-1-(3-methanesulfonyl-phenyl)-cyclopropanecarboxylic acid (603 mg) as a white solid. Further purification is not necessary. MS (m/e): 321 (M−H).

d: (:L)-(E)-2-Cyclohexyl-1-(3-methanesulfonyl-phenyl)-cyclopropanecarboxylic acid thiazol-2-ylamide According to the procedure described for 26f the use of crude (±)-(E)-2-cyclohexyl-1-(3-methanesulfonyl-phenyl)-cyclopropanecarboxylic acid (603 mg, max. 1.88 mmol), TBTU (1.51 g, 4.70 mmol), triethylamine (1.59 mL, 11.3 mmol) and 2-aminothiazole (470 mg, 4.70 mmol) gives pure (±)-(E)-2-cyclohexyl-1-(3-methanesulfonyl-phenyl)-cyclopropanecarboxylic acid thiazol-2-ylamide (112 mg) as a white solid after column chromatography, eluting with a gradient from 100:0 to 20:80 hexanes:ethyl acetate. $^1$H-NMR (CDCl$_3$) δ=0.17-0.30 (m, 1H), 0.82-1.32 (m, 6H), 1.48-1.84 (m, 6H), 2.00-2.13 (m, 1H), 3.12 (s, 3H), 6.95 (m, 1H), 7.35 (m, 1H), 7.65-7.78 (m, 2H), 8.00 (mc, 2H). MS (m/e): 405 (M+H).

EXAMPLE 36

(±)-(E)-2-Cyclohexyl-1-(3-fluoro-4-methanesulfonyl-phenyl)-cyclopropanecarboxylic acid thiazol-2-ylamide

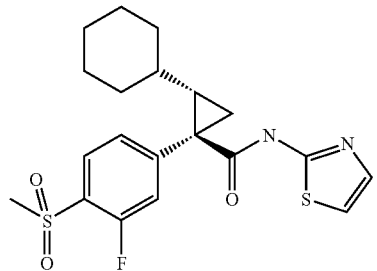

a: (4-Bromo-2-fluoro-phenylsulfanyl)-triisopropylsilane

Heat a solution of 4-bromo-2-fluoro-1-iodo-benzene (450 mg, 1.50 mmol) and potassium triisopropylthiolate (375 mg, 1.65 mmol) in 12 mL benzene and 3 mL THF to reflux for 3 h, cool to r.t., add 20 mL water and extract with diethylether. Dry the combined organic extracts over sodium sulfate, filtrate and concentrate under reduced pressure. Purify by column chromatography, eluting with hexanes to obtain (4-bromo-2-fluoro-phenylsulfanyl)-triisopropyl-silane (570 mg) as a colorless liquid. MS (m/e): 362 [($^{79}$Br)M], 364 [($^{81}$Br)M].

b: 4-Bromo-2-fluoro-1-methylsulfanyl-benzene

Add tetrabutylammonium fluoride trihydrate (546 mg, 1.73 mmol) to a mixture of (4-bromo-2-fluoro-phenylsulfanyl)-triisopropyl-silane (570 mg, 1.57 mmol) and potassium carbonate (650 mg, 4.71 mmol) in 20 mL THF and stir at r.t. for 1 h. Add methyl iodide, stir for 1 h and concentrate to remove THF. Add 20 mL water, extract with diethylether, dry the combined organic extracts over sodium sulfate, filtrate and concentrate under reduced pressure to obtain 4-bromo-2-fluoro-1-methylsulfanyl-benzene (347 mg) as a colorless liquid, which was used for following conversions without further purifications. MS (m/e): 220 [($^{79}$Br)M], 222 [($^{81}$Br)M].

c: 4-Bromo-2-fluoro-1-methanesulfonyl-benzene

According to the procedure described for 54d the use of oxone® (1.48 g, 1.57 mmol) in 15 mL water and 4-bromo-2-fluoro-1-methylsulfanyl-benzene (347 mg, 1.57 mmol) in 30 mL methanol after 22 h reaction time gives crude title compound as a white solid. Purify by column chromatography, eluting with a gradient from 100:0 to 20:80 hexanes:ethyl acetate to obtain 4-bromo-2-fluoro-1-methanesulfonyl-benzene (220 mg) as a white solid. $^1$H-NMR (CDCl$_3$) δ=3.21 (s, 3 H), 7.44-7.53 (m, 2H), 7.84 (mc, 1H).

d: (E)-3-Cyclohexyl-2-(3-fluoro-4-methanesulfonyl-phenyl)-prop-2-en-1-ol

Heat a mixture of 4-bromo-2-fluoro-1-methanesulfonyl-benzene (220 mg, 0.86 mmol), (E)-3-cyclohexyl-2-(4,4,5,5-tetramethyl-[1,3,2]dioxaborolan-2-yl)-prop-2-en-1-ol (298 mg, 1.12 mmol), potassium carbonate (356 mg, 2.58 mmol) and tetrakis(triphenylphosphino)palladium(0) (99 mg, 86 µmol) in 40 mL toluene, 5 mL iso-propanol and 5 mL water to reflux for 2 h. After cooling to r.t. extract with ethyl acetate, wash the combined organic extracts with brine, dry them over sodium sulfate, filtrate and concentrate to obtain a brown oil. Purify the crude product by column chromatography, eluting with a gradient from 100:0 to 0:100 hexanes:ethyl acetate to obtain (E)-3-cyclohexyl-2-(3-fluoro-4-methanesulfonyl-phenyl)-prop-2-en-1-ol (238 mg) as a pale yellow oil. MS (m/e): 295 [(M−H$_2$O)+H].

e: (±)-(E)-[2-Cyclohexyl--(3-fluoro-4-methanesulfonyl-phenyl)-cyclopropyl]-methanol According to the procedure described for example 26c the use of (E)-3-cyclohexyl-2-(3-fluoro-4-methanesulfonyl-phenyl)-prop-2-en-1-ol (238 mg, 763 µmol), diiodomethane (2.01 g, 7.63 mmol) and diethylzinc (3.47 mL, 3.81 mmol) in 25 mL toluene with heating to 60° C. for 16 h gives (±)-(E)-[2-cyclohexyl-1-(3-fluoro-4-methanesulfonyl-phenyl)-cyclopropyl]-methanol (121 mg) as a white solid after column chromatography, eluting with a gradient from 100:0 to 0:100 hexanes:ethyl acetate. MS (m/e): 309 [(M−H$_2$O)+H].

f: (±)-(E)-2-Cyclohexyl-1-(3-fluoro-4-methanesulfonyl-phenyl)-cyclopropanecarboxylic acid According to the procedure described for example 26e the use of (±)-(E)-[2-cyclohexyl-1-(3-fluoro-4-methanesulfonyl-phenyl)-cyclopropyl]-methanol (121 mg, 371 μmol) and 2.7 M Jones reagent (0.55 mL, 1.48 mmol) in 20 mL acetone gives crude (±)-(E)-2-cyclohexyl-1-(3-fluoro4-methanesulfonyl-phenyl)-cyclopropanecarboxylic acid (171 mg) as a green oil. Further purification is not necessary. MS (m/e): 358 (M+NH$_4$).

g: (±)-(E)-2-Cyclohexyl-1-(3-fluoro-4-methanesulfonyl-phenyl)-cyclopropanecarboxylic acid thiazol-2-ylamide According to the procedure described for 26f the use of crude (±)-(E)-2-cyclohexyl-1-(3-fluoro-4-methanesulfonyl-phenyl)-cyclopropanecarboxylic acid (171 mg, max. 375 μmol), TBTU (298 mg, 928 μmol), triethylamine (313 μL, 2.23 mmol) and 2-aminothiazole (93 mg, 928 μmol) gives pure (±)-(E)-2-cyclohexyl-1-(3-fluoro-4-methanesulfonyl-phenyl)-cyclopropanecarboxylic acid thiazol-2-ylamide (45 mg) as a yellow solid after column chromatography, eluting with a gradient from 100:0 to 30:70 hexanes:ethyl acetate. $^1$H-NMR (CDCl$_3$) δ=0.23-0.37 (m, 1H), 0.82-1.30 (m, 6H), 1.51-1.81 (m, 6H), 2.09 (mc, 1H), 3.32 (s, 3 H), 6.97 (mc, 1H), 7.25-7.46 (m, 3 H), 8.05 (mc, 1H), 8.44 (b, 1H). MS (m/e): 423 (M+H).

EXAMPLE 37

(±)-(E)-2-Cyclopentyl-1-14-(3-imidazol-1-yl-propyl-sulfamoyl)-phenyl]-cyclopropanecarboxylic acid thiazol-2-ylamide

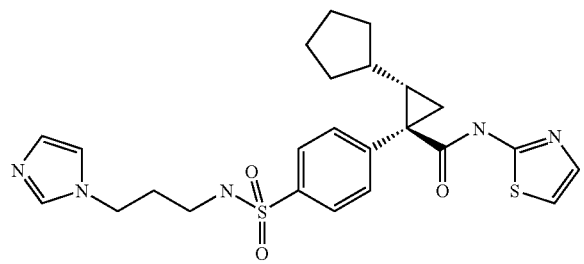

a: (E)-2-(4-Bromo-phenyl)-3-cyclopentyl-prop-2-en-1-ol

According to the procedure described for example 26b the use of 4-bromo-1-iodo-benzene (1.42 g, 5.0 mmol), (E)-3-cyclopentyl-2-(4,4,5,5-tetramethyl-[1,3,2]dioxaborolan-2-yl)-prop-2-en-1-ol (1.01 g, 4.00 mmol), caesium fluoride (2.28 g, 15.0 mmol) and tetrakis(triphenylphosphino)palladium(0) (577 mg, 500 μmol) in 120 mL THF with heating to 60° C. for 16 h gives a brown oil. Purify the crude product by column chromatography, eluting with a gradient from 100:0 to 60:40 hexanes:ethyl acetate to obtain (E)-2-(4-bromo-phenyl)-3-cyclopentyl-prop-2-en-1-ol (446 mg) as a yellow oil. MS (m/e): 263 {[($^{79}$Br)M–H$_2$O]+H}, 265 {[($^{81}$Br)M–H$_2$O]+H}.

b: (±)-(E)-[1-(4-Bromo-phenyl)-2-cyclopentyl-cyclopropyl]-methanol

According to the procedure described for example 26c the use of (E)-2-(4-bromo-phenyl)-3-cyclopentyl-prop-2-en-1-ol (446 mg, 1.59 mmol), diiodomethane (3.40 g, 12.7 mmol) and diethylzinc (5.77 mL, 6.35 mmol) in 25 mL toluene with heating to 60° C. for 16 h gives (±)-(E)-[1-(4-bromo-phenyl)-2-cyclopentyl-cyclopropyl]-methanol (356 mg) as a yellow oil after column chromatography, eluting with a gradient from 100:0 to 70:30 hexanes:ethyl acetate. MS (m/e): 277 {[($^{79}$Br)M–H$_2$O]+H}, 279 {[($^{81}$Br)M–H$_2$O]+H}.

c: (±)-(E)-1-(4-Bromo-phenyl)-2-cyclopentyl-cyclopropanecarboxylic acid

According to the procedure described for example 26e the use of (±)-(E)-[1-(4-bromo-phenyl)-2-cyclopentyl-cyclopropyl]-methanol (356 mg, 1.21 mmol) and 2.7 M Jones reagent (1.78 mL, 4.83 mmol) in 10 mL acetone gives crude (±)-(E)-1-(4-bromo-phenyl)-2-cyclopentyl-cyclopropanecarboxylic acid (345 mg) as a white solid. Further purification is not necessary. MS (m/e): 307 [($^{79}$Br)M–H], 309 [($^{81}$Br)M–H].

d: (±)-(E)-2-Cyclopentyl-1-(4-mercapto-phenyl)-cyclopropanecarboxylic acid

Add sodium thiomethylate (2.44 g, 34.8 mmol) in four equal portions every 2 h at 150° C. to a solution of (±)-(E)-1-(4-bromo-phenyl)-2-cyclopentyl-cyclopropanecarboxylic acid (355 mg, 1.15 mmol) in 15 mL DMA and stir at that temperature for 16 h. Cool to r.t., add 1 M hydrochloric acid solution to adjust the pH to 1. Extract with ethyl acetate, wash the combined org. extracts twice with water and then with brine. Dry the organic phase over sodium sulfate, filtrate and concentrate to obtain crude (±)-(E)-2-cyclopentyl-1-(4-mercapto-phenyl)-cyclopropanecarboxylic acid (290 mg) as a yellow oil, which can be used for further reactions without any purification. MS (m/e): 261 (M–H).

e: (±)-(E)-2-Cyclopentyl-1-(4-mercapto-phenyl)-cyclopropanecarboxylic acid methyl ester Add concentrated sulfuric acid (1.5 mL) to a solution of (±)-(E)-2-cyclopentyl-1-(4-mercapto-phenyl)-cyclopropanecarboxylic acid (290 mg, max. 1.15 mmol) as obtained from example 37d in 40 mL methanol and stir at r.t. for 16 h. Concentrate to remove methanol, add 20 mL water and extract with ethyl acetate. Wash the combined organic extracts with brine, dry them over sodium sulfate, filtrate and concentrate to obtain crude (±)-(E)-2-cyclopentyl-1-(4-mercapto-phenyl)-cyclopropanecarboxylic acid methyl ester (273 mg) as a yellow oil, which can be used for further reactions without any purification. MS (m/e): 277 (M–H).

f: (±)-(E)-1-(4-Chlorosulfonyl-phenyl)-2-cyclopentyl-cyclopropanecarboxylic acid methyl ester Add successively potassium nitrate (506 mg, 5.0 mmol) and sulfuryl chloride (674 mg, 5.0 mmol) to a solution of crude (:E)-(E)-2-cyclopentyl-1-(4-mercapto-phenyl)-cyclopropanecarboxylic acid methyl ester (273 mg, max. 1.0 mmol) in 20 mL acetonitrile and stir at r.t. for 3 h. Add saturated sodium bicarbonate solution and extract with ethyl acetate. Wash the combined organic extracts with brine, dry them over sodium sulfate, filtrate and concentrate. Purify the residue by column chromatography, eluting with a gradient from 100:0 to 75:25 hexanes:ethyl acetate to obtain (±)-(E)-1-(4-chlorosulfonyl-phenyl)-2-cyclopentyl-cyclopropanecarboxylic acid methyl ester (164 mg) as a white solid. MS (m/e): 343 (M+H).

g: (±)-(E)-2-Cyclopentyl-1-[4-(3-imidazol-1-yl-propylsulfamoyl)-phenyl]-cyclopropanecarboxylic acid methyl ester According to the procedure described for example 26a the use of (±)-(E)-1-(4-chlorosulfonyl-phenyl)-2-cyclopentyl-cyclopropanecarboxylic acid methyl ester (90 mg, 263 μmol) in 6 mL dichloromethane and 3-imidazol-1-yl-propylamine (33 mg, 263 μmol) and triethylamine (37 μL, 263 μmol) in 4 mL dichloromethane gives (±)-(E)-2-cyclopentyl-1-[4-(3-imidazol-1-yl-propylsulfamoyl)-phenyl]-cyclopropanecarboxylic acid methyl ester (96 mg) as a pale yellow oil. Further-purification is not necessary. MS (m/e): 432 (M+H).

h: (±)-(E)-2-Cyclopentyl-1-[4-(3-imidazol-1-yl-propylsulfamoyl)-phenyl]-cyclopropanecarboxylic acid thiazol-2-ylamide Add a 2 M solution of iso-propyl magnesium chloride in THF (0.5 mL, 1.0 mmol), at −20° C. to a solution of 2-aminothiazole (100 mg, 1.0 mmol) in 5 mL THF, warm slowly to r.t. during 1 h and cool back to −20° C. Add a solution of (±)-(E)-2-cyclopentyl-1-[4-(3-imidazol-1-yl-propylsulfamoyl)-phenyl]-cyclopropanecarboxylic acid methyl ester (96 mg, max. 222 μmol) as obtained in example 37 g in 5 mL THF, stir at 50° C. for 16 h, add 5 mL saturated ammonium chloride solution and extract with ethyl acetate. Wash the combined organic extracts with brine and dry them over sodium sulfate. Filtrate, concentrate and purify the resulting brown oil by column chromatography, eluting with a gradient from 100:0 to 0:100 hexanes:ethyl acetate to obtain (±)-(E)-2-cyclopentyl-1-[4-(3-imidazol-1-yl-propylsulfamoyl)-phenyl]-cyclopropanecarboxylic acid thiazol-2-ylamide (32 mg) as a light brown solid. $^1$H-NMR (CDCl$_3$) δ=0.73-0.86 (m, 1H), 1.26-1.47 (m, 5H), 1.53-1.68 (m, 4H), 1.78 (mc, 1H), 2.03 (mc, 2H), 2.14 (mc, 1H), 2.96 (mc, 2H), 4.09 (mc, 2H), 6.91 (b, 1H), 6.94 (mc, 1H), 7.06 (b, 1H), 7.31 (mc, 1H), 7.43.(b, 1H), 7.55 (mc, 2H), 7.83 (mc, 2H). MS (m/e): 500 (M+H).

EXAMPLE 38

(E)-2-Cyclohexyl-1-(4-methanesulfonyl-phenyl)-cyclopropanecarboxylic acid (5-fluoro-thiazol-2-yl)-amide

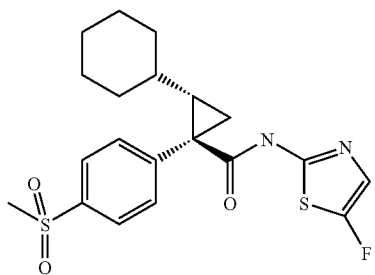

a: 2-(4-Bromo-phenyl)-3-cyclohexyl-acrylic acid ethyl ester

Add LHMDS in THF (451 mL, 1.0 M, 451 mmol) to a slurry of cyclohexylmethyl-triphenyl-phosphonium bromide (207.5 g, 472 mmol) in THF (500 mL) maintained at 0 ° C. and stir the mixture for 1 h. Dissolve (4-bromo-phenyl)-oxo-acetic acid ethyl ester (prepared as described by Hu, Shengkui; Neckers, Douglas C. *J. Org. Chem.* 1996, 61, 6407-6415.) in THF (40 mL) and add the resulting solution to the reaction mixture. Stir the reaction mixture for 60 h at room temperature. Dilute the mixture with water and neutralize with 1 N HCl. Evaporate the THF and add ether (700 mL). Stir at room temperature for 30 minutes and filter through celite®. Separate the layers and extract the aqueous layers with ether. Dry the combined organic layers over magnesium sulfate, filter, and concentrate. If large amounts of triphenylphosphine oxide are present, add ether (1 L), filter through celite® and concentrate the filtrate. Dissolve the brown oil in CH$_2$Cl$_2$ (50 mL) and filter through a pad of silica gel, eluting with a gradient of 0-5% EtOAc in hexanes to obtain the title compound (109.7 g) as an E/Z mixture (E/Z ratio: 2/1). MS (m/e): 337 (+H).

b: (E)-2-(4-Bromo-phenyl)-3-cyclohexyl-acrylic acid

Dissolve E/Z mixture of 2-(4-bromo-phenyl)-3-cyclohexyl-acrylic acid ethyl ester (158.9 g, 472 mmol) in methanol (800 mL) and add the solution to sodium methoxide in methanol (222 mL, 30%). Stir the reaction mixture at 50° C. for 72 h. Add water (17 mL) and 5 N aqueous sodium hydroxide solution (10 mL) and stir at 50° C. until all methyl ester is hydrolyzed (1-4,days). Add water and evaporate the methanol; Add ether (300 mL) and water (200 mL) and adjust the pH to a value of 1 with 1 N HCl. Separate the layers and extract the aqueous layer with ether. Dry the combined organic layers organic phase over sodium sulfate, filter and concentrate. Recrystallization of the residue in EtOAc affords the title compound as a white solid (93.3 g). MS (m/e): 309 (M+H).

c: (E)-2-(4-Bromo-phenyl)-3-cyclohexyl-prop-2-en-1-ol

Add DIBAL in toluene (673 mL, 1.0 M, 673 mmol) to a solution of (E)-2-(4-bromo-phenyl)-3-cyclohexyl-acrylic acid (52 g, 168 mmol) in toluene (1.6 l) maintained at −78° C. Then allow the reaction mixture to slowly warm to room temperature, and stir, it for 18 h. Cool reaction mixture to 0° C. and add MeOH to destroy excess amounts of DIBAL. Add Rochelle's salt (100 mL) and HCl (2 N). Separate the layers and wash the organic layer with brine. Filter through hydrophobic filter and concentrate to obtain the title compound (48.8 g) as a white solid. MS (m/e): 277 (M+H−H$_2$O).

d: (±)-(E)-[1-(4-Bromo-phenyl)-2-cyclohexyl-cyclopropyl]-methanol

Add a solution of diethylzinc in toluene (597 mL, 1.1 M, 657 mmol) to a solution of (E)-2-(4-bromo-phenyl)-3-cyclohexyl-prop-2-en-1-ol (48.8 g, 165 mmol) in toluene (1.4 L). Warm the reaction mixture to 60° C., and then add diiodomethane (106 mL, 1.312 mol) dropwise. Stir the reaction mixture for 20 h at 60° C. and then allow the mixture to cool to room temperature. Wash the mixture first with 1 N HCl, then with saturated aqueous sodium bicarbonate and with brine. Dry the organic phase over sodium sulfate, filter and, concentrate. Triturate the residue with hexanes to obtain the title compound (53.5 g) as a white solid. MS (m/e): 291 (M+H−H$_2$O).

e: Separation of (±)-(E)-[1-(4-Bromo-phenyl)-2-cyclohexyl-cyclopropyl]-methanol into its enantiomers (±)-(E)-[1-(4-Bromo-phenyl)-2-cyclohexyl-cyclopropyl]-methanol can be separated into its enantiomers via chromatography on a Novasep 80 mm ID column, eluting with 100% ACN+0.3% DMEA. Under the conditions given, the first enantiomer to elute is enantiomer 1, (E)-[1-(4-bromo-phenyl)-2-cyclohexyl-cyclopropyl]-methanol, and the second is enantiomer 2, (E)-[1-(4-bromo-phenyl)-2-cyclohexyl-cyclopropyl]-methanol. Mass spectral data for the enantiomers are identical to those of the racemate described in example 38d.

f: (E)-1-(4-Bromo-phenyl)-2-cyclohexyl-cyclopropanecarboxylic acid

Add concentrated sulfuric acid (24 mL) to a solution of chromium oxide (26.6 g) in water (25 mL), and then dilute the resulting solution with water to a total volume of 100 mL. Add these 100 mL dropwise to a solution of (E)-[1-(4-bromo-phenyl)-2-cyclohexyl-cyclopropyl]-methanol (enantiomer 1 as obtained in example 38e, 21 g, 68 mmol) in acetone (1.6 L). Stir the reaction mixture for 3 h at room temperature. Dilute with water to dissolve all the chromium (III) salts, and neutralize the solution with saturated aqueous sodium bicarbonate. Extract the solution with ethyl acetate. Dry the combined organic extracts with sodium sulfate, filter and concentrate to obtain the title compound (19.7 g) as a white solid. MS (m/e): 323 (M+H).

g: (E)-2-Cyclohexyl-1-(4-mercapto-phenyl)-cyclopropanecarboxylic acid

Add 10 mL DMA to a mixture of (E)-1-(4-bromo-phenyl)-2-cyclohexyl-cyclopropanecarboxylic acid (2.0 g, 6.19 mmol) and sodium thiomethylate (5.0 g, 71.4 mmol) and heat to 150° C. for 16 h. Cool back to r.t. and bring carefully to pH=1 with 2 M hydrochloric acid. Extract with ethyl acetate, wash the organic phase with 0.5 M hydrochloric acid and brine and dry the organic phase over $Na_2SO_4$. Filtrate and concentrate under reduced pressure to obtain crude (E)-2-cyclohexyl-1-(4-mercapto-phenyl)-cyclopropanecarboxylic acid (1.93 g) as a yellow oil, which can be used for ether conversions without purification. MS (m/e): 275 (M−H).

h: (E)-2-Cyclohexyl-1-(4-mercapto-phenyl)-cyclopropanecarboxylic acid methyl ester Add 15 mL conc. sulfuric acid to a solution of crude (E)-2-cyclohexyl-1-(4-mercapto-phenyl)-cyclopropanecarboxylic acid (3.87 g, 12.4 mmol) in 150 mL methanol and stir at r.t. for 16 h. Concentrate to remove most methanol, add water and extract with ethyl acetate. Wash the combined organic extracts with brine, dry them over $Na_2SO_4$, filtrate and concentrate to obtain crude (E)-2-cyclohexyl-1-(4-mercapto-phenyl)-cyclopropanecarboxylic acid methyl ester (3.86 g) as a yellow solid, which can be used for further conversions without purification. MS (m/e): 291 (M+H).

i: (E)-2-Cyclohexyl-1-(4-methylsulfanyl-phenyl)-cyclopropanecarboxylic acid methyl ester Add $K_2CO_3$ (414 mg, 3.0 mmol) to a solution of (E)-2-cyclohexyl-1-(4-mercapto-phenyl)-cyclopropanecarboxylic acid methyl ester (290 mg, 1.0 mmol) in 10 mL acetone. Add iodomethane (199 mg, 1.4 mmol, 88 µmol) and stir at r.t. for 30 min. Concentrate to remove acetone, add water and extract with ethyl acetate. Wash the combined organic extracts with brine, dry them over $Na_2SO_4$, filtrate and concentrate to obtain (E)-2-cyclohexyl-1-(4-methylsulfanyl-phenyl)-cyclopropanecarboxylic acid methyl ester (285 mg) as a yellow oil, which can be used for further conversions without purification. MS (m/e): 305 (M+H).

j: (E)-2-Cyclohexyl-1-(4-methanesulfonyl-phenyl)-cyclopropanecarboxylic acid methyl ester Add a solution of oxone® (1.84 g, 3.0 mmol) in 15 mL water to a solution of (E)-2-cyclohexyl-1-(4-methylsulfanyl-phenyl)-cyclopropanecarboxylic acid methyl ester (285 mg, 0.94 mmol) in 20 mL methanol and stir at r.t. for 90 min. Concentrate to remove methanol, add water and extract with ethyl acetate. Wash the combined organic extracts with brine, dry them over $Na_2SO_4$, filtrate and concentrate to obtain (E)-2-cyclohexyl-1-(4-methanesulfonyl-phenyl)-cyclopropanecarboxylic acid methyl ester (263 mg) as a white solid, which can be used for further conversions without purification. MS (m/e): 337 (M+H).

k: (E)-2-Cyclohexyl-1-(4-methanesulfonyl-phenyl)-cyclopropanecarboxylic acid Add 5 mL 1 M sodium hydroxide to a solution of (E)-2-cyclohexyl-1-(4-methanesulfonyl-phenyl)-cyclopropanecarboxylic acid methyl ester (263 mg, 0.78 mmol) in 5 mL methanol and stir at r.t. for 16 h. Concentrate to remove methanol, add water, bring to pH=1 with conc. hydrochloric acid and extract with ethyl acetate. Wash the combined organic extracts with brine, dry them over $Na_2SO_4$, filtrate and concentrate to obtain (E)-2-cyclohexyl-1-(4-methanesulfonyl-phenyl)-cyclopropanecarboxylic acid (245 mg) as a yellow oil, which can be used for further conversions without purification. MS (m/e): 321 (M−H).

l: (E)-2-Cyclohexyl-1-(4-methanesulfonyl-phenyl)-cyclopropanecarboxylic acid (5-fluoro-thiazol-2-yl)-amide Add 6 mL TFA to a solution of (5-fluoro-thiazol-2-yl)-carbamic acid tert-butyl ester (654 mg, 3.0 mmol) in 10 mL dichloromethane and stir at ambient temperature for 14 h. Concentrate to remove all organic solvents to obtain 2-amino-5-fluorothiazole (TFA salt) as a brown oil. Add 10 mL THF and 1 mL triethylamine to obtain "solution A".

Add TBTU (803 mg, 2.5 mmol) and 1 mL triethylamine to a solution of (E)-2-cyclohexyl-1-(4-methanesulfonyl-phenyl)-cyclopropanecarboxylic acid (245 mg, 761 µmol) in 10 mL THF and stir at r.t. for 30 min. Add "solution A" and warm to 55° C. for 16 h. Concentrate to remove THF, add water and extract with EtOAc. Wash combined organic extracts with brine, dry organic phase over $Na_2SO_4$, filtrate and concentrate. Purify the resulting brown oil by column chromatography, eluting with a gradient from 100:0 to 60:40 hexanes:EtOAc to obtain crude (E)-2-cyclohexyl-1-(4-methanesulfonyl-phenyl)-cyclopropanecarboxylic acid (5-fluoro-thiazol-2-yl)-amide (272 mg) as a yellow oil. Further purify this material via preparative HPLC, eluting with a gradient from 100:0 to 0:100 water (+0.1% TFA):acetonitrile to afford the title compound as a white solid. Dissolve this solid in dichloromethane and wash with saturated $NaHCO_3$ solution. Wash organic phase with brine, dry over $Na_2SO_4$, filtrate and concentrate to obtain pure (E)-2-cyclohexyl-1-(4-methanesulfonyl-phenyl)-cyclopropanecarboxylic acid (5-fluoro-thiazol-2-yl)-amide (51 mg) as a brown solid. $^1$H-NMR (CDCl$_3$) δ=0.17-0.32 (m, 1H), 0.83-1.32 (m, 6H), 1.50-1.81 (m, 6H), 2.05 (mc, 1H), 3.16 (s, 3H), 6.93 (mc, 1H), 7.63 (mc, 2H), 8.04 (mc, 2H). MS (m/e): 423 (M+H).

EXAMPLE 39

(±)-(E)-2-Cyclopentyl-1-[4-(pyridin-3-ylmethane-sulfonyl)-phenyl]-cyclopropanecarboxylic acid (5-chloro-thiazol-2-yl)-amide

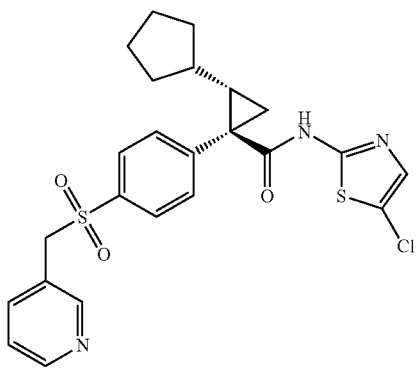

a: 3-(4-Bromo-phenylsulfanylmethyl)-pyridine

Following method of example 9a, reaction of 4-bromobenzenethiol (4.8 g, 24.1 mmol) with hydrobromic acid salt of 3-bromomethyl-pyridine (6.9 g, 26.5 mmol) and potassium carbonate (7.3 g, 53 mmol) in 91 ml acetone gives the title compound as a yellow solid (5.8 g). MS (m/e): 281 (M+H).

b: (E)-3-Cyclopentyl-2-[4-(pyridin-3-ylmethylsulfanyl)-phenyl]-acrylic acid ethyl ester Following the method of example 6a, reaction of potassium acetate (1.1 g, 10.7 mmol), 4,4,5,5,4',4',5',5'-octamethyl-[2,2']bi[[1,3,2]dioxaborolanyl] (1 g, 3.9 mmol), dichloro[1,1'-bis(diphenylphosphino)ferrocene]palladium (II) dichloromethane adduct (0.28 g, 0.35 mmol) and 3-(4-bromo-phenylsulfanylmethyl)-pyridine (1 g, 3.6 mmol) in DMF (8.9 ml), stirred for 2.5 h at 80° C., and addition of (Z)-2-bromo-3-cyclopentyl-acrylic acid ethyl ester (1.8 g, 7.1 mmol), dichloro[1,1'-bis(diphenylphosphino)ferrocene]palladium (II) dichloromethane adduct (0.14 g, 0.18 mmol) and 2 M aqueous sodium carbonate solution (8.9 ml), stirred at 80° C. over night affords the title compound as a yellow oil (0.8 g). MS (m/e): 368 (M+H).

c: (E)-3-Cyclopentyl-2-[4-(pyridin-3-ylmethanesulfonyl)-phenyl]-acrylic acid ethyl ester Add a suspension of oxone® (1.75 g, 2.8 mmol) in water (41 mL) to a solution of (E)-3-cyclopentyl-2-[4-(pyridin-3-ylmethylsulfanyl)-phenyl]-acrylic acid ethyl ester (0.8 g, 2.2 mmol) in methanol (124 mL) cooled to −20 ° C. Then allow the reaction mixture to warm to r.t. Stir for 1.5 h, and then add water. Extract the resulting mixture with dichloromethane. Combine the extracts, wash them with saturated aqueous sodium chloride solution, filter through a hydrophobic filter paper, and remove the solvent under vacuum. Purify the resulting material via column chromatography on silica gel, eluting with a gradient from 100:0 to 40:60 hexane: ethyl acetate to afford the title compound as a white solid (0.54 g). MS (m/e): 400 (M+H).

d: (E)-3-Cyclopentyl-2-[4-(pyridin-3-ylmethane-sulfonyl)-phenyl]-prop-2-en-1-ol Following the method of example 54e, reduction of (E)-3-cyclopentyl-2-[4-(pyridin-3-ylmethanesulfonyl)-phenyl]-acrylic acid ethyl ester (2.43 g, 6.08 mmol) with DIBAL in toluene (12.61 mL, 15.2 mmol) gives the title compound as an amorphous solid (1.26 g).
MS (m/e): 358 (M+H).

e: (±)-(E)-{2-Cyclopentyl-1-[4-(pyridin-3-yl-methanesulfonyl)-phenyl]-cyclopropyl}-methanol Following the method of example 54f, using (E)-3-cyclopentyl-2-[4-(pyridin-3-ylmethanesulfonyl)-phenyl]-prop-2-en-1-ol (1.22 g, 3.40 mmol) and 18 h at 60° C. after the addition of diethylzinc in toluene (12.4 mL, 1.1 M in toluene, 13.67 mmol) and diiodomethane (1.10 mL, 13.67 mmol) and repetition twice of addition of diethylzinc in toluene (12.4 mL, 1.1 M in toluene, 13.67 mmol) and diiodomethane (1.10 mL, 13.67 mmol) after 18 h at 60° C. affords the title compound as an amorphous solid (650 mg). MS (m/e): 372 (M+H).

f: (±)-(E)-2-Cyclopentyl-1-[4-(pyridin-3-ylmethane-sulfonyl)-phenyl]-cyclopropanecarboxylic acid Following the method of example 54 g, using (±)-(E)-{2-cyclopentyl-1-[4-(pyridin-3-ylmethanesulfonyl)-phenyl]-cyclopropyl}-methanol (0.64 g, 1.72 mmol) and 1 h at 0° C. after the addition of the chromium oxide the reaction is stopped by addition of saturated sodium bicarbonate solution, extracted with ethyl acetate, crystallized by addition of TBME and ethyl acetate and gives the title compound as a gray solid (480 mg). MS (m/e): 386 (M+H).

g: (±)-(E)-2-Cyclopentyl-1-[4-(pyridin-3-ylmethane-sulfonyl)-phenyl]-cyclopropanecarboxylic acid (5-chloro-thiazol-2-yl)-amide Dissolve (±)-(E)-2-cyclopentyl-1-[4-(pyridin-3-yl-methanesulfonyl)-phenyl]-cyclopropanecarboxylic acid (0.43 g, 1.1 mmol) in 9.5 mL THF, add TBTU (0.39 g, 1.23 mmol) and triethylamine (0.42 mL, 3.5 mmol) and stir for 10 minutes at r.t. Add hydrochloric acid salt of 5-chloro-thiazol-2-ylamine (0.22 g, 1.23 mmol) and stir over night at r.t. Dilute the mixture with ethyl acetate and wash it with 1 N hydrochloric acid. Separate the organic layer and wash it with saturated aqueous sodium bicarbonate solution, followed by saturated sodium chloride solution. Filter through a hydrophobic filter paper and remove the solvent under vacuum. Then purify this material further via column chromatography on silica gel, eluting with a gradient of 0-10% ethanol in dichloromethane, crystallize the material with acetone and TBME to afford the title compound as white crystals (0.11 g). $^1$H-NMR (CDCl$_3$) δ=0.70-0.88 (m, 1H), 1.25-1.32 (m, 1H), 1.33-1.51 (m, 4H), 1.62-1.72 (m, 4H), 1.75-1.86 (m, 1H), 2.07-2.20 (m, 1H), 4.37 (s, 2H), 7.18 (s, 1H), 7.28-7.35 (m, 1H), 7.52-7.64 (m, 3H), 7.72-7.80 (m, 2H), 8.16-8.30 (bs, 1H), 8.31-8.37 (bs, 1H), 8.57-8.63 (m, 1H). MS (m/e): 502 (M+H).

EXAMPLE 40

Separation of (±)-(E)-2-Cyclopentyl-1-[4-(pyridin-3-ylmethanesulfonyl)-phenyl]-cyclopropanecarboxylic acid (5-chloro-thiazol-2-yl)-amide into its enantiomers Add hydrochloric acid (5-6 M in isopropanol) (0.066 ml) to a suspension of (±)-(E)-2-cyclopentyl-1-[4-(pyridin-3-yl-

EXAMPLE 41

(±)-(E)-2-Cyclopentyl-1-[4-(pyridin-3-ylmethane-sulfonyl)-phenyl]-cyclopropanecarboxylic acid thiazol-2-ylamide

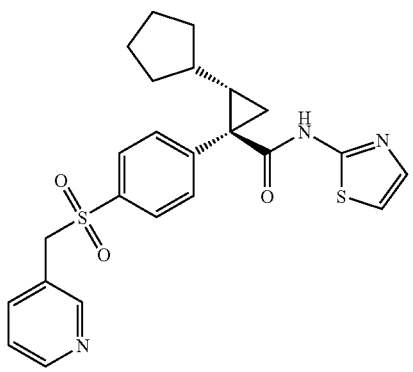

Following the method of example 39 g, reaction of (±)-(E)-2-cyclopentyl-1-[4-(pyridin-3-ylmethanesulfonyl)-phenyl]-cyclopropanecarboxylic acid (0.345 g, 0.89 mmol) in 7.6 mL THF, with TBTU (0.316 g, 0.99 mmol), triethylamine (0.216 mL, 1.79 mmol) and 2-aminothiazole (98.6 mg, 0.99 mmol) and purification by chromatography and crystallization from methanol affords the title compound as white crystals (0.15 g). $^1$H-NMR (CDCl$_3$) δ=0.71-0.88 (m, 1H), 1.24-1.31 (m, 1H), 1.32-1.52 (m, 4H), 1.56-1.73 (m, 4H), 1.78-1.85 (m, 1H), 2.08-2.21 (m, 1H), 4.37 (s, 2H), 6.91-6.97 (m, 1H), 7.28-7.39 (m, 2H), 7.53-7.65 (m, 3H), 7.73-7.82 (m, 2H), 8.25-8.34 (bs, 1H), 8.35-8.42 (bs, 1H), 8.57-8.63 (m, 1H). MS (m/e): 468 (M+H).

EXAMPLE 42

Separation of (±)-(E)-2-Cyclopentyl-1-[4-(pyridin-3-ylmethanesulfonyl)-phenyl]-cyclopropanecarboxylic acid thiazol-2-ylamide into-its enantiomers Following the method of example 55, (±)-(E)-2-cyclopentyl-1-[4(pyridin-3-ylmethanesulfonyl)-phenyl]-cyclopropanecarboxylic acid thiazol-2-ylamide can be separated into its enantiomers. Under the conditions given, the first enantiomer to elute is enantiomer 1. $^1$H-NMR and mass spectral data for the enantiomers are identical to those of the racemate described in example 41.

methanesulfonyl)-phenyl]-cyclopropanecarboxylic acid (5-chloro-thiazol-2-yl)-amide (0.11 g, 0.22 mmol) in methanol (3.1 ml). Concentrate the solution under vacuum. The hydrochloride salt of (±)-(E)-2-cyclopentyl-1-[4-(pyridin-3-ylmethanesulfonyl)-phenyl]-cyclopropanecarboxylic acid (5-chloro-thiazol-2-yl)-amide can be separated into its enantiomers via chromatography on a chiralpak AD_column, eluting with 30% isopropanol in hexane. Under the conditions given, the first enantiomer to elute is enantiomer 1. Dissolve each enantiomer in dichloromethane, wash with saturated aqueous sodium bicarbonate solution, followed by saturated sodium chloride solution. Filter through a hydrophobic filter paper, remove the solvent under vacuum and crystallize with diethyl ether and ethanol to afford the pure enantiomers. $^1$H-NMR and mass spectral data for the enantiomers are identical to those of the racemate described in example 39 g.

EXAMPLE 43

(±)-(E)-2-Cyclohexyl-1-(4-methylsulfamoyl-phenyl)-cyclopropanecarboxylic acid thiazol-2-ylamide

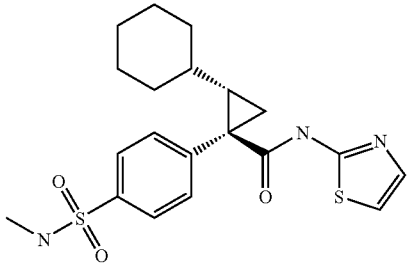

a: 4-Bromo-N-methyl-benzenesulfonamide

Add a solution of 4-bromo-benzenesulfonyl chloride (5.0 g, 19.2 mmol) in 10 mL THF at r.t. to a solution of methylamine (9.6 ml, 2 M in THF, 19.2 mmol) and triethylamine (2.72 mL, 19.2 mmol) over a period of 60 min and stir for 18 h. Add further methylamine (9.6 ml, 2 M in THF, 19.2 mmol) and triethylamine (2.72 mL, 19.2 mmol) and stir for 18 h. Evaporate the solvent under vacuum and add dichloromethane. Wash the organic layer with saturated aqueous sodium bicarbonate solution, followed by saturated sodium chloride solution. Filter through a hydrophobic filter paper and remove the solvent under vacuum. Further purify this material via column chromatography on silica gel, eluting with a gradient of 0-50% ethyl acetate in hexane to afford the title compound (3.75 g) as a white solid. MS (m/e): 251 (M+H).

b: (E)4-(2-Cyclohexyl-1-hydroxymethyl-vinyl)-N-methyl-benzenesulfonamide

Heat a suspension of 4-bromo-N-methyl-benzenesulfonamide (0.51 g, 2.0 mmol), (E)-3-cyclohexyl-2-(4,4,5,5-tetramethyl-[1,3,2]dioxaborolan-2-yl)-prop-2-en-1-ol (0.81 g, 3.06 mmol), caesiumfluoride (0.93 g, 6.12 mmol) and tetrakis(triphenylphosphino)palladium(0) (230 mg, 0.2 mmol) in 12 mL THF to 60° C. for 4 h. Remove the solvent under vacuum and add ethyl acetate, wash the organic layer with water followed by saturated sodium chloride solution. Filter through a hydrophobic filter paper and remove the solvent under vacuum. Further purify the resulting residue by column chromatography, eluting with a gradient from 100:0 to 35:65 hexanes:ethyl acetate to afford the title compound (0.51 g) as a gray solid. MS (m/e): 310 (M+H).

c: (±)-(E)-4-(2-Cyclohexyl-1-hydroxymethyl-cyclopropyl)-N-methyl-benzenesulfonamide Add a 1.1 M solution of diethylzinc in toluene (3.5 mL, 3.89 mmol) at r.t. to a solution of (E)-4-(2-cyclohexyl-1-hydroxymethyl-vinyl)-N-methyl-benzenesulfonamide (300 mg, 0.97 mmol) in 13 mL toluene. After complete addition heat to 60° C., add diiodomethane (0.31 mL, 3.89 mmol) over a period of 1 h and stir for 72 h at that temperature. Cool back to r.t., add another portion diethylzinc (3.5 mL, 3.89 mmol), heat to 60° C., add diiodomethane (0.31 g, 3.89mmol) and stir for 6 h. After cooling to r.t. dilute the mixture with ethyl acetate, cool it to 0° C., and carefully add 1 N hydrochloric acid. Separate, the two phases, and wash the organic layer with saturated aqueous sodium bicarbonate solution, followed by saturated sodium chloride solution. Filter through a hydrophobic filter paper and remove the solvent under vacuum. Purify the resulting residue by column chromatography, eluting with a gradient from 100:0 to 30:70 hexanes: ethyl acetate to obtain (±)-(E)-4-(2-cyclohexyl-1-hydroxymethyl-cyclopropyl)-N-methyl-benzenesulfonamide (53 mg) as crude product. (The crude product obtains (4)-(E)- [2-cyclohexyl-1-(4-methanesulfonyl-phenyl)-cyclopropyl]-methanol). MS (m/e): 324 (M+H).

d: (±)-(E)-2-Cyclohexyl-1-(4-methylsulfamoyl-phenyl)-cyclopropanecarboxylic acid Following the method of example 54 g, using (±)-(E)-4-(2-cyclohexyl-1-hydroxymethyl-cyclopropyl)-N-methyl-benzenesulfonamide (0.34 g, 1.05 mmol) and 45 min at 0° C. after the addition of the chromium oxide the reaction is stopped by addition of saturated sodium bicarbonate solution, extracted at pH 4 with ethyl acetate. The organic layer is washed with 5% aqueous solution of citric acid and saturated aqueous sodium chloride solution, filtered through a hydrophobic filter paper and concentrated under vacuum. Crystallization by addition of dichloromethane and hexane gives the crude title compound as a white solid (318 mg). (The crude product obtains (±)-(E)-2-cyclohexyl-1-(4-methylsulfamoyl-phenyl)-cyclopropanecarboxylic acid). MS (m/e): 355 (M+H$_2$O).

e: (±)-(E)-2-Cyclohexyl-1-(4-methylsulfamoyl-phenyl)-cyclopropanecarboxylic acid thiazol-2-ylamide Following the method of example 39 g, reaction of (±)-(E)-2-cyclohexyl-1-(4-methylsulfamoyl-phenyl)-cyclopropanecarboxylic acid (0.226 g, 0.65 mmol) in 5.7 mL THF, with TBTU (0.236 g, 0.74 mmol), triethylamine (0.162 mL, 1.34 mmol) and 2-aminothiazole (74.2 mg, 0.74 mmol) and purification by column chromatography, eluting with a gradient from 100:0 to 0: 100 hexanes:TBME and then via preparative HPLC (Microsorb™ 60 C18, eluting with a gradient from 100:0 to 0:100 water(+0.1% TFA):acetonitrile) affords the title compound as a white solid (4.0 mg) as TFA salt. $^1$H-NMR (CDCl$_3$) δ=0.17-0.35 (m, 1H), 0.79-0.97 (m, 2H), 0.98-1.79 (m, 10H), 2.00-2.14 (m, 1H), 2.73 (s, 3H), 4.18-4.93 (bs, 4H), 6.98-7.08 (m, 1H), 7.35-7.45 (m, 1H), 7.49-7.61 (m, 2H), 7.84-7.94 (m, 2H). MS (m/e): 420 (M+H).

EXAMPLE 44

(±)-(E)-2-Cyclohexyl-1-(4-methanesulfonyl-3-trifluoromethoxy-phenyl)-cyclopropanecarboxylic acid thiazol-2-ylamide

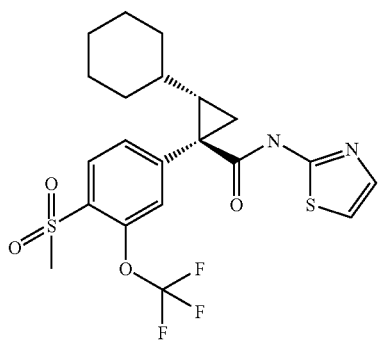

a: 4-Bromo-1-methanesulfonyl-2-trifluoromethoxy-benzene

Following the method of example 9a, reaction of 4-bromo-2-trifluoromethoxy-benzenethiol (1.0 g, 3.48 mmol) with iodomethane (0.238 mL, 3.82 mmol) and potassium carbonate (0.528 g, 3.82 mmol) in 13 mL acetone, followed by oxidation as described in example 39c, using 4-bromo-1-methylsulfanyl-2-trifluoromethoxy-benzene (0.78 g, 2.72 mmol) and oxone® (2.17 g, 3.54 mmol), stirring over night at r.t., addition of oxone® (0.84 g, 1.37 mmol), stirring over night at r.t., addition of oxone® (0.84 g, 1.37 mmol) and stirring over three days at r.t. affords the title compound without further chromatography as a white solid (0.81 g). MS (m/e): 320 (M+H).

b: (E)-3-Cyclohexyl-2-(4-methanesulfonyl-3-trifluoromethoxy-phenyl)-prop-2-en-1-ol Heat a suspension of 4-bromo-1-methanesulfonyl-2-trifluoromethoxy-benzene (0.71 g, 2.23 mmol), (E)-3-cyclohexyl-2-(4,4,5,5-tetramethyl-[1,3,2]dioxaborolan-2-yl)-prop-2-en-1-ol (0.77 g, 2.91 mmol), 2 M aqueous sodium carbonate solution (2.2 mL, 4.4 mmol) and dichloro[1,1'-bis (diphenylphosphino)ferrocene]palladium (II) dichloromethane adduct (164 mg, 2.13 mmol) in 5.7 mL DMF to 80° C. for 2 h. Dilute the mixture with ethyl acetate, separate the organic layer, wash it with water followed by saturated sodium chloride solution. Filter through a hydrophobic filter paper and remove the solvent under vacuum. Further purify the resulting residue by column chromatography, eluting with a gradient from 100:0 to 30:70 hexanes:ethyl acetate to afford the title compound (0.75 g) as a yellow oil. MS (m/e): 396 (M+4H$_2$O).

c: (±)-(E)-[2-Cyclohexyl-1-(4-methanesulfonyl-3-trifluoromethoxy-phenyl)-cyclopropyl]-methanol Following the method of example 43c, reaction of (E)-3-cyclohexyl-2-(4-methanesulfonyl-3-trifluoromethoxy-phenyl)-prop-2-en-1-ol ( 0.7 g, 1.85 mmol) in toluene (24.5 mL), with 1.1 M solution of diethylzinc in toluene (6.73 mL, 7.4 mmol) and diiodomethane (0.59 mL, 7.4 mmol) and four times addition of diethylzinc in toluene (6.73 mL, 7.4 mmol) and diiodomethane (0.59 mL, 7.4 mmol) over a period of six days and purification by column chromatography, eluting with a gradient from 100:0 to 20:80 hexanes:TBME, affords the title compound as colorless oil (0.2 g). MS (m/e): 393 (M+H).

d: (±)-(E)-2-Cyclohexyl-1-(4-methanesulfonyl-3-trifluoromethoxy-phenyl)-cyclopropanecarboxylic acid Following the method of example 54g, using (±)-(E)-[2-cyclohexyl-1-(4-methanesulfonyl-3-trifluoromethoxy-phenyl)-cyclopropyl]-methanol (0.187 g, 0.48 mmol) and 70 min at 0° C. after the addition of the chromium oxide the reaction is stopped by addition of saturated sodium bicarbonate solution, extracted with ethyl acetate. The organic layer is washed with a 5% aqueous solution of citric acid and saturated aqueous sodium chloride solution, filtered through a hydrophobic filter paper and concentrated under vacuum, to afford the title compound as a white solid (180 mg). MS (m/e): 424 (M+H$_2$O).

e: (±)-(E)-2-Cyclohexyl-1-(4-methanesulfonyl-3-trifluoromethoxy-phenyl)-cyclopropanecarboxylic acid thiazol-2-ylamide Following the method of example 39g, reaction of (±)-(E)-2-cyclohexyl-1-(4-methanesulfonyl-3-trifluoromethoxyphenyl)-cyclopropanecarboxylic acid (90 mg, 0.22 mmol) in 1.89 mL THF, with TBTU (78 mg, 0.24 mmol), triethylamine (53.5 µL, 0.44 mmol) and 2-aminothiazole (24.4 mg, 0.24 mmol) and purification by column chromatography, eluting with a gradient from 100:0 to 50:50 hexanes:ethyl acetate affords the title compound as a white solid (50 mg). $^1$H-NMR (CDCl$_3$) δ=0.17-0.33 (m, 1H), 0.81-1.28 (m, 7H), 1.49-1.82 (m, 5H), 2.02-2.14 (m, 1H), 3.30 (s, 3H), 6.94-6.98 (m, 1H), 7.34-7.38 (m, 1H), 7.48-7.56 (m, 2H), 8.14-8.20 (m, 1H). MS (m/e): 489 (M+H).

EXAMPLE 45

(±)-(E)-2-Cyclohexyl-1-(4-methanesulfonyl-3-trifluoromethyl-phenyl)-cyclopropanecarboxylic acid thiazol-2-ylamide

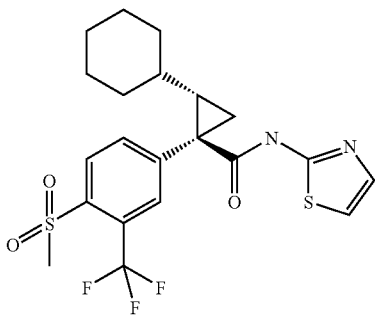

Following the method of example 39g, reaction of (±)-(E)-2-cyclohexyl-1-(4-methanesulfonyl-3-trifluoromethyl-phenyl)-cyclopropanecarboxylic acid (100 mg, 0.25 mmol) in 2.1 mL THF, with TBTU (87 mg, 0.27 mmol), triethylamine (59.7 µL, 0.49 mmol) and 2-aminothiazole (27.2 mg, 0.27 mmol) and purification by column chromatography, eluting with a gradient from 100:0 to 50:50 hexanes:ethyl acetate followed by radial chromatography with dichloromethane saturated with ammonia as eluent affords the title compound as white crystals (8.2 mg). $^1$H-NMR (CDCl$_3$) δ=0.11-0.28 (m, 1H), 0.82-1.32 (m, 7H), 1.58-1.85 (m, 5H), 2.05-2.19 (m, 1H), 3.30 (s, 3h), 6.93-6.99 (m, 1H), 7.32-7.39 (m, 1H), 7.82-7.88 (m, 1H), 7.91-7.96 (m, 1H), 8.26-8.36 (bs, 1H), 8.37-8.44 (m, 1H). MS (m/e): 473 (M+H).

EXAMPLE 46

(±)-(E)-2-Cyclohexyl-1-(4-nitro-phenyl)-cyclopropanecarboxylic acid thiazol-2-ylamide

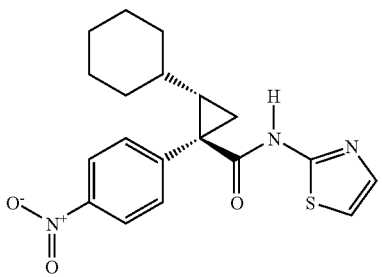

(E)-3-Cyclohexyl-2-(4-nitro-phenyl)-prop-2-en-1-ol

Add tetrakis(triphenylphosphino)palladium(0) (0.60 g, 0.52 mmol) to a solution of 1-bromo-4-nitro-benzene (0.76 g, 3.76 mmol) and (E)-3-cyclohexyl-2-(4,4,5,5-tetramethyl-[1,3,2]dioxaborolan-2-yl)-prop-2-en-1-ol (1.13 g, 4.24 mmol) in dioxane (20 mL). Add cesium fluoride (1.75 g, 12 mmol) and stir the reaction mixture for 12 h at 80° C. Allow the reaction mixture to cool to r.t. Dilute the reaction mixture with ethyl acetate and wash with water. Separate the layers. Dry the organic phase over sodium sulfate, filter and concentrate. Purify the residue via silica gel chromatography, eluting with a gradient from 95:5 to 7:3 hexanes:ethyl acetate to obtain the title compound (0.67 g). $^1$H-NMR (CDCl$_3$) δ=1.05-1.72 (m, 10 H), 1.89-2.04 (m, 1H), 4.28-4.36 (m, 2H), 5.61-5.69 (m, 1H), 7.34-7.43 (m, 2H), 8.18-8.26 (m, 2H).

b: (±)-(E)-[2-Cyclohexyl-1-(4-nitro-phenyl)-cyclopropyl]-methanol

Add a solution of diethylzinc in toluene (0.76 mL, 1.1 M, 0.84 mmol) and diiodomethane (0.14 mL, 1.74 mmol) to a solution of (E)-3-cyclohexyl-2-(4-nitro-phenyl)-prop-2-en-1-ol (55 mg, 0.21 mmol) in toluene (2 mL). Stir the reaction mixture at r.t. for 12 h. Dilute the mixture with ethyl acetate. Wash the mixture first with 1 N HCl and then with saturated aqueous sodium bicarbonate. Separate the layers and dry the organic phase over magnesium sulfate. Filter and concentrate. Purify the crude product via column chromatography on silica gel, eluting with a gradient from 95:5 to 7:3 hexanes:ethyl acetate to obtain the title compound (24 mg). $^1$H-NMR (CDCl$_3$) δ=0.15-0.34 (m, 1H), 0.78-1.77 (m, 13H), 3.40-3.49 (m, 1H), 3.89-4.01 (m, 1H), 7.50-7.61 (m, 2H), 8.09-8.25 (m, 2H).

c: (±)-(E)-2-Cyclohexyl-1-(4-nitro-phenyl)-cyclopropanecarboxylic acid thiazol-2-ylamide Add concentrated sulfuric acid (4.8 mL) to a solution of chromium oxide (5.32 g) in water (5 mL), and then dilute the resulting solution with water to a total volume of 20 mL. Add 1.3 mL of this solution dropwise to a solution of (±)-(E)-[2-cyclohexyl-1-(4-nitro-phenyl)-cyclopropyl]-methanol (240 mg, 0.87 mmol) in acetone (26 mL). Stir the reaction mixture for 2 h at r.t. Dilute with water to dissolve all the chromium (III) salts, and neutralize the solution with saturated aqueous sodium bicarbonate. Extract the solution with ethyl acetate (3×100 mL). Dry the combined organic extracts with sodium sulfate, filter and concentrate to obtain the acid [MS (m/e): 244 (M−H-44)] as a white solid. To the acid add 2-aminothiazole (101 mg, 1.01 mmol), TBTU (320 mg, 1.00 mmol), and THF (10 mL). Cool the solution to 0° C. and add triethylamine (0.25 mL, 1.78 mmol). Stir the solution for 12 h, and then concentrate it under vacuum. Purify the residue via silica gel column chromatography, eluting with a gradient from 95:5 to 7:3 hexanes:ethyl acetate to obtain the title compound as a white solid (252 mg). $^1$H-NMR (CDCl$_3$) δ=0.17-0.36 (m, 1H), 0.81-1.32 (m, 7H), 1.50-1.71 (m, 3H), 1.72-1.84 (m, 2H), 2.03-2.17 (m, 1H), 6.91-6.97 (m, 1H), 7.32-7.38 (m, 1H), 7.57-7.65 (m, 2H), 8.27-8.34 (m, 2H), 8.34-8.45 (m, 1H). MS (m/e): 372 (M+H).

EXAMPLE 47

(±)-(E)-3-12-Cyclohexyl-1-(thiazol-2-ylcarbamoyl)-cyclopropyl]-benzoic acid

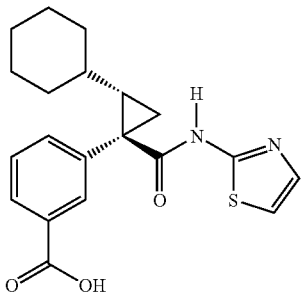

a: (E)-3-(2-Cyclohexyl-1-hydroxymethyl-vinyl)-benzoic acid methyl ester

Following the method of example 46a, Suzuki coupling of 3-bromo-benzoic acid methyl ester (1.05 g, 4.88 mmol) with (E)-3-cyclohexyl-2-(4,4,5,5-tetramethyl-[1,3,2]dioxaborolan-2-yl)-prop-2-en-1-ol (1.48 g, 5.56 mmol) in the presence of tetrakis(triphenylphosphino)palladium(0) (0.32 g, 0.28 mmol) and cesium fluoride (2.2 g, 14 mmol) in dioxane (15 mL) gives the title compound (1.0 g). MS (m/e): 257 (M+H–H$_2$O).

b: (±)-(E)-3-(2-Cyclohexyl-1-hydroxymethyl-cyclopropyl)-benzoic acid methyl ester Following the method of example 46b, cyclopropanation of (E)-3-(2-cyclohexyl-1-hydroxymethyl-vinyl)-benzoic acid methyl ester (160 mg, 0.58 mmol) with diethylzinc in toluene (2.0 mL, 1.1 M, 2.20 mmol) and diiodomethane (0.36 mL, 4.47 mmol) in toluene (3 mL) at r.t. gives the title compound (102 mg) as a white solid. MS (m/e): 271 (M+H–H$_2$O).

c: (±)-(E)-3-[2-Cyclohexyl-1-(thiazol-2-yloxycarbonyl)-cyclopropyl]-benzoic acid methyl ester Following the method of example 46c, oxidation of (±)-(E)-3-(2-Cyclohexyl-1-hydroxymethyl-cyclopropyl)-benzoic acid methyl ester (102 mg, 0.35 mmol) with Jones reagent (0.49 mL) in acetone (8 mL) and subsequent coupling of the acid with 2-aminothiazole (41 mg, 0.41 mmol) in the presence of TBTU (131 mg, 0.41 mmol) and triethylamine (0.1 mL, 0.71 mmol) in THF (4 mL) gives the title compound (123 mg). MS (m/e): 385 (M+H).

d: (±)-(E)-3-[2-Cyclohexyl-1-(thiazol-2-ylcarbamoyl)-cyclopropyl]-benzoic acid Dissolve (±)-(E)-3-[2-cyclohexyl-1-(thiazol-2-yloxycarbonyl)-cyclopropyl]-benzoic acid methyl ester (21 mg, 0.06 mmol) in THF (1 mL), add aqueous sodium hydroxide (0.1 mL, 1.0 M, 0.1 mmol), and stir the reaction mixture at r.t. for 1-2 days. Remove the THF, adjust pH of aqueous slurry to pH 1 with 1 N HCl, and extract with ether. Dry the combined organic extracts over sodium sulfate, filter and concentrate to obtain the title compound (13 mg). $^1$H-NMR (CDCl$_3$) δ=0.21-0.42 (m, 1H), 0.79-2.07 (m, 13H), 6.87-6.99 (m, 1H), 7.32-7.41 (m, 1H), 7.46-7.55 (m, 1H), 7.62-7.71 (m, 1H), 7.76-7.87 (m, 1H), 8.21-8.31 (m, 1H), 10.86-11.23 (bs, 1H). MS (m/e): 371 (M+H).

EXAMPLE 48

(±)-(E)-[2-Cyclohexyl-1-(4-methoxy-phenyl)-cyclopropanecarboxylic acid thiazol-2-ylamide]

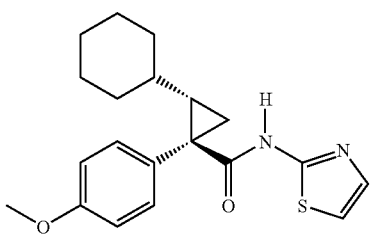

a: (E)-3-Cyclohexyl-2-(4-methoxy-phenyl)-prop-2-en-1-ol

Following the method of example 46a, Suzuki coupling of 1-bromo-4-methoxy-benzene (0.65 g, 3.48 mmol) with (E)-3-cyclohexyl-2-(4,4,5,5-tetramethyl-[1,3,2]dioxaborolan-2-yl) -prop-2-en-1-ol (1.05 g, 3.94 mmol) in the presence of tetrakis(triphenylphosphino)palladium(0) (0.25 g, 0.22 mmol) and cesium fluoride (1.69 g, 11 mmol) in dioxane (20 mL) gives the title compound (0.5 g). $^1$H-NMR (CDCl$_3$) δ=0.92-2.15 (m, 10H), 2.62-2.77 (m, 1H), 3.82 (s, 3H), 4.23-4.29 (m, 2H), 6.02-6.11 (m, 1H), 6.86-6.94 (m, 2H), 7.11-7.17 (m, 2H).

b: (±)-(E)-[2-Cyclohexyl-1-(4-methoxy-phenyl)-cyclopropyl]-methanol

Following the method of example 46b, cyclopropanation of (E)-3-cyclohexyl-2-(4-methoxy-phenyl)-prop-2-en-1-ol (108 mg, 0.44 mmol) with diethylzinc in toluene (1.5 mL, 1.1 M, 1.65 mmol) and diiodomethane (0.27 mL, 3.35 mmol) in toluene (2 mL) at r.t. gives the title compound (45 mg). MS (m/e): 243 (M+H–H$_2$O).

c: (±)-(E)-[2-Cyclohexyl-1-(4-methoxy-phenyl)-cyclopropanecarboxylic acid thiazol-2-ylamide]

Following the method of example 46c, oxidation of (±)-(E)-[2-cyclohexyl-1-(4-methoxy-phenyl)-cyclopropyl]-methanol (45 mg, 0.17 mmol) with Jones reagent (0.24 mL) in acetone (5 mL) and subsequent coupling of the acid with 2-aminothiazole (18 mg, 0.18 mmol) in the presence of TBTU (62 mg, 0.19 mmol) and triethylamine (50 μL, 0.36 mmol) in THF (2 mL) gives the title compound (11 mg). $^1$H-NMR (CDCl$_3$) δ=0.31-0.48 (m, 1H), 0.77-1.70 (m, 11H), 1.80-2.05 (m, 2H), 3.86 (s, 3H), 6.86-7.01 (m, 3H), 7.29-7.37 (m, 3H), 8.49-8.61 (bs, 1H). MS (m/e): 357 (M+H).

EXAMPLE 49

(±)-(E)-4-[2-Cyclohexyl-1-(thiazol-2-ylcarbamoyl)-cyclopropyl]-N-pyridin-3-ylmethyl-benzamide

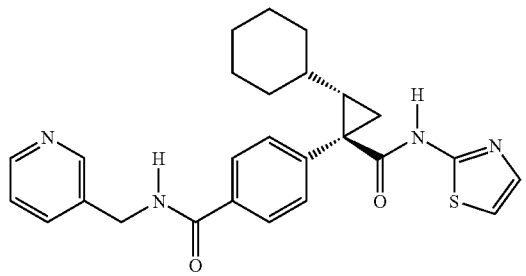

a: (E)-4-(2-Cyclohexyl-1-hydroxymethyl-vinyl)-benzoic acid methyl ester

Following the method of example 46a, Suzuki coupling of 4-bromo-benzoic acid methyl ester (1.05 g, 4.88 mmol) with (E)-3-cyclohexyl-2-(4,4,5,5-tetramethyl-[1,3,2]dioxaborolan-2-yl)-prop-2-en-1-ol (1.48 g, 5.56 mmol) in the presence of tetrakis(triphenylphosphino)palladium(0) (0.35 g, 0.30 mmol) and cesium fluoride (2.1 g, 14 mmol) in dioxane (15 mL) gives the title compound (1.0 g). MS (m/e): 275 (M+H).

b: (±)-(E)4-(2-cyclohexylyl-1-hydroxymethyl-cyclopropyl)-benzoic acid methyl ester, Following the method of example 46b, cyclopropanation of (E)-4-(2-cyclohexyl-1-hydroxymethyl-vinyl)-benzoic acid methyl ester (207 mg, 0.72 mmol) with diethylzinc in toluene (2.6 mL, 1.1 M, 2.86 mmol) and diiodomethane (0.46 mL, 5.71 mmol) in toluene (3 mL) at r.t. gives the title compound (142 mg) as a white solid. MS (m/e): 289 (M+H).

c: (±)-(E)-4-[2-Cyclohexyl-1-(thiazol-2-ylcarbamoyl)-cyclopropyl]-benzoic acid methyl ester Following the method of example 46c, oxidation of (±)-(E)-4-(2-cyclohexyl-1-hydroxymethyl-cyclopropyl)-benzoic acid methyl ester (142 mg, 0.49 mmol) with Jones reagent (0.68 mL) in acetone (11 mL) and subsequent coupling of the acid with 2-aminothiazole (56 mg, 0.56 mmol) in the presence of TBTU (186 mg, 0.58 mmol) and triethylamine (0.14 mL, 1.00 mmol) in THF (4 mL) gives the title compound (153 mg).
MS (m/e): 385 (M+H).

d: (±)-(E)-4-[2-Cyclohexyl-1-(thiazol-2-ylcarbamoyl)-cyclopropyl]-benzoic acid

Following the method of example 47d, hydrolysis of (±)-(E)-4-[2-cyclohexyl-1-(thiazol-2-ylcarbamoyl)-cyclopropyl]-benzoic acid methyl ester (14 mg, 0.04 mmol) in THF (1 mL) with aqueous sodium hydroxide (0.1 mL, 1.0 M, 0.1 mmol) gives the title compound (10 mg). MS (m/e): 371 (M+H).

e: (±)-(E)4-[2-Cyclohexyl-1-(thiazol-2-ylcarbamoyl)-cyclopropyl]-N-pyridin-3-ylmethyl-benzamide Place HOAt (30 mg, 0.22 mmol) in reaction vessel. Add (±)-(E)-4-[2-cyclohexyl-1-(thiazol-2-ylcarbamoyl)-cyclopropyl]-benzoic acid (12 mg, 0.03 mmol), P1-EDC-resin (100 mg), and methylene chloride (1.5 mL). Agitate for 30 min then add 3-(aminomethyl)pyridine (11 µL, 0.11 mmol). Agitate the reaction mixture for 2 days. Add P1-EDA-resin, and agitate the mixture overnight. Filter, rinse the resin with methylene chloride and concentrate the filtrate. Purify the residue via silica gel column chromatography, eluting with a gradient from 1:1 to 0:1 hexanes:ethyl acetate to afford the title compound as a white solid (13 mg). $^1$H-NMR (CDCl$_3$) δ=0.23-0.41 (m, 1H), 0.79-1.86 (m, 12H), 1.97-2.13 (m, 1H), 4.66-4.77 (m, 2H), 6.57-6.70 (m, 1H), 6.89-6.97 (m, 1H), 7.28-7.38 (m, 2H), 7.45-7.56 (m, 2H), 7.70-7.79 (m, 1H), 7.81-7.92 (m, 2H), 8.36-8.73 (m, 3H). MS (m/e): 461 (M+H).

EXAMPLE 50

(±)-(E)4-[2-Cyclohexyl-1-(thiazol-2-ylcarbamoyl)-cyclopropyl]-N-methyl-benzamide

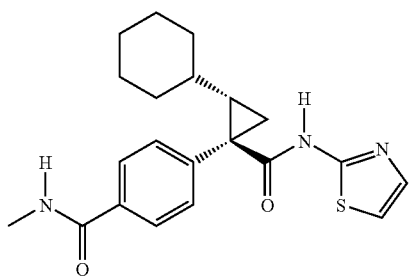

Following the method of example 49e, peptide coupling of (±)-(E)-4-[2-cyclohexyl-1-(thiazol-2-ylcarbamoyl)-cyclopropyl]-benzoic acid (14 mg, 0.04 mmol) with methylamine in THF (42 µL, 2.0 M, 0.08 mmol) in the presence of HOAt (20 mg, 0.15 mmol) and P1-EDC-resin (110 mg) gives the title compound (12 mg). $^1$H-NMR (CDCl$_3$) δ=0.23-0.39 (m, 1H), 0.75-1.88 (m, 12H), 1.95-2.13 (m, 1H), 3.01-3.09 (m, 3H), 6.14-6.30 (bs, 1H), 6.86-6.95 (m, 1H), 7.30-7.36 (m, 1H), 7.43-7.55 (m, 2H), 7.74-7.88 (m, 2H), 8.36-8.53 (bs, 1H). MS (m/e): 384 (M+H).

EXAMPLE 51

(±)-(E)-1-(4-Acetylamino-phenyl)-2-cyclohexyl-cyclopropanecarboxylic acid thiazol-2-ylamide

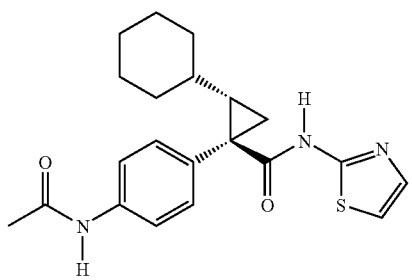

a: (±)-(E)-1-(4-Amino-phenyl)-2-cyclohexyl-cyclopropanecarboxylic acid thiazol-2-ylamide Dissolve (±)-(E)-2-cyclohexyl-1-(4-nitro-phenyl)-cyclopropanecarboxylic acid thiazol-2-ylamide (250 mg, 0.67 mmol) in MeOH (50 mL). Add Pd (10% on carbon, 70 mg) and stir the reaction mixture under hydrogen atmosphere at r.t. for 2-3 days. Filter through celite®, and concentrate the filtrate to obtain the title compound as an off-white solid (217 mg). MS (m/e): 342 (M+H).

b: (±)-(E)-1-(4-Acetylamino-phenyl)-2-cyclohexyl-cyclopropanecarboxylic acid thiazol-2-ylamide Following the method of example 49e, peptide coupling of (±)-(E)-1-(4-amino-phenyl)-2-cyclohexyl-cyclopropanecarboxylic acid thiazol-2-ylamide (15 mg, 0.04 mmol) with acetic acid (5 μL, 0.09 mmol) in the presence of HOAt (21 mg, 0.15 mmol) and P1-EDC-resin (110 mg) gives the title compound (14 mg). $^1$H-NMR (CDCl$_3$) δ=0.29-0.46 (m, 1H), 0.76-1.71 (m, 11H), 1.77-1.88 (m, 1H), 1.91-2.06 (m, 1H), 2.22 (s, 3H), 6.87-6.96 (m, 1H), 7.29-7.44 (m, 4H), 7.54-7.67 (m, 2H), 8.54 (bs, 1H). MS (m/e): 384 (M+H).

EXAMPLE 52

(±)-(E)-2-Cyclohexyl-1-(4-methanesulfonylamino-phenyl)-cyclopropanecarboxylic acid thiazol-2-ylamide

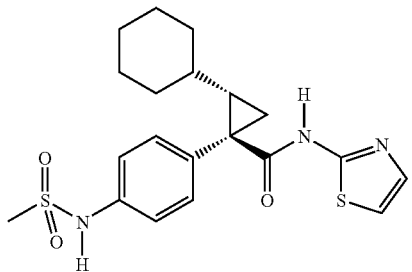

Dissolve (±)-(E)-1-(4-amino-phenyl)-2-cyclohexyl-cyclopropanecarboxylic acid thiazol-2-ylamide (28 mg, 0.08 mmol) in methylene chloride (1.5 mL). Cool the solution to 0° C. and add triethylamine (34 μL, 0.24 mmol) and methanesulfonyl chloride (16 μL, 0.21 mmol). Stir the reaction mixture at r.t. for 3-4 days. Dilute the reaction mixture with methylene chloride, wash the solution with 1 N HCl and saturated aqueous sodium bicarbonate. Dry the organic phase over sodium sulfate, filter and concentrate. Purify the residue by preparative HPLC (XTerra C18, 2:3 to 4:2 acetonitrile:water+0.1% TFA) to obtain the title compound as a white solid (10 mg). $^1$H-NMR (CDCl$_3$) δ=0.23-0.44 (m, 1H), 0.86-1.72 (m, 1H), 1.74-1.85 (m, 1H), 1.93-2.07 (m, 1H), 3.13 (s, 3H), 6.90-6.97 (m, 1H), 7.02 (bs, 1H), 7.23-7.27 (m, 2H), 7.34-7.43 (m, 3H), 8.73 (bs, 1H). MS (m/e): 420 (M+H).

EXAMPLE 53

(±)-(E)-2-Cyclohexyl-1-(6-methanesulfonyl-pyridin-3-yl)-cyclopropanecarboxylic acid thiazol-2-ylamide

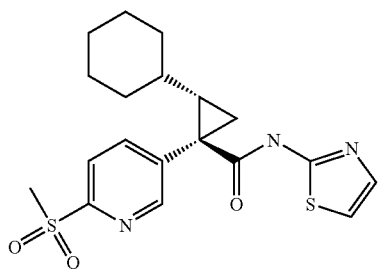

a: 5-Bromo-2-methylsulfanyl-pyridine

Add sodiumthiomethoxide (1.0 g, 14.4 mmol) to a suspension of 2,5-dibromo-pyridine (3.1 g, 13 mmol) in DMF (8 ml) at r.t. Stir for 2 h at r.t., dilute with water (20 ml) and extract 2 times with MTBE. Dry organic layers over sodium sulfate and remove solvents under vacuum to obtain 2.59 g of 5-bromo-2-methylsulfanyl-pyridine. MS (m/e): 205 (M+H).

b: 5-Bromo-2-methanesulfonyl-pyridine

Add a suspension of oxone®(4.97 g, 8.1 mmol) in 10 mL water to a solution of 5-bromo-2-methylsulfanyl-pyridine (1.1 g, 5.4 mmol) in 10 mL methanol, stir at r.t. for 1 h and remove methanol under vacuum. Extract the aqueous residue with dichloromethane, dry the organic extracts over sodium sulfate, filtrate and concentrate under reduced pressure to obtain 1.24 g of 5-bromo-2-methanesulfonyl-pyridine. MS (m/e): 237 (M+H).

c: (E)-3-Cyclohexyl-2-(6-methanesulfonyl-pyridin-3-yl)-prop-2-en-1-ol

Add 5-bromo-2-methanesulfonyl-pyridine (0.47 g, 2.0 mmol), [1,1′-bis(diphenylphosphino)ferrocene]-dichloropalladium(II) (163 mg, 0.2 mmol), and Na$_2$CO$_3$ (2.5 mL, 2.0 M, 5.0 mmol) to a solution of 3-cyclohexyl-2-(4,4,5,5-tetramethyl-[1,3,2]dioxaborolan-2-yl)-prop-2-en-1-ol (0.53 g, 2.2 mmol) in DMF (10 mL). Stir at 80° C. for 18 h, monitor completion of the reaction by LCMS. Treat the reaction mixture with water and extract 3 times with MTBE. Dry organic layers over sodium sulfate and remove solvents under vacuum to obtain 0.72 g crude product. Purification by silica gel chromatography, eluting with gradient from 10:0 to 8:2 dichloromethane:MTBE affords 350 mg (E)-3-cyclohexyl-2-(6-methanesulfonyl-pyridin-3-yl)-prop-2-en-1-ol. MS (m/e): 296 (M+H).

d: (±)-(E)-3-Cyclohexyl-2-(6-methanesulfonyl-pyridin-3-yl)-prop-2-en-1-ol

Add a solution of diethylzinc in toluene (4.55 mL, 1.1 M, 5.0 mmol) to a solution of (E)-3-cyclohexyl-2-(6-methanesulfonyl-pyridin-3-yl)-prop-2-en-1-ol (295 mg, 1.0 mmol), in 1,2-dichloroethane (10 mL). Warm the reaction mixture to 60° C., and add diiodomethane (0.80 mL, 10 mmol) drop wise over 3 h. Then stir the reaction mixture at 60° C. for 16 h. Since LCMS shows incomplete reaction, rerun the addition with the same amount of diethylzinc and diiodomethane. Then stir the reaction mixture at 60° C. for 24 h. Treat the mixture with saturated ammonium chloride. Wash the organic layer with saturated NaHCO$_3$ and saturated Na$_2$SO$_3$, dry over sodium sulfate and remove solvents under vacuum to obtain 180 mg of crude product. MS (m/e): 310 (M+H).

e: (±)-(E)-2-Cyclohexyl-1-(6-methanesulfonyl-pyridin-3-y:)-cyclopropanecarboxylic acid Following method of example 16 g, reaction of (±)-(E)-3-cyclohexyl-2-(6-methanesulfonyl-pyridin-3-yl)-prop-2-en-1-ol (170 mg, 0.55 mmol) and Jones reagent (0.88 mL, 2.2 mmol) gives 42 mg crude product. MS (m/e): 324 (M+H).

f: (±)-(E)-2-Cyclohexyl-1-(6-methanesulfonyl-pyridin-3-yl)-cyclopropanecarboxylic acid thiazol-2-ylamide Add 2-amino-thiazole (18 mg, 0.18 mmol), TBTU (58 mg, 0.18 mmol) and triethylamine (0.086 mL, 0.615 mmol) to a solution of (±)-(E)-2-cyclohexyl-1-(6-methanesulfonyl-pyridin-3-yl)-cyclopropanecarboxylic acid (40 mg, max. 0.123 mmol) in THF (3 ml) at 0° C. Stir the solution for 60 h at r.t., add water (6 ml) and extract with ethyl acetate. Dry the organic layer over sodium sulfate and remove solvent under vacuum. Purify the crude product by silica gel chromatography, eluting with gradient from 99:1 to 97:3 dichloromethane: ethanol to obtain 9 mg of the titled compound. $^1$H-NMR (CDCl$_3$): δ=0.18-0.33 (m, 1H), 0.85-1.36 (m, 6H), 1.52-1.85 (m, 6H), 2.07-2.19 (m, 1H), 3.32 (s, 3H), 6.97 (mc, 1H), 7.35 (mc, 1H), 8.03 (mc, 1H), 8.60 (bs, 1H), 8.79 (s, 1H). MS (m/e): 406 (M+H).

EXAMPLE 54

(±)-(E)-2-Cyclohexyl-1-(4-methanesulfonyl-phenyl)-cyclopropanecarboxylic acid thiazol-2-ylamide

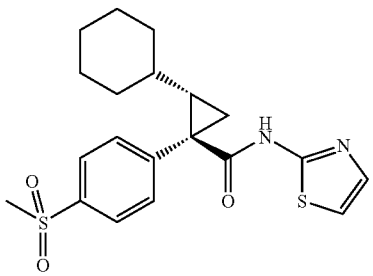

a: (E)-3-Cyclohexyl-acrylic acid ethyl ester

Add triethylphospinoacetate (185 g, 821 mmol) to a suspension of hexane-washed sodium hydride (34.5 g, 60%, 862 mmol) in THF (1 L) at 0° C. Stir the resulting mixture for 1 h, and then cool it to −78° C. Then add a solution of cyclohexylmethanal (92.2 g, 821 mmol) in THF (500 mL) dropwise over 90 min, maintaining an internal temperature of less than −68° C. Allow the reaction mixture to warm to r.t. over 18 h. Then add a solution of saturated aqueous ammonium chloride solution (1 L) to the reaction mixture carefully. Extract the resulting mixture with ether (3×1 L). Combine the extracts and wash them with water (2×1 L), followed by saturated aqueous sodium chloride solution (1 L). Then dry the extracts over magnesium sulfate, and concentrate the solution under vacuum to afford the title compound as a yellow oil (154.8 g). GC-MS (m/e): 182 (M+).

b: (Z)-2-Bromo-3-cyclohexyl-acrylic acid ethyl ester

Add a solution of bromine (43.5 mL, 848 mmol) in carbon tetrachloride (500 mL) to a solution of 3-cyclohexyl-acrylic acid ethyl ester (154.5 g, 848 mmol) in dichloromethane cooled to −10° C. such that the temperature does not exceed 0° C. Stir the reaction mixture for 2 h at −10° C., and then add triethylamine (143 mL, 1.02 mol), again such that the temperature does not exceed 0° C. Allow the stirred reaction mixture to warm to r.t. overnight. Then dilute it with dichloromethane (500 mL), cool the resulting mixture to 0° C., and adjust the pH to a value of less than 2 by the careful addition of 1 N aqueous hydrochloric acid. Separate the resulting two layers, and extract the aqueous phase with dichloromethane (1 L). Combine the extract and the first organic layer, dry them over magnesium sulfate, and concentrate them under vacuum to afford a yellow oil. Apply a solution of this oil in dichloromethane to a silica gel column, and elute with a 1:1 mixture of dichloromethane and cyclohexane to afford the title compound as a yellow oil (103.5 g). MS (m/e): 262 (M+H).

c: (E)-3-Cyclohexyl-2-(4-methylsulfanyl-phenyl)-acrylic acid ethyl ester

Dissolve (Z)-2-bromo-3-cyclohexyl-acrylic acid ethyl ester (76.4 g, 300 mmol) and 4-(methylthio)benzene boronic acid (60.5 g, 360 mmol) in a mixture of 1500 mL toluene, 500 mL ethanol and 2M aqueous sodium carbonate solution (500 mL). Add tetrakis(triphenylphosphino)palladium(0) (10.4 g, 3mol %) and heat the mixture at reflux for 5 h. Cool and remove the ethanol under vacuum. Partition the residue between water (250 mL) and dichloromethane (4×250 mL). Combine the extracts and dry over magnesium sulfate, filter and concentrate. Pass through a silica gel pad with a mix of iso-hexane:dichloromethane:diethyl ether (92:4:4) to give the title compound as a hazy oil (80 g). GC-MS (m/e): 304 (M+).

d: (E)-3-Cyclohexyl-2-(4-methanesulfonyl-phenyl)-acrylic acid ethyl ester

Add a suspension of oxone® (33 g, 53 mmol) in water (300 mL) to a solution of (E)-3-cyclohexyl-2-(4-methylsulfanyl-phenyl)-acrylic acid ethyl ester (7.4 g, 24 mmol) in acetone (300 mL). Stir for three h, and then add water. Extract the resulting mixture with dichloromethane (2×500 mL). Combine the extracts, wash them with saturated aqueous sodium chloride solution, dry them over magnesium sulfate, and remove solvent under vacuum. Apply the residue to silica gel column, and elute this with a 15:15:70 mixture of dichloromethane: ethyl acetate: hexane to afford the title compound as an off-white solid (7.35 g). MS (m/e): 337 (M+H).

e: (E)-3-Cyclohexyl-2-(4-methanesulfonyl-phenyl)-prop-2-en-1-ol

Add a solution of DIBAL in toluene (36.5 mL, 1.5 M, 54.6 mmol) dropwise over one h to a solution of (E)-3-cyclohexyl-2-(4-methanesulfonyl-phenyl)-acrylic acid ethyl ester (7.35 g, 21.8 mmol) in THF (200 mL) cooled to −78° C. Then allow the reaction mixture to slowly warm to r.t., and stir it for 18 h. Add methanol (50 mL), and then remove volatiles under vacuum. Partion the residue between ethly acetate (200 mL) and water (200 mL). Then extract the aqueous layer with ethyl acetate (2×300 mL). Combine the organic layers, wash them with saturated aqueous sodium chloride solution (200 mL), dry them over magnesium sulfate, and then filter them through celite®. Concentrate the filtrate to afford the title compound as an oil (6.0 g). MS (m/e): 295 (M+H).

f: (±)-(E)-[2-Cyclohexyl-1-(4-methanesulfonyl-phenyl)-cyclopropyl]-methanol

Add a solution of diethylzinc in hexanes (93.5 mL, 1.0 M, 93.5 mmol) to a solution of (E)-3-cyclohexyl-2-(4-methanesulfonyl-phenyl)-prop-2-en-1-ol (5.5 g, 19 mmol) in toluene (500 mL). Warm the reaction mixture to 60° C., and then add diiodomethane (15.1 mL, 187 mmol) dropwise over 30 min. Then stir the reaction mixture in the presence of air at 50° C. for 16 h. Dilute the mixture with ether (100 mL), cool it to 0° C., and carefully add 1 N hydrochloric acid. Separate the two phases, and extract the aqueous layer with ether (300 mL). Combine the extract and first organic layer, and wash them with saturated aqueous ammonium bicarbonate solution (500 mL). Dry the organic phase over magnesium sulfate, filter and concentrate to an oil. Redissolve this oil in ether (300 mL), and wash the resulting solution with water (2×300 mL), followed by saturated aqueous sodium chloride solution (200 mL). Dry over magnesium sulfate, and concentrate under vacuum to afford a brown oil, which is a mixture of the title compound and unreacted starting material. Submit this mixture to the reaction conditions again, and isolate the crude product as before. Then purify this material further via column chromatography on silica gel, eluting with a gradient of 1-4% methanol in dichloromethane to afford the title compound (2.5 g).

MS (m/e): 326 (M+H).

g: (±)-(E)-2-Cyclohexyl-1-(4-methanesulfonyl-phenyl)-cyclopropanecarboxylic acid Add concentrated sulfuric acid (3.8 mL) to a solution of chromium oxide (4.46 g, 44.6 mmol) in water (5 mL), and then dilute the resulting solution with water to a total volume of 16.6 mL. Add this solution dropwise to a solution of (±) (E)-[2-Cyclohexyl-1-(4-methanesulfonyl-phenyl)-cyclopropyl]-methanol (2.5 g, 8.1 mmol) in acetone (50 mL) at 0° C. After the reaction mixture has been stirred for two h, carefully add water (100 mL) and ether (100 mL). Separate the resulting two phases, and extract the aqueous layer with ether (2×100 mL). Combine the organic layer and extracts, wash them with saturated aqueous sodium chloride solution (2×100 mL), and then remove volatiles under vacuum to afford impure product. Triturate this material with methanol to afford the title compound as a white solid (1.3 g). MS (m/e): 340 (M+$NH_4$).

h: (±)-(E)-2-Cyclohexyl-1-(4-methanesulfonyl-phenyl)-cyclopropanecarboxylic acid thiazol-2-ylamide Add 2-aminothiazole (430 mg, 4.25 mmol), TBTU (1.24 g, 3.86 mmol), and triethylamine (1.086 mL, 7.73 mmol) to a solution of (±)-(E)-2-cyclohexyl-1-(4-methanesulfonyl-phenyl)-cyclopropanecarboxylic acid (1.25 g, 3.86 mmol) in THF (62 mL). Stir the solution for three h, and then concentrate it under vacuum. Redissolve the residue in ethyl acetate (100 mL), and wash the resulting solution with 1 N hydrochloric acid (100 mL). Extract the aqueous wash with ethyl acetate (50 mL), and combine this extract with the first ethyl acetate solution. Wash the resulting solution with saturated aqueous sodium bicarbonate solution (100 mL), followed by saturated sodium chloride solution (100 mL). Dry the ethyl acetate solution over magnesium sulfate, and concentrate it under vacuum to afford a brown solid. Further purify this material via silica gel column chromatography, eluting with a gradient from 2:1 to 1:1 cyclohexane:ethyl acetate to afford a white solid (1.08 g). $^1$H-NMR ($CDCl_3$) δ=0.89-1.05 (m, 2H), 1.12-1.22 (m, 2H), 1.28 (mc, 1H), 1.51-1.65 (m, 7H), 1.75 (mc, 2H), 2.02-2.15 (m, 1H), 3.17 (s, 3H), 6.95 (mc, 1H), 7.35 (mc, 1H), 7.64 (mc, 2H), 8.03 (mc, 2H), 8.39 (s, 1H). MS (m/e): 405.1 (M+H).

EXAMPLE 55

Separation of (±)-(E)-2-Cyclohexyl-1-(4-methanesulfonyl-phenyl)-cyclopropanecarboxylic acid thiazol-2-ylamide into its enantiomers 2-(S)-Cyclohexyl-1-(R)-(4-methanesulfonyl-phenyl)-cyclopropanecarboxylic acid thiazol-2-ylamide and 2-(R)-Cyclohexyl-1-(S)-(4-methanesulfonyl-phenyl)-cyclopropanecarboxylic acid thiazol-2-ylamide (±)-(E)-2-Cyclohexyl-1-(4-methanesulfonyl-phenyl)-cyclopropanecarboxylic acid thiazol-2-ylamide can be separated into its enantiomers via chromatography on a chiralpak AD column, eluting with ethanol. Under the conditions given, the first enantiomer to elute is 2-(S)-cyclohexyl-1-(R)-(4-methanesulfonyl-phenyl)-cyclopropanecarboxylic acid thiazol-2-ylamide, and the second is 2-(R)-cyclohexyl-1-(S)-(4-methanesulfonyl-phenyl)-cyclopropanecarboxylic acid thiazol-2-ylamide. The absolute stereochemistry of the enantiomers has been confirmed by crystallography. $^1$H-NMR and mass spectral data for the enantiomers are identical to those of the racemate described in example 54.

EXAMPLE 56

(±)-(E)-2-Cyclopentylmethyl-1-(4-methanesulfonyl-phenyl)-cyclopropanecarboxylic acid thiazol-2-ylamide

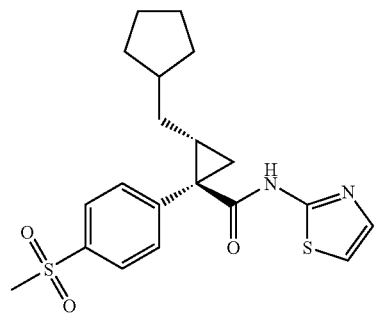

$^1$H-NMR ($d_6$-DMSO) δ=0.27-0.11 (m, 1H), 0.94-1.09 (m, 2H), 1.30-1.37 (m, 1H), 1.38-1.57 (m, 5H), 1.58-1.87 (m, 4H), 1.90-2.02 (m, 1H), 3.21-3.25 (s, 3H), 7.15-7.20 (m, 1H), 7.40-7.45 (m, 1H), 7.60-7.66 (m, 2H), 7.87-7.93 (m, 2H), 11.40-11.49 (s, 1H). MS(m/e): 405 (M+H).

EXAMPLE 57

Separation of (±)-(E)-2-Cyclopentylmethyl-1-(4-methanesulfonyl-phenyl)-cyclopropanecarboxylic acid thiazol-2-ylamide into its enantiomers (±)-(E)-2-Cyclopentylmethyl-1-(4-methanesulfonyl-phenyl)-cyclopropanecarboxylic acid thiazol-2-ylamide can be separated into its enantiomers via chromatography on a DIACEL Chiralpak AD column, eluting with 25% isopropanol and 75% hexane. Under the conditions given, the first enantiomer to elute is enantiomer 1. $^1$H-NMR and mass spectral data for the enantiomers are identical to those of the racemate described in example 56.

EXAMPLE 58

(±)-(E)-2-Cyclopentyl-1-(4-methanesulfonyl-phenyl)-cyclopropanecarboxylic acid (5-ethyl-[1,3,4]thiadiazol-2-yl)-amide

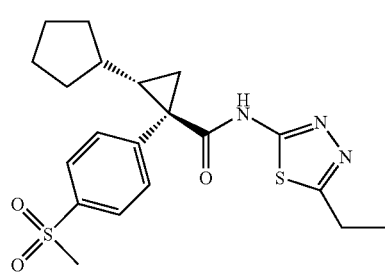

¹H-NMR (CDCl₃) δ=0.86 (m, 1H), 1.25-1.54 (m, 8H), 1.56-1.75 (m, 4H), 1.79-1.87 (m, 1H), 2.10-2.22 (m, 1H), 3.04 (q, 2H), 3.18 (s, 3H), 5.42 (s, 1H), 7.61-7.68 (m, 2H), 8.00-8.08 (m, 2H). MS (m/e): 420.1 (M+H).

EXAMPLE 59

(±)-(Z)-2-Cyclopentyl-1-{5-[(pyridin-3-ylmethyl)-sulfamoyl]-thiophen-2-yl}-cyclopropanecarboxylic acid thiazol-2-ylamide

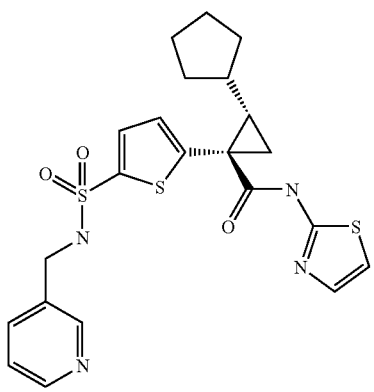

¹H-NMR (CDCl₃): δ=1.12-1.30 (m, 2H), 1.37-1.55 (m, 4H), 1.60-1.75 (m, 3h), 1.76-1.90 (m, 1H), 1.95-2.05 (m, 1H), 2.17-2.30 (m, 1H), 4.44-4.51 (m, 2H), 7.10 (mc, 1H), 7.14 (mc, 1H), 7.58 (mc, 2H), 7.74 (mc, 1H) 8.36 (mc, 1H), 8.64 (mc, 1H), 8.91 (s, 1H). MS (m/e): 489.0 (M+H).

EXAMPLE 60

(±)-(Z)-2-Cyclopentyl-1-(5-methanesulfonyl-thiophen-2-yl)-cyclopropanecarboxylic acid (5-chloro-thiazol-2-yl)-amide

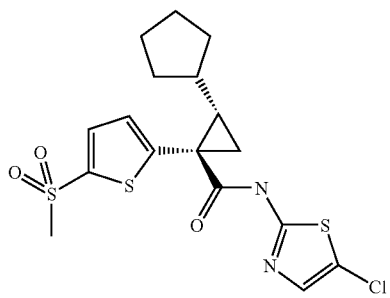

¹H-NMR (CDCl₃): δ=0.85-0.95 (m, 1H), 1.05-1.18 (m, 1H), 1.24-1.54 (m, 4H), 1.60-1.82 (m, 4H), 1.91-1.99 (m, 1H), 2.13-2.25 (m, 1H), 3.23 (s,-3H), 7.16 (mc, 1H), 7.23 (s, 1H), 7.68 (mc, 1H). MS (m/e): 431.0/433.0 (M+H).

EXAMPLE 61

(±)-(E)-2-Cyclohexyl-1-[3-(2-pyridin-2-yl-ethylsulfamoyl)-phenyl]-cyclopropanecarboxylic acid thiazol-2-ylamide

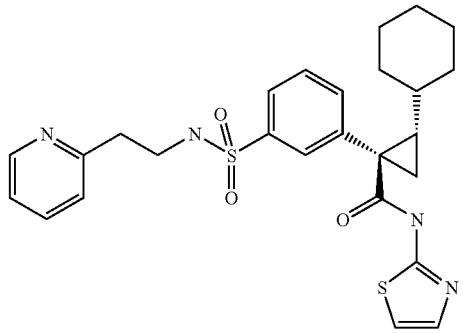

¹H-NMR (CDCl₃) δ=0.25 (mc, 1H), 0.77-1.85 (m, 12H), 2.05 (mc, 1H), 2.96 (mc, 2H), 3.42 (mc, 2H), 6.50 (mc, 1H), 6.91 (mc, 1H), 7.11 (mc, 2H), 7.30 (mc, 1H), 7.41-7.72 (m, 3 H), 7.90 (mc, 2H), 8.44 (mc, 1H). MS (m/e): 511 (M+H).

EXAMPLE 62

(±)-(E)-3-Cyclohexyl-2,2-difluoro-1-(4-methanesulfonyl-phenyl)-cyclopropanecarboxylic acid thiazol-2-ylamide

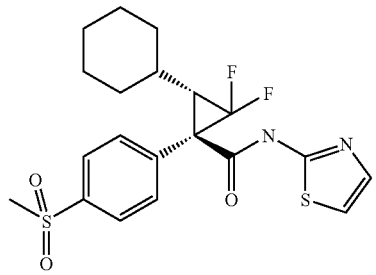

¹H-NMR (CDCl₃) δ=0.81-1.32 (m, 6H), 1.53-1.81 (m, 5H), 2.77 (mc, 1H), 3.08 (s, 3 H), 7.12 (mc, 1H), 7.53 (mc, 1H), 7.74 (mc, 2H), 7.98 (mc, 2H). MS (m/e): 441 (M+H).

EXAMPLE 63

Separation of (±)-(E)-3-Cyclohexyl-2,2-difluoro-1-(4-methanesulfonyl-phenyl)-cyclopropanecarboxylic acid thiazol-2-ylamide into its enantiomers (±)-(E)-3-Cyclohexyl-2,2-difluoro-1-(4-methanesulfonyl-phenyl)-cyclopropanecarboxylic acid thiazol-2-ylamide can be separated into its enantiomers via chromatography on a Chiralpak AD_column, eluting with hexane TFA 0.05%/iso-propanol 75:25. Under the conditions given the first enantiomer to elute is enantiomer 1.

EXAMPLE 64

(±)-(E)-2-Cyclohexyl-1-[4-(2-pyridin-2-yl-ethylsulfamoyl)-phenyl]-cyclopropanecarboxylic acid thiazol-2-ylamide

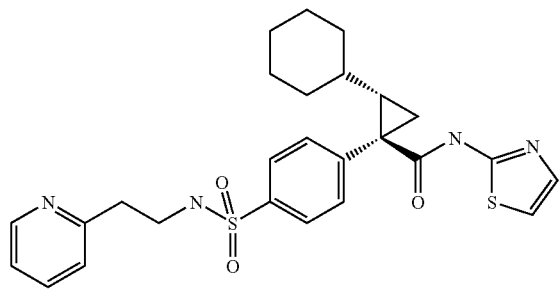

¹H-NMR (CDCl₃) δ=0.16-0.26 (m, 1H), 0.80-1.83 (m, 12H), 2.04 (mc, 1H), 3.01 (m, 2), 3.49 (m, 2H), 6.35 (b, 1H), 6.93 (mc, 1H), 7.15 (mc, 2H), 7.34 (mc, 1H), 7.54 (mc, 2H), 7.60 (mc, 1H), 7.93 (mc, 2H), 8.50 (mc, 1H). MS (m/e): 511 (M+H).

EXAMPLE 65

(±)-(E)-2-Cyclopentyl-1-(4-methanesulfonyl-phenyl)-cyclopropanecarboxylic acid (5-fluoro-thiazol-2-yl)-amide

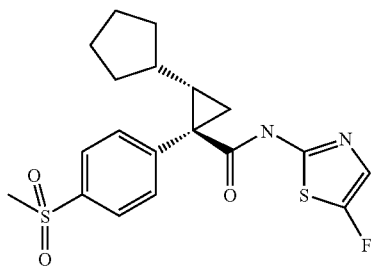

¹H-NMR (CDCl₃) δ=0.74-0.93 (m, 1H), 1.20-1.73 (m, 9H), 1.82 (mc, 1H), 2.13 (mc, 1H), 3.16 (s, 3H), 6.93 (d, 3 Hz, 1H), 7.63 (mc, 2H), 8.03 (mc, 2H). MS (m/e): 409 (M+H).

EXAMPLE 66

(±)-(Z)-2-Cyclohexyl-1-(5-methylsulfamoyl-thiophen-2-yl)-cyclopropanecarboxylic acid thiazol-2-ylamide

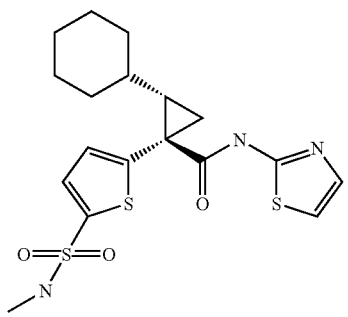

¹H-NMR (CDCl₃) δ=0.40-0.58 (m, 1H), 0.81-1.35 (m, 7H), 1.52-1.74 (m, 3H), 1.76-1.92 (m, 2H), 2.00-2.16 (m, 1H), 2.76-2.85 (m, 3H), 5.01-5.14 (m, 1H), 6.93-7.00 (m, 1H), 7.09-7.15 (m, 1H), 7.33-7.40 (m, 1H), 7.53-7.60 (m, 1H), 8.93-9.13 (bs, 1H). MS (m/e): 426 (M+H).

EXAMPLE 67

(±)-(Z)-2-Cyclohexyl-1-(5-methylsulfamoyl-thiophen-2-yl)-cyclopropanecarboxylic acid (5-chloro-thiazol-2-yl)-amide

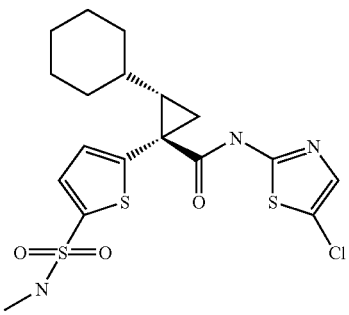

¹H-NMR (CDCl₃) δ=0.43-0.59(m, 1H), 0.78-1.37 (m, 7H), 1.47-1.74 (m, 3H), 1.77-1.93 (m, 2H), 1.99-2.13 (m, 1H), 2.78-2.87 (m, 3H), 4.58-4.69 (m, 1H), 7.10-7.16 (m, 1H), 7.21 (s, 1H), 7.55-7.60 (m, 1H), 8.71-8.86 (bs, 1H). MS (m/e): 460 (M+H).

EXAMPLE 68

(±)-(Z)-2-Cyclohexyl-1-(5-methanesulfonyl-thiophen-2-yl)-cyclopropanecarboxylic acid (5-chloro-thiazol-2-yl)-amide

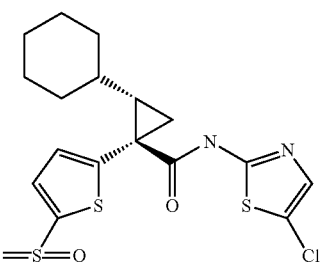

¹H-NMR (CDCl₃) δ=0.41-0.59 (m, 1H), 0.92-1.28 (m, 6H), 1.30-1.38 (m, 1H), 1.51-1.74 (m, 3H), 1.76-1.87 (m, 1H), 1.88-1.96 (m, 1H), 2.01-2.15 (m, 1H), 3.26 (s, 3H), 7.16-7.20 (m, 1H), 7.21 (s, 1H), 7.67-7.75 (m, 1H), 8.64-8.85 (bs, 1H). MS (m/e): 445 (M+H).

EXAMPLE 69

(±)-(E)-2-Cyclohexyl-1-(4-methanesulfonyl-3-trifluoromethoxy-phenyl)-cyclopropanecarboxylic acid [1,3,4]thiadiazol-2-ylamide

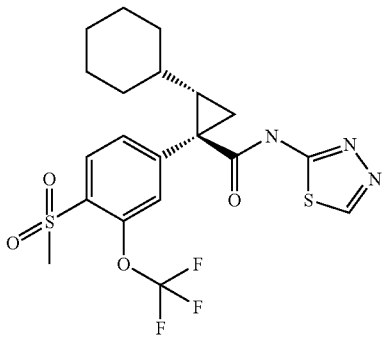

¹H-NMR (CDCl₃) δ=0.20-0.35 (m, 1H), 0.85-1.34 (m, 7H), 1.57-1.85 (m, 5H), 2.03-2.15 (m, 1), 3.33 (s, 3H), 7.48-7.57 (m, 2H), 8.17-8.23 (m, 1H), 8.71-8.78 (bs, 1H), 8.80 (s, 1H). MS (m/e): 490 (M+H).

EXAMPLE 70

(±)-(E)-2-Cyclohexyl-1-(4-methylsulfamoyl-3-trifluoromethyl-phenyl)-cyclopropanecarboxylic acid thiazol-2-ylamide

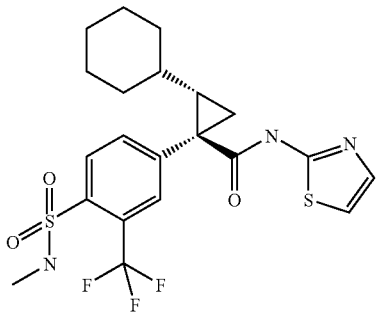

¹H-NMR (CDCl₃) δ0.11-0.27 (m, 1H), 0.81-1.31 (m, 7H), 1.59-1.81 (m, 5H), 2.05-2.17 (m, 1H), 2.79 (d, J=5.04, 3H), 5.25-5.35 (m, 1H), 6.95-6.98 (m, 1H), 7.34-7.38 (m, 1H), 7.73-7.79 (m, 1H), 7.87-7.91 (m, 1H), 8.26-8.31, (m, 1H), 8.52-8.62 (bs, 1H). MS (m/e: 488 (M+H).

EXAMPLE 71

(±)-(E)-2-Cyclohexyl-1-(4-methylsulfamoyl-3-trifluoromethyl-phenyl)-cyclopropanecarboxylic acid [1,3,4]thiadiazol-2-ylamide

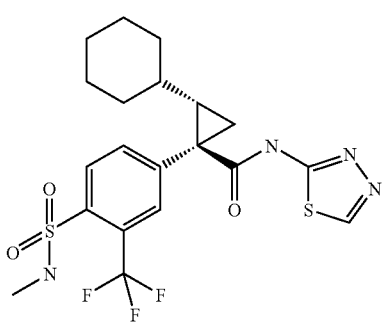

¹H-NMR (CDCl₃) δ=0.13-0.28 (m, 1H), 0.81-1.28 (m, 6H), 1.31-1.37 (m, 1H), 1.51-1.81 (m, 5H), 2.06-2.18 (m, 1H), 2.75 (d, J=2.63, 1H), 5.93-6.05 (m, 1H), 7.72-7.79 (m, 1H), 7.86-7.90 (m, 1H), 8.25-8.32 (m, 1H), 8.79 (s, 1H), 9.27-9.37 (bs, 1H). MS (m/e): 489 (M+H).

EXAMPLE 72

(±)-(E)-2-Cyclohexyl-1-(3-nitro-phenyl)-cyclopropanecarboxylic acid thiazol-2-ylamide

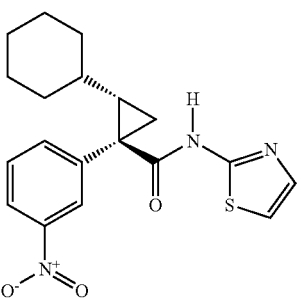

¹H-NMR (CDCl₃) δ=0.18-0.36 (m, 1H), 0.82-1.33 (m, 7H), 1.49-1.72 (m, 3H), 1.73-1.85 (m, 2H), 2.03-2.18 (m, 1H), 6.91-6.99 (m, 1H), 7.31-7.39 (m, 1H), 7.59-7.72 (m, 1H), 7.76-7.83 (m, 1H), 8.24-8.33 (m, 2H), 8.39-8.51 (bs, 1H);

MS (m/e): 372 (M+H).

EXAMPLE 73

(±)-(E)-4-[2-Cyclopentyl-1-(thiazol-2-ylcarbamoyl)-cyclopropyl]-benzoic acid methyl ester

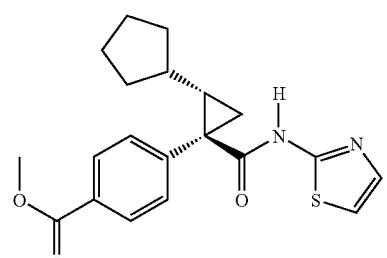

¹H-NMR (CDCl₃) δ=0.80-0-98 (m, 1H), 1.23-1.83 (m, 10H), 2.06-2.11 (m, 1H), 3.98 (s, 3H), 6.89-6.93 (m, 1), 7.31-7.36 (m, 1H), 7.48-7.55 (m, 2H), 8.08-8.16 (m, 2H), 8.37-8.46 (bs, 1H). MS (m/e): 371 (M+H).

EXAMPLE 74

(±)-(E)-3-[2-Cyclohexyl-1-(thiazol-2-ylcarbamoyl)-cyclopropyl]-N-pyridin-3-ylmethyl-benzamide

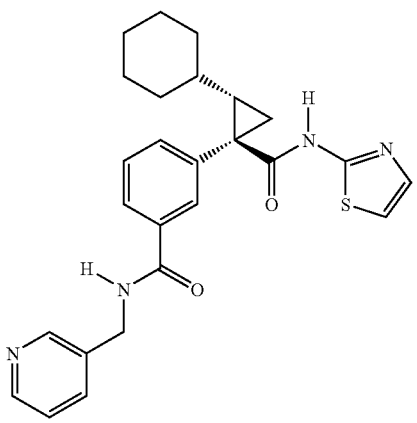

$^1$H-NMR (CDCl$_3$) δ=0.22-0.40 (m, 1H), 0.77-1.88 (m, 12H), 1.96-2.11 (m, 1H), 4.58-4.77 (m, 2H), 6.66-6.80 (m, 1H), 6.87-6.95 (m, 1H), 7.27-7.35 (m, 2H), 7.45-7.64 (m, 2H), 7.70-7.83 (m, 2H), 7.86-792 (m, 1H), 8.38-8.70 (m, 3H). MS (m/e): 461 (M+H).

EXAMPLE 75

(±)-(E)-3-[2-Cyclohexyl-1-(thiazol-2-ylcarbamoyl)-cyclopropyl]-N-methyl-benzamide

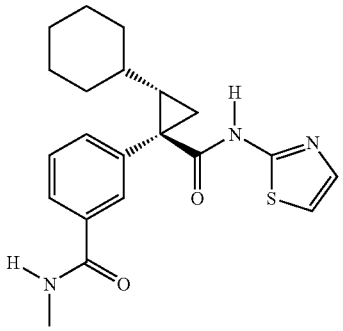

$^1$H-NMR (CDCl$_3$) δ=0.21-0.41(m, 1H),0.78-1.75 (m, 11H), 1.77-1.87 (m, 1H), 1.97-2.11 (m, 1H), 3.00-3.09 (m, 3H), 6.10-6.27 (m, 1H), 6.88-6.96 (m, 1H), 7.29-7.35 (m, 1H), 7.45-7.60 (m, 2H), 7.71-7.76 (m, 1H), 7.83-7.87 (m, 1H), 8.46 (bs, 1H). MS (m/e): 3.84 (M+H).

EXAMPLE 76

(±)-(E)-2-Cyclohexyl-1-(3-methanesulfonylamino-phenyl)-cyclopropanecarboxylic acid thiazol-2-yla-mide

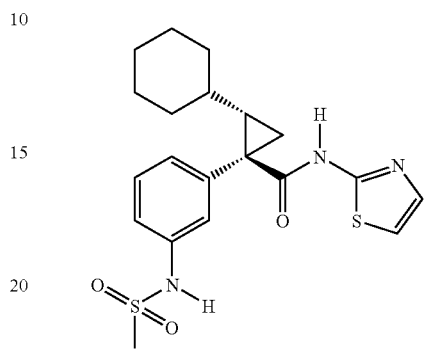

$^1$H-NMR (CDCl$_3$) δ=0.24-0.45 (m, 1H), 0.82-1.74 (m, 11H), 1.78-1.89 (m, 1H), 1.95-2.08 (m, 1H), 3.05 (s, 3H), 6.69 (s, 1H), 6.93-6.99 (m, 1H), 7.14-7.23 (m, 2H), 7.29-7.46 (m, 3H), 9.68-10.24 (bs, 1H). MS (m/e): 420 (M+H).

EXAMPLE 77

(±)-(E)-2-Cyclohexyl-1-(4-methanesulfonyl-phenyl)-cyclopropanecarboxylic acid (5-methyl-thiazol-2-yl)-amide

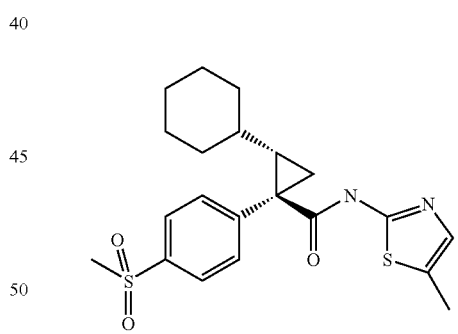

Following the method of example 39g, reaction of (±)-(E)-2-cyclohexyl-1-(4-methanesulfonyl-phenyl)-cyclopropan-ecarboxylic acid (15 mg, 0.05 mmol) with TBTU (16.4 mg, 0.05 mmol), triethylamine (9.5 mg, 0.10 mmol) and 5-methyl-thiazol-2-ylamine (5.83 mg, 0.05 mmol) in 1.0 mL THF and eluting with a gradient from 100:0 to 0:100 hexane:ethyl acetate gives the title compound as a white solid (4.7 mg). $^1$H-NMR (CDCl$_3$) δ=0.15-0.33 (m, 1H), 0.79-1.82 (m, 12H), 1.99-2.12 (m, 1H), 2.34-2.40 (m, 3H), 3.15 (s, 3H), 6.98 (s, 1H), 7.57-7.67 (m, 2H), 7.97-8.07 (m, 2H). MS (m/e): 419 (M+H).

EXAMPLE 78

(±)-(E)-2-Cyclohexyl-1-(4-dimethylamino-phenyl)-cyclopropanecarboxylic acid thiazol-2-ylamide

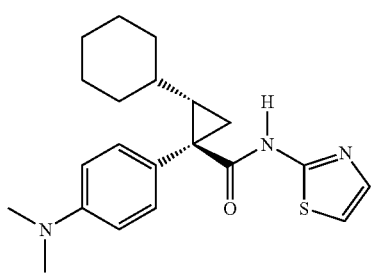

¹H-NMR (CDCl₃) δ=0.38-0.56 (m, 1H), 0.78-1.71 (m, 11H), 1.80-1.99 (m, 2H), 3.00 (s, 6H), 6.67-6.78 (m, 2H), 6.84-6.92 (m, 1H), 7.17-7.26 (m, 2H), 7.28-7.37 (m, 1H), 8.52-8.87 (bs, 1H). MS (m/e): 370 (M+H).

EXAMPLE 79

(E)-2-isopropyl-2-(4-methanesulfonyl-phenyl)-cyclopropane carboxylic acid thiazol-2-ylamide

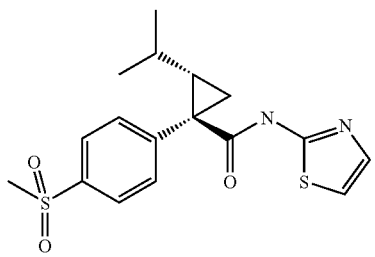

a) Ethyl (E)-4-methyl-2-(4-methylsulfanyl-phenyl)-pentenoate using 4-(methylthio)-phenyl boronic acid and (Z)-Ethyl 2-iodo-4-methyl-pent-2-enoate according to General Procedure IIb.
b) Ethyl (E)-4-methyl-2-(4-methylsulfonyl-phenyl)-pentenoate according to General Procedure IIIa.
c) (E)-2-(4-methanesulfonyl-phenyl)-4-methyl-2-penten-1-ol according to General Procedure IV.
d) (E)-1-(4-methanesulfonyl-phenyl)-(2-isopropyl-cyclopropyl)-methanol, according to General Procedure V; purification by flash chromatography, eluting with hexanes: ethyl acetate (1:1) gives the title compound as a colorless solid.
e) (E)-2-isopropyl-2-(4-methanesulfonyl-phenyl)-cyclopropane carboxylic acid, according to General Procedure VI, colorless solid.
f) (E)-2-isopropyl-2-(4-methanesulfonyl-phenyl)-cyclopropane carboxylic acid thiazol-2-ylamide, according to General Procedure VIIa, colorless solid, MS(M⁺+H)=365.

EXAMPLE 80

(E)-2-cyclohexyl-2-(4-methanesulfonyl-phenyl)-cyclopropane carboxylic acid thiazol-2-ylamide

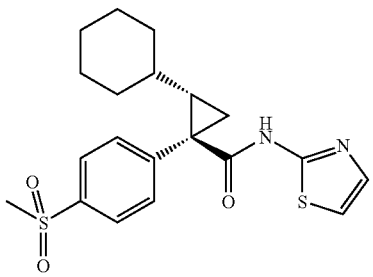

a) Ethyl (E)-3-cyclohexyl-2-(4-methylsulfanyl-phenyl)-acrylate: using 4-(methylthio)-phenyl boronic acid and (Z)-Ethyl 2-bromo-3-cyclohexyl-prop-2-enoate according to General Procedure IIb.
b) Ethyl (E)-3-cyclohexyl-2-(4-methylsulfonyl-phenyl)-acrylate according to General Procedure IIIa.
c) (E)-2-(4-methanesulfonyl-phenyl)-3-cyclohexyl-2-propen-1-ol according to General Procedure IV.
d) (E)-1-(4-methanesulfonyl-phenyl)-(2-cyclohexyl-cyclopropyl)-methanol, according to General Procedure V. Purification by flash chromatography, eluting with hexanes: ethyl acetate (4:1) gives the compound as a white solid.
e) (E)-2-cyclohexyl-2-(4-methanesulfonyl-phenyl)-cyclopropane carboxylic acid, according to General Procedure VI, colorless solid.
f) (E)-2-cyclohexyl-2-(4-methanesulfonyl-phenyl)-cyclopropane carboxylic acid thiazol-2-ylamide, according to General Procedure VIIa, colorless solid, MS(M⁺+H)=405. The racemic mixture was resolved by using a preparative chiraal chromatography using ethanol as eluent.

EXAMPLE 81

(E)-2-cyclopentyl-2-(4-methanesulfonyl-phenyl)-cyclopropane carboxylic acid thiazol-2-ylamide

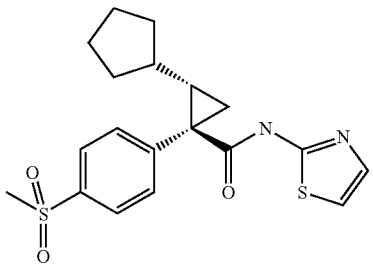

a) Ethyl (E)-3-cyclopentyl-2-(4-methylsulfanyl-phenyl)-acrylate using (Z)-Ethyl 3-cyclopentyl-2-iodo-propenoate according to General Procedure IIb.
b) Ethyl (E)-3-cyclopentyl-2-(4-methylsulfonyl-phenyl)-acrylate according to General Procedure IIIa.
c) 2-(4-methanesulfonyl-phenyl)-3-cyclopentyl-2-propen-1-ol according to General Procedure IV.
d) (E)-1-(4-methanesulfonyl-phenyl)-(2-cyclopentyl-cyclopropyl)-methanol, according to General Procedure V; purification by flash chromatography, eluting with hexanes: ethyl acetate (2:1 to 1:1) gives the compound as a white solid.
e) (E)-2-cyclopentyl-2-(4-methanesulfonyl-phenyl)-cyclopropane carboxylic acid, according to General Procedure VI, colorless solid.
f) (E)-2-cyclopentyl-2-(4-methanesulfonyl-phenyl)-cyclopropane carboxylic acid thiazol-2-ylamide, according to General Procedure VIIa, colorless solid, MS(M$^+$+H)=391.

EXAMPLE 82

(E)-2-Cyclohexyl-2-(4-methanesulfonyl-phenyl)-cyclopropane carboxylic acid 5-methyl-thiazol-2-ylamide

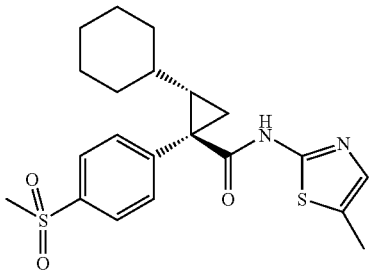

a) Ethyl (E)-3-cyclohexyl-2-(4-methylsulfanyl-phenyl)-acrylate using (Z)-Ethyl 3-cyclohexyl-2-iodo-propenoate according to General Procedure IIb.
b) Ethyl (E)-3-cyclohexyl-2-(4-methylsulfonyl-phenyl)-acrylate according to General Procedure IIIa.
c) 2-(4-Methanesulfonyl-phenyl)-3-cyclohexyl-2-propen-1-ol according to General Procedure IV.
d) (E)-1-(4-Methanesulfonyl-phenyl)-(2-cyclohexyl-cyclopropyl)-methanol, according to General Procedure V; purification by flash chromatography, eluting with hexanes: ethyl acetate (2:1 to 1:1) gives the compound as a colorless solid.
e) (E)-2-Cyclohexyl-2-(4-methanesulfonyl-phenyl)-cyclopropane carboxylic acid, according to General Procedure VI, colorless solid.
f) (E)-2-Cyclohexyl-2-(4-methanesulfonyl-phenyl)-cyclopropane carboxylic acid 5-methyl-thiazol-2-ylamide, according to General Procedure VIIa, using 2-amino-5-methyl-thiazole, colorless solid, MS(M$^+$+H)=419.

The compounds of the present invention may be used as medicaments in human or veterinary medicine. The compounds may be administered by various routes, for example, by oral or rectal routes, topically or parenterally, for example by injection, and are usually employed in the form of a pharmaceutical composition.

Such compositions may be prepared by methods well known in the pharmaceutical art and normally comprise at least one active compound in association with a pharmaceutically acceptable diluent or carrier. In making the compositions of the present invention, the active ingredient will usually be mixed with a carrier or diluted by a carrier, and/or enclosed within a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, solutions, syrups, aerosol (as a solid or in a liquid medium), ointments containing, for example, up to 10% by weight of the active compound, soft and hard gelatin capsules, suppositories, injection solutions and suspensions and sterile packaged powders.

Some examples of suitable carriers are lactose, dextrose, vegetable oils, benzyl alcohols, alkylene glycols, polyethylene glycols, glycerol triacetate, gelatin, carbohydrates such as starch and petroleum jelly, sucrose sorbitol, mannitol, starches, gum acacia, calcium phosphate, alginates, tragacanth, gelatin, syrup, methyl cellulose, methyl-and propyl-hydrobenzoate, talc, magnesium stearate and mineral oil. The compounds of formula I can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins. Compositions of the invention may be formulated so as to provide, quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary doses for human subjects and other mammals, each unit containing a predetermined quantity of active material calculated to produce the desired therapeutic effect, in association with a suitable pharmaceutical carrier.

EXAMPLE A

Tablets containing the following ingredients can be produced in a conventional manner:

| Ingredients (mg per capsule) | |
| --- | --- |
| Compound of formula I | 10.0-100.0 |
| Lactose | 125.0 |
| Corn starch | 75.0 |
| Talc | 4.0 |
| Magnesium stearate | 1.0 |

EXAMPLE B

Capsules containing the following ingredients can be produced in a conventional manner:

| Ingredients (mg per capsule) | |
| --- | --- |
| Compound of formula I | 25.0 |
| Lactose | 150.0 |
| Corn starch | 20.0 |
| Talc | 5.0 |

The pharmacological profile of the present compounds may be demonstrated as follows:

An enzymatic coupled glucokinase (GK) assay using purified recombinant human islet GK was used to evaluate effects of the activators. In this assay, GK catalyzes glucose phosphorylation in the presence of ATP. The product of this reaction, glucose-6-phosphate, is then oxidized by an excess of glucose-6-dehydrogenase to produce gluconate-6-phosphate with concomitant reduction of $NAD^+$ to NADH (Davidson and Arion, 1987). The following outlines the two reactions involved:

Glucose+ATP→Glucose-6-P+ADP (Glucokinase)
Glucose-6-P+NAD→Gluconate-6-P+NADH (glucose-6-P dehydrogenase)

The NADH production detected by absorbance at 340 nm is used to monitor the enzymatic activity.

The human islet GK isoform was expressed in E. coli as $(His)_6$-tagged fusion protein and purified with metal chelate affinity chromatography (Tiedge et al., 1997). After purification the enzyme was stored in aliquots at concentration 0.8 mg/ml in 25 mM $NaH_2PO_4$, 150 mM NaCl, 100 mM imidazole, 1 mM DTT, 50% glycerol at −80° C.

The assay was performed in flat bottom 96-well plates in a final incubation volume of 100 µl. The incubation mixture consisted of 25 mM HEPES (pH7.4), 50 mM KCl, 2.5 mM $MgCl_2$, 2 mM dithiothreitol, 4 U/ml glucose-6-phosphate dehydrogenase from Leuconostoc mesenteroides, 5 mM ATP, 1 mM NAD and 10 mM glucose. All reagents were from Sigma-Aldrich Co. (St. Louis, Mo.). Test compounds were dissolved in DMSO and then added to the reaction mixture giving the final DMSO concentration of 10%.

The reaction was initiated by addition of 20 µl GK and run for 20 min at 37° C. The amount of formed NADH was measured as an increase in absorbance at 340 nm using a microplate reader.

The concentration of activator that produced 50% of maximum increase in the activity of GK ($EC_{50}$) was calculated. The preferred compounds of formula I described within the examples have an $EC_{50}$ less than or equal to 30 µM.

| EXAMPLE | EC50 (µM) |
| --- | --- |
| 2 | 1.18 |
| 3 | 5.46 |
| 7 | 0.70 |
| 11 | 9.32 |
| 13 | 12.65 |
| 20 | 1.90 |
| 26 | 0.36 |
| 35 | 7.61 |
| 48 | 8.69 |
| 45 | 0.16 |
| 50 | 7.61 |
| 51 | 10.48 |
| 52 | 3.82 |
| 55 (Isomer 1) | 0.15 |
| 63 (Isomer 2) | 5.30 |
| 73 | 3.66 |
| 77 | 0.39 |

EC50 values shown in the above table are at 10 mM glucose.

REFERENCES

Davidson A. L. and Arion W. J. Factors underlying significant underestimations of glucokinase activity in crude liver extracts: physiological implications of higher cellular activity. Arch. Biochem. Biophys. 253, 156-167, 1987.

Tidge M, Krug U. and Lenzen S. Modulation of human glucokinase intristic activity by SH reagents mirrors post-translational regulation of enzyme activity. Biochem. Biophys. Acta 1337, 175-190, 1997.

The invention claimed is:
1. A compound of the formula

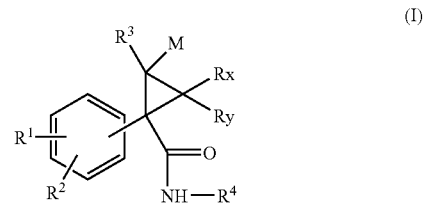

wherein
M is hydrogen, halo, lower alkyl, or perfluoro lower alkyl; and

Rx and Ry are hydrogen, halo or methyl; and $R^1$ and $R^2$ are independently hydrogen, halo, amino, hydroxyamino, nitro, cyano, sulfonamido, lower alkyl, —$OR^5$, —$COOR^5$, perfluoro-lower alkyl, lower alkyl thio, perfluoro-lower alkyl thio, lower alkyl sulfonyl, perfluoro lower alkyl sulfonyl, lower alkyl sulfinyl, $R^5$ is hydrogen, lower alkyl or perfluoro-lower alkyl; or furthermore $R^1$, $R^2$ can be —$(CH_2)n$-$NR^6R^7$, with n=1, 2, 3 or 4 and $R^6$ and $R^7$ are independently hydrogen or lower alkyl; or together with the nitrogen atom to which they are attached form a five or six-membered heteroaromatic ring containing from 1 to 3 heteroatoms selected from sulfur, oxygen or nitrogen; or a saturated 5- or 6-membered cycloheteroalkyl ring, which contains from 1 to 2 heteroatoms selected from the group consisting of oxygen, sulfur and nitrogen; or $R^1$, $R^2$ can be alkynyl, substituted with hydrogen, lower alkyl, hydroxy lower alkyl, lower alkoxy lower alkyl, an unsubstituted or hydroxy substituted cycloalkyl ring containing 5 or 6 carbon atoms, a five- or six-membered saturated heterocyclic ring which contains from 1 to 3 hetero atoms selected from the group consisting of sulfur, oxygen or nitrogen, or an unsubstituted five- or six-membered heteroaromatic ring, connected by a ring carbon atom, which contains from 1 to 3 heteroatoms in the ring selected from the group consisting of sulfur, nitrogen and oxygen, or —$(CH_2)n$-$NR^8R^9$, with n=1, 2, and $R^8$ and $R^9$ are independently hydrogen or lower alkyl; or together with the nitrogen atom to which they are attached form a five or six-membered heteroaromatic ring containing from 1 to 3 heteroatoms selected from sulfur, oxygen or nitrogen; or a saturated 5- or 6-membered cycloheteroalkyl ring, which contains from 1 to 2 heteroatoms selected from the group consisting of oxygen, sulfur and nitrogen; or $R^1$, $R^2$ can be R10—[$(CH2)y$-W]z-, with W is oxygen, sulfur, —SO—, —$SO_2$—, and R10 is a heteroaromatic ring, connected by a ring carbon atom, which contains from 5 to 6 ring members with from 1 to 2 heteroatoms selected from the group consisting of oxygen, sulfur or nitrogen, or aryl containing 6 or 10 ring carbon atoms, or aryl containing from 6 ring carbon atoms fused with a heteroaromatic ring containing 5 or 6 ring members with 1 or 2 heteroatoms in the ring being selected from the group consisting of nitrogen, oxygen or sulfur, or a saturated 5- or 6-membered cycloheteroalkyl ring, which contains from 1 to 2 heteroatoms selected from the group consisting of oxygen, sulfur and nitrogen, or a cycloalkyl ring having 5 or 6 carbon atoms, or
—NR$^{11}$R$^{12}$, with R$^{11}$ and R$^{12}$ are independently hydrogen or lower alkyl;
y is independently 0, 1, 2, 3 or 4; z is independently 0,1; or
R$^1$, R$^2$ can be R$^{13}$—(CH$_2$)t-U—, with
U is —NHCO—, —CONH—, —NHSO$_2$—, —SO$_2$NH— and
R$^{13}$ in the same meaning of R$^{10}$ and
perfluoro-lower alkyl, lower alkyl, lower alkoxycarbonyl or
—NR$^{14}$R$^{15}$, R$^{14}$ and R$^{15}$ are independently hydrogen or lower alkyl; or together with the nitrogen atom to which they are attached form a five or six-membered heteroaromatic ring containing from 1 to 3 heteroatoms selected from sulfur, oxygen or nitrogen; or a saturated 5- or 6-membered heterocycloalkyl ring, which contains from 1 to 2 heteroatoms selected from the group consisting of oxygen, sulfur and nitrogen;
t is an integer being 0, 1, 2, 3 or 4;
R$^3$ is —(CH$_2$)s-V where V is a 3 to 8-membered cycloalkyl;
s is independently 0, 1 or 2;
R$^4$ is —C(O)NHR$^{16}$, or is R$^{17}$;
R$^{16}$ is hydrogen, lower alkyl, lower alkenyl, hydroxy lower alkyl, —(CH$_2$)n-COOR$^{18}$, —CO—(CH$_2$)n-COOR$^{19}$;
R$^{17}$ is an unsubstituted, mono- or di-substituted five- or six-membered heteroaromatic ring connected by a ring carbon atom to the amide group shown, which five- or six-membered heteroaromatic ring contains from 1 to 4 heteroatoms selected from sulfur, oxygen or nitrogen, with one heteroatom being nitrogen which is adjacent to the connecting ring carbon atom; said mono- or di-substituted heteroaromatic ring being mono- or di-substituted at a position on a ring carbon atom other than adjacent to said connecting carbon atom with a substituent selected from the group consisting of lower alkyl, halo, nitro, cyano, —(CH$_2$)n-OR$^{20}$, —(CH$_2$)n-COOR$^{21}$, —(CH$_2$)n-CONHR$^{22}$, —(CH$_2$)n-NHR$^{23}$,
n is 0, 1, 2, 3 or 4;
R$^{18}$, R$^{19}$, R$^{20}$, R$^{21}$, R$^{22}$ and R$^{23}$ are independently hydrogen or lower alkyl,
and its pharmaceutically acceptable salts thereof.

2. A compound according to claim 1 having the formula

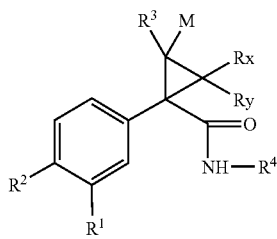

(I-A)

wherein
M is hydrogen, halo, lower alkyl or perfluoro lower alkyl; and
Rx and Ry are hydrogen, halo or methyl; and
R$^1$ and R$^2$ are independently hydrogen, halo, amino, hydroxyamino, nitro, cyano, sulfonamido, lower alkyl, —OR$^5$, —COOR$^5$, perfluoro-lower alkyl, lower alkyl thio, perfluoro-lower alkyl thio, lower alkyl sulfonyl, perfluoro lower alkyl sulfonyl, lower alkyl sulfinyl,
R$^5$ is hydrogen, lower alkyl or perfluoro-lower alkyl; or furthermore R$^1$, R$^2$ can be —(CH$_2$)n-NR$^6$R$^7$, with n=1, 2, 3 or 4 and
R$^6$ and R$^7$ are independently hydrogen or lower alkyl; or together with the nitrogen atom to which they are attached form a five or six-membered heteroaromatic ring containing from 1 to 3 heteroatoms selected from sulfur, oxygen or nitrogen; or a saturated 5- or 6-membered cycloheteroalkyl ring, which contains from 1 to 2 heteroatoms selected from the group consisting of oxygen, sulfur and nitrogen; or
R$^1$, R$^2$ can be alkynyl,
substituted with hydrogen, lower alkyl, hydroxy lower alkyl, lower alkoxy lower alkyl, an unsubstituted or hydroxy substituted cycloalkyl ring containing 5 or 6 carbon atoms, a five- or six-membered saturated heterocyclic ring which contains from 1 to 3 hetero atoms selected from the group consisting of sulfur, oxygen or nitrogen, or an unsubstituted five- or six-membered heteroaromatic ring, connected by a ring carbon atom, which contains from 1 to 3 heteroatoms in the ring selected from the group consisting of sulfur, nitrogen and oxygen, or —(CH$_2$)n-NR8R9, with n=1, 2, and
R$^8$ and R$^9$ are independently hydrogen or lower alkyl; or together with the nitrogen atom to which they are attached form a five or six-membered heteroaromatic ring containing from 1 to 3 heteroatoms selected from sulfur, oxygen or nitrogen; or a saturated 5- or 6-membered cycloheteroalkyl ring, which contains from 1 to 2 heteroatoms selected from the group consisting of oxygen, sulfur and nitrogen; or
R$^1$, R$^2$ can be R10—[(CH2)y-W]z-, with
W is oxygen, sulfur, —SO—, —SO$_2$—, and
R10 is a heteroaromatic ring, connected by a ring carbon atom, which contains from 5 to 6 ring members with from 1 to 2 heteroatoms selected from the group consisting of oxygen, sulfur or nitrogen, or
aryl containing 6 or 10 ring carbon atoms, or
aryl containing from 6 ring carbon atoms fused with a heteroaromatic ring containing 5 or 6 ring members with 1 or 2 heteroatoms in the ring being selected from the group consisting of nitrogen, oxygen or sulfur, or
a saturated 5- or 6-membered cycloheteroalkyl ring, which contains from 1 to 2 heteroatoms selected from the group consisting of oxygen, sulfur and nitrogen, or
a cycloalkyl ring having 5 or 6 carbon atoms, or
—NR$^{11}$R$^{12}$, with R$^{11}$ and R$^{12}$ are independently hydrogen or lower alkyl;
y is independently 0, 1, 2, 3 or 4; z is independently 0, 1; or
R$^1$, R$^2$ can be R$^{13}$—(CH$_2$)t-U—, with
U is —NHCO—, —CONH—, —NHSO$_2$—, —SO$_2$NH— and
R$^{13}$ in the same meaning of R$^{10}$ and perfluoro-lower alkyl, lower alkyl, lower alkoxycarbonyl or
—NR$^{14}$R$^{15}$, R$^{14}$ and R$^{15}$ are independently hydrogen or lower alkyl; or together with the nitrogen atom to which they are attached form a five or six-membered heteroaromatic ring containing from 1 to 3 heteroatoms selected from sulfur, oxygen or nitrogen; or a saturated 5- or 6-membered heterocycloalkyl ring, which contains from 1 to 2 heteroatoms selected from the group consisting of oxygen, sulfur and nitrogen;
t is an integer being 0, 1, 2, 3 or 4;
R$^3$ is —(CH$_2$)s-V where V is a 3 to 8-membered cycloalkyl;
s is independently 0, 1 or 2;
R$^4$ is —C(O)NHR$^{16}$, or is R$^{17}$;
R$^{16}$ is hydrogen, lower alkyl, lower alkenyl, hydroxy lower alkyl, —(CH$_2$)n-COOR$^{18}$, —CO—(CH$_2$)n-COOR$^{19}$;

$R^{17}$ is an unsubstituted, mono- or di-substituted five- or six-membered heteroaromatic ring connected by a ring carbon atom to the amide group shown, which five- or six-membered heteroaromatic ring contains from 1 to 4 heteroatoms selected from sulfur, oxygen or nitrogen, with one heteroatom being nitrogen which is adjacent to the connecting ring carbon atom; said mono- or di-substituted heteroaromatic ring being mono- or di-substituted at a position on a ring carbon atom other than adjacent to said connecting carbon atom with a substituent selected from the group consisting of lower alkyl, halo, nitro, cyano, —$(CH_2)$n-$OR^{20}$, —$(CH_2)$n-$COOR^{21}$, —$(CH_2)$n-$CONHR^{22}$, —$(CH_2)$n-$NHR^{23}$, n is 0, 1, 2, 3 or 4;

$R^{18}$, $R^{19}$, $R^{20}$, $R^{21}$, $R^{22}$ and $R^{23}$ are independently hydrogen or lower alkyl, and its pharmaceutically acceptable salts thereof.

3. A compound according to claim 1, wherein $R^4$ is an unsubstituted, mono- or di-substituted five- or six-membered heteroaromatic ring connected by a ring carbon atom to the amide group shown, which five- or six-membered heteroaromatic ring contains from 1 to 4 heteroatoms selected from sulfur, oxygen or nitrogen, with one heteroatom being nitrogen which is adjacent to the connecting ring carbon atom; said mono- or di-substituted heteroaromatic ring being mono- or di-substituted at a position on a ring carbon atom other than adjacent to said connecting carbon atom with a substituent selected from the group consisting of lower alkyl, halo, nitro, cyano, —$(CH_2)$n-$OR^{20}$, —$(CH_2)$n-$COOR^{21}$, —$(CH_2)$n-$CONHR^{22}$, —$(CH_2)$n-$NHR^{23}$, n is 0, 1, 2, 3 or 4;

$R^{20}$, $R^{21}$, $R^{22}$ and $R^{23}$ are independently hydrogen or lower alkyl, and its pharmaceutically acceptable salts thereof.

4. A compound according to claim 3, wherein $R^4$ is an unsubstituted, mono- or di-substituted five- or six-membered heteroaromatic ring selected from the group consisting of thiazolyl, imidazolyl, oxazolyl, thiadiazolyl, pyridinyl, pyrimidinyl, pyrazinyl, pyridazinyl, or triazinyl.

5. A compound according to claim 4, wherein $R^4$ is thiazolyl or pyridinyl, unsubstituted, mono- or di-substituted independently by halogen, lower alkyl or $(CH_2)$n-C(O)$OR^{21}$, wherein n is 0, 1 or 2 and $R^{21}$ is lower alkyl.

6. A compound according to claim 1, wherein $R^4$ is —C(O)$NHR^{16}$, where $R^{16}$ is hydrogen, lower alkyl, lower alkenyl, hydroxy lower alkyl, —$(CH_2)$n-$COOR^{18}$, —CO—$(CH_2)$n-$COOR^{19}$;

n is 0, 1, 2, 3 or 4;

$R^{18}$ and $R^{19}$ are independently hydrogen or lower alkyl, and its pharmaceutically acceptable salts thereof.

7. A compound according to claim 6, wherein $R^4$ is —C(O)$NHR^{16}$, and $R^{16}$ is lower alkyl or lower alkenyl.

8. A compound according to claim 5, wherein $R^1$ is hydrogen, halo, nitro or cyano.

9. A compound according to claim 8, wherein $R^1$ is hydrogen or halo.

10. A compound according to claim 9, wherein $R^2$ is hydrogen, halo, nitro, cyano, sulfonamido, lower alkyl, —$OR^5$, —$COOR^5$, perfluoro-lower alkyl, lower alkyl sulfonyl; or $R^2$ can be $R^{10}$—[$(CH_2)$y-W]z-, where W is oxygen, sulfur, —SO—, or —$SO_2$—, and $R^{10}$ is a heteroaromatic ring, connected by a ring carbon atom, which contains from 5 to 6 ring members with from 1 to 2 heteroatoms selected from the group consisting of oxygen, sulfur or nitrogen, or aryl containing 6 or 10 ring carbon atoms, or aryl containing 6 ring carbon atoms fused with a heteroaromatic ring containing 5 or 6 ring members with 1 or 2 heteroatoms in the ring being selected from the group consisting of nitrogen, oxygen or sulfur, or a saturated 5- or 6-membered cycloheteroalkyl ring, which contains from 1 to 2 heteroatoms selected from the group consisting of oxygen, sulfur and nitrogen, or a cycloalkyl ring having 5 or 6 carbon atoms, or —$NR^{11}R^{12}$, with $R^{11}$ and $R^{12}$ being independently hydrogen or lower alkyl;

y is independently 0, 1, 2, 3 or 4; z is independently 0 or 1; or $R^2$ can be $R^{13}$—$(CH_2)$t-U—, with U is —NHCO—, —CONH, —$NHSO_2$—, —$SO_2NH$— and $R^{13}$ in the same meaning of $R^{10}$ and perfluoro-lower alkyl, lower alkyl, lower alkoxycarbonyl or —$NR^{14}R^{15}$, $R^{14}$ and $R^{15}$ are independently hydrogen or lower alkyl; or together with the nitrogen atom to which they are attached form a five or six-membered heteroaromatic ring containing from 1 to 3 heteroatoms selected from sulfur, oxygen or nitrogen;

t is an integer from 0 to 4.

11. A compound according to claim 10, wherein $R^2$ is halo, lower alkyl sulfonyl or $R^{10}$—[$(CH_2)$y-W]z-.

12. A compound according to claim 11, wherein $R^2$ is sulfonylmethyl or $R^{10}$—[$(CH_2)$y-W]z- where W is $SO_2$.

13. A compound according to claim 12, wherein the aryl substituent and the group $R^3$ have a syn-relationship.

14. A compound according to claim 13, wherein V is cyclopentyl, cyclohexyl or cycloheptyl.

15. A compound according to claim 13, wherein V is cyclopentyl or cyclohexyl.

16. A pharmaceutical composition comprising a compound of claim 1, or a pharmaceutically acceptable salt thereof, and a pharmaceutically acceptable diluent or carrier.

17. A method for therapeutic treatment of type II diabetes, which comprises administering a compound of claim 1, or a pharmaceutically acceptable salt thereof, to a human being or animal in need thereof.

18. A compound of claim 1 selected from the group consisting of:

(±)-(E)-2-Cyclohexyl-1-(4-methanesulfonyl-phenyl)-cyclopropanecarboxylic acid (5-chloro-thiazol-2-yl)-amide;

(±)-(E)-2-Cyclohexylmethyl-1-(4-methanesulfonyl-phenyl)-cyclopropanecarboxylic acid thiazol-2-ylamide;

(±)-(E)-2-Cyclopentyl-1-[4-(3-diethylamino-propane-1-sulfonyl)-phenyl]-cyclopropanecarboxylic acid thiazol-2-ylamide;

(±)-(E)-2-Cyclohexyl-1-[4-(3-diethylamino-propane-1-sulfonyl)-phenyl]-cyclopropanecarboxylic acid thiazol-2-ylamide;

(±)-(E)-1-(3-Chloro-4-sulfamoyl-phenyl)-2-cyclohexyl-cyclopropanecarboxylic acid thiazol-2-ylamide;

(±)-(E)-2-Cyclohexyl-1-[4-(propane-2-sulfonyl)-phenyl]-cyclopropanecarboxylic acid thiazol-2-ylamide;

(±)-(E)-2-Cyclohexyl-1-[4-(propane-2-sulfonyl)-phenyl]-cyclopropanecarboxylic acid [1,3,4]thiadiazol-2-ylamide;

(±)-(E)-2-Cyclopentyl-1-(4-methanesulfonyl-phenyl)-cyclopropanecarboxylic acid (5-methyl-[1,3,4]thiadiazol-2-yl)-amide;

(±)-(E)-2-Cyclopentyl-1-(4-methanesulfonyl-phenyl)-cyclopropanecarboxylic acid isoxazol-3-ylamide;

(±)-(E)-2-Cyclopentyl-1-(4-methanesulfonyl-phenyl)-cyclopropanecarboxylic acid (5-methyl-isoxazol-3-yl)-amide;
(±)-(E)-(2-{[2-Cyclopentyl-1-(4-methanesulfonyl-phenyl)-cyclopropanecarbonyl]-amino}-thiazol-4-yl)-acetic acid ethyl ester;
(±)-(E)-(2- {[2-Cyclopentyl-1-(4-methanesulfonyl-phenyl)-cyclopropanecarbonyl]-amino}-thiazole-4-carboxylic acid ethyl ester;
(E)-2-Cyclopentyl-1-[4-(2-pyridin-2-yl-ethylsulfamoyl)-phenyl]-cyclopropanecarboxylic acid thiazol-2-ylamide;
(E)-2-Cyclopentyl-1-[4-(2-pyridin-2-yl-ethylsulfamoyl)-phenyl]-cyclopropanecarboxylic acid thiazol-2-ylamide;
(±)-(E)-2-Cyclopentyl-1-{4-[(pyridin-3-ylmethyl)-sulfamoyl]-phenyl}-cyclopropanecarboxylic acid thiazol-2-ylamide;
(±)-(E)-2-Cyclopentyl-1-(4-methanesulfonyl-phenyl)-cyclopropanecarboxylic acid thiazol-2-ylamide;
(±)-(E)-2,2-Dichloro-3-cyclopentyl-1-(4-methanesulfonyl-phenyl)-cyclopropanecarboxylic acid thiazol-2-ylamide;
(±)-(E)-3-Cyclopentyl-2,2-difluoro-1-(4-methanesulfonyl-phenyl)-cyclopropanecarboxylic acid thiazol-2-ylamide;
(±)-(E)-2-Cyclohexyl-1-(4-fluoro-phenyl)-cyclopropanecarboxylic acid thiazol-2-ylamide;
(±)-(E)-2-Cyclohexyl-1-(3-methanesulfonyl-phenyl)-cyclopropanecarboxylic acid thiazol-2-ylamide;
(±)-(E)-2-Cyclohexyl-1-(3-fluoro-4-methanesulfonyl-phenyl)-cyclopropanecarboxylic acid thiazol-2-ylamide;
(±)-(E)-2-Cyclopentyl-1-[4-(3-imidazol-1-yl-propylsulfamoyl)-phenyl]-cyclopropanecarboxylic acid thiazol-2-ylamide;
(E)-2-Cyclohexyl-1-(4-methanesulfonyl-phenyl)-cyclopropanecarboxylic acid (5-fluoro-thiazol-2-yl)-amide;
(±)-(E)-2-Cyclopentyl-1-[4-(pyridin-3-ylmethanesulfonyl)-phenyl]-cyclopropanecarboxylic acid (5-chloro-thiazol-2-yl)-amide;
(±)-(E)-2-Cyclopentyl-1-[4-(pyridin-3-ylmethanesulfonyl)-phenyl]-cyclopropanecarboxylic acid thiazol-2-ylamide
(±)-(E)-2-Cyclohexyl-1-(4-methylsulfamoyl-phenyl)-cyclopropanecarboxylic acid thiazol-2-ylamide;
(±)-(E)-2-Cyclohexyl-1-(4-methanesulfonyl-3-trifluoromethoxy-phenyl)-cyclopropanecarboxylic acid thiazol-2-ylamide;
(±)-(E)-2-Cyclohexyl-1-(4-methanesulfonyl-3-trifluoromethyl-phenyl)-cyclopropanecarboxylic acid thiazol-2-ylamide;
(±)-(E)-2-Cyclohexyl-1-(4-nitro-phenyl)-cyclopropanecarboxylic acid thiazol-2-ylamide;
(±)-(E)-3-[2-Cyclohexyl-1-(thiazol-2-ylcarbamoyl)-cyclopropyl]-benzoic acid; (±)-(E)-[2-Cyclohexyl-1-(4-methoxy-phenyl)-cyclopropanecarboxylic acid thiazol-2-ylamide];
(±)-(E)-4-[2-Cyclohexyl-1-(thiazol-2-ylcarbamoyl)-cyclopropyl]-N-pyridin-3-ylmethyl-benzamide;
(±)-(E)-4-[2-Cyclohexyl-1-(thiazol-2-ylcarbamoyl)-cyclopropyl]-N-methyl-benzamide;
(±)-(E)-1-(4-Acetylamino-phenyl)-2-cyclohexyl-cyclopropanecarboxylic acid thiazol-2-ylamide;
(±)-(E)-2-Cyclohexyl-1-(4-methanesulfonylamino-phenyl)-cyclopropanecarboxylic acid thiazol-2-ylamide;
(±)-(E)-2-Cyclohexyl-1-(4-methanesulfonyl-phenyl)-cyclopropanecarboxylic acid thiazol-2-ylamide;
2-(S)-Cyclohexyl-1-(R)-(4-methanesulfonyl-phenyl)-cyclopropanecarboxylic acid thiazol-2-ylamide;
2-(R)-Cyclohexyl-1-(S)-(4-methanesulfonyl-phenyl)-cyclopropanecarboxylic acid thiazol-2-ylamide;
(±)-(E)-2-Cyclopentylmethyl-1-(4-methanesulfonyl-phenyl)-cyclopropanecarboxylic acid thiazol-2-ylamide;
(±)-(E)-2-Cyclopentyl-1-(4-methanesulfonyl-phenyl)-cyclopropanecarboxylic acid (5-ethyl-[1,3,4]thiadiazol-2-yl)-amide;
(±)-(E)-2-Cyclohexyl-1-[3-(2-pyridin-2-yl-ethylsulfamoyl)-phenyl]-cyclopropanecarboxylic acid thiazol-2-ylamide;
(±)-(E)-3-Cyclohexyl-2,2-difluoro-1-(4-methanesulfonyl-phenyl)-cyclopropanecarboxylic acid thiazol-2-ylamide;
(±)-(E)-2-Cyclohexyl-1-[4-(2-pyridin-2-yl-ethylsulfamoyl)-phenyl]-cyclopropanecarboxylic acid thiazol-2-ylamide;
(±)-(E)-2-Cyclopentyl-1-(4-methanesulfonyl-phenyl)-cyclopropanecarboxylic acid (5-fluoro-thiazol-2-yl)-amide;
(±)-(E)-2-Cyclohexyl-1-(4-methanesulfonyl-3-trifluoromethoxy-phenyl)-cyclopropanecarboxylic acid [1,3,4]thiadiazol-2-ylamide;
(±)-(E)-2-Cyclohexyl-1-(4-methylsulfamoyl-3-trifluoromethyl-phenyl)-cyclopropanecarboxylic acid thiazol-2-ylamide;
(±)-(E)-2-Cyclohexyl-1-(4-methylsulfamoyl-3-trifluoromethyl-phenyl)-cyclopropanecarboxylic acid [1,3,4]thiadiazol-2-ylamide;
(±)-(E)-2-Cyclohexyl-1-(3-nitro-phenyl)-cyclopropanecarboxylic acid thiazol-2-ylamide;
(±)-(E)-4-[2-Cyclopentyl-1-(thiazol-2-ylcarbamoyl)-cyclopropyl]-benzoic acid methyl ester;
(±)-(E)-3-[2-Cyclohexyl-1-(thiazol-2-ylcarbamoyl)-cyclopropyl]-N-pyridin-3-ylmethyl-benzamide;
(±)-(E)-3-[2-Cyclohexyl-1-(thiazol-2-ylcarbamoyl)-cyclopropyl]-N-methyl-benzamide;
(±)-(E)-2-Cyclohexyl-1-(3-methanesulfonylamino-phenyl)-cyclopropanecarboxylic acid thiazol-2-ylamide;
(±)-(E)-2-Cyclohexyl-1-(4-methanesulfonyl-phenyl)-cyclopropanecarboxylic acid (5-methyl-thiazol-2-yl)-amide;
(±)-(E)-2-Cyclohexyl-1-(4-dimethylamino-phenyl)-cyclopropanecarboxylic acid thiazol-2-ylamide;
(E)-2-cyclohexyl-2-(4-methanesulfonyl-phenyl)-cyclopropane carboxylic acid thiazol-2-ylamide;
(E)-2-cyclopentyl-2-(4-methanesulfonyl-phenyl)-cyclopropane carboxylic acid thiazol-2-ylamide; and
(E)-2-Cyclohexyl-2-(4-methanesulfonyl-phenyl)-cyclopropane carboxylic acid 5-methyl-thiazol-2-ylamide;
or a pharmaceutically acceptable salt thereof.

* * * * *